(12) United States Patent
Wissner et al.

(10) Patent No.: US 6,548,496 B2
(45) Date of Patent: Apr. 15, 2003

(54) SUBSTITUTED 3-CYANO-[1.7], [1.5], AND [1.8] NAPHTHYRIDINE INHIBITORS OF TYROSINE KINASES

(75) Inventors: Allan Wissner, Ardsley, NY (US); Philip R. Hamann, Garnerville, NY (US); Ayako Yamashita, Englewood, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 10/032,587

(22) Filed: Dec. 21, 2001

(65) Prior Publication Data

US 2002/0165229 A1 Nov. 7, 2002

Related U.S. Application Data

(62) Division of application No. 09/550,824, filed on Apr. 18, 2000, now Pat. No. 6,355,636.
(60) Provisional application No. 60/155,255, filed on Apr. 12, 1999.

(51) Int. Cl.[7] .................... A61K 31/5377; A61P 35/00; C07D 413/12; C07D 471/04

(52) U.S. Cl. ..................... 514/234.5; 544/127; 546/14; 546/122

(58) Field of Search ............................ 544/127; 546/14, 546/122; 514/234.5

(56) References Cited

FOREIGN PATENT DOCUMENTS

| WO | WO 98/13350 | 6/1998 |
|---|---|---|
| WO | WO 98/43960 | 8/1998 |

*Primary Examiner*—Robert W. Ramsuer
(74) *Attorney, Agent, or Firm*—Joy S. Goudie

(57) ABSTRACT

This invention provides compounds of formula I having the structure

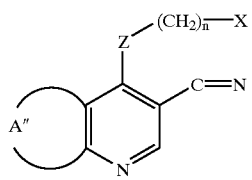

Wherein substitutions at A″, Z, n, and X are set forth in the specification.

13 Claims, No Drawings

SUBSTITUTED 3-CYANO-[1,7], [1,5], AND [1,8] NAPHTHYRIDINE INHIBITORS OF TYROSINE KINASES

This is a divisional application Ser. No. 09/550,824 filed on Apr. 18, 2000, now U.S. Pat. No. 6,355,636 which application claims the benefit of U.S. Provisional Application No. 60/155,255 filed Apr. 12, 1999, the entire disclosure of each being hereby incorporated by reference.

BACKGROUND OF THE INVENTION

This invention relates to certain substituted 3-cyano-[1,7], [1,5], and [1,8] naphthyridine compounds as well as the pharmaceutically acceptable salts thereof. The compounds of the present invention inhibit the action of certain growth factor receptor protein tyrosine kinases (PTK) and other protein kinases thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment or inhibition of polycystic kidney disease and colonic polyps in mammals. This invention also relates to the manufacture of said 3-cyano-[1,7], [1,5], and [1,8] naphthyridines, their use for the treatment of cancer and polycystic kidney disease, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of this is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology*, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7, 459 (1987)], and tumors involving other major organs [Gullick, W. J., *Brit. Med. Bull.*, 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future*, 17, 119 (1992) and Chang, C. J.; Geahlen, R. L., *J. Nat. Prod.*, 55, 1529 (1992)]. The compounds of this invention inhibit the kinase activity of EGF-R and are therefore useful for treating certain disease states, such as cancer, that result, at least in part, from deregulation of this receptor. The compounds of this invention are also useful for the treatment and prevention of certain pre-cancerous conditions, such as the growth of colon polyps, that result, at least in part, from deregulation of this receptor.

It is also known that deregulation of EGF receptors is a factor in the growth of epithelial cysts in the disease described as polycystic kidney disease [Du J., Wilson P. D., *Amer. J. Physiol.*, 269(2 Pt 1), 487 (1995); Nauta J., et al., *Pediatric Research*, 37(6), 755 (1995); Gattone V. H., et al., *Developmental. Biology*, 169(2), 504 (1995); Wilson P. D., et al., *Eur. J. Cell Biol.*, 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. (For review, see Rony Seger and Edwin G. Krebs, FASEB, Vol. 9, 726, June 1995). The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK is found to be essential for cell proliferation and differentiation. Overexpression and/or over-activation of MEK or ERK has been found to be associated with various human cancers (For example, Vimala S. Sivaraman, Hsien-yu Wang, Gerard J. Nuovo, and Craig C. Malbon, J. Clin. Invest. Vol. 99, No. 7 April 1997). It has been demonstrated that inhibition of MEK prevents activation of ERK and subsequent activation of ERK substrates in cells, resulting in inhibition of cell growth stimulation and reversal of the phenotype of ras-transformed cells (David T. Dudley, Long Pang, Stuart J. Decker, Alexander J. Bridges, and Alan R. Saltiel, PNAS, Vol. 92, 7686, August 1995). Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

Epithelial Cell Kinase (ECK) is a receptor protein tyrosine kinase (RPTK) belonging to the EPH (Erythropoietin Producing Hepatoma) family. Although originally identified as an epithelial lineage-specific tyrosine kinase, ECK has subsequently been shown to be expressed on vascular endothelial cells, smooth muscle cells, and fibroblasts. ECK is a type I transmembrane glycoprotein with the extracellular ligand-binding domain consisting of a cysteine-rich region followed by three fibronectin type III repeats. The intracellular domain of ECK possesses a tyrosine kinase catalytic domain that initiates a signal transduction cascade reflecting the ECK function. ECK binds and is subsequently activated by its counter-receptor, Ligand for Eph-Related Kinase (LERK)-1, which is an immediate early response gene product readily inducible in a lineage-unrestricted manner with proinflammatory cytokines such as IL-1 or TNF. Soluble LERK-1 has been shown to stimulate angiogenesis in part by stimulating ECK in a murine model of corneal angiogenesis. Unlike their normal counterparts, tumor cells of various lineages constitutively express LERK-1 and this expression can further be upregulated by hypoxia and proinflammatory cytokines. Many of these tumor cells also express ECK at higher levels than their normal counterparts, thereby creating an opportunity for autocrine stimulation via ECK: LERK-1 interaction. The increased expression of both ECK and LERK-1 has been correlated with the transformation of melanomas from the noninvasive horizontal phase of growth into very invasive vertically growing metastatic melanomas. Together, the ECK: LERK-1 interaction is believed to promote tumor growth via its tumor growth promoting and angiogenic effects. Thus, the inhibition of the ECK tyrosine kinase activity mediating signaling cascade induced by its binding and cross-linking to LERK-1 may be therapeutically beneficial in cancer, inflammatory diseases, and hyperproliferative disorders. As is shown below, the compounds of this invention inhibit the tyrosine kinase activity of ECK and are therefore useful for the treatment of the aforementioned disorders.

Growth of most solid tumors is dependent on the angiogenesis involving activation, proliferation and migration of vascular endothelial cells and their subsequent differentiation into capillary tubes. Angiogenization of tumors allows them access to blood-derived oxygen and nutrients, and also provides them adequate perfusion. Hence inhibiting angiogenesis is an important therapeutic strategy in not only cancer but also in a number of chronic diseases such as rheumatoid arthritis, psoriasis, diabetic retinopathy, age-related macular degeneration, and so on. Tumor cells produce a number of angiogenic molecules. Vascular Endothelial Growth Factor (VEGF) is one such angiogenic factor. VEGF, a homodimeric disulfide-linked member of the PDGF family, is an endothelial cell-specific mitogen and is known to cause profound increase in the vascular endothelial permeability in the affected tissues. VEGF is also a senescence-preventing survival factor for endothelial cells. Almost all nucleated tissues in the body possess the capability to express VEGF in response to various stimuli including hypoxia, glucose deprivation, advanced glycation products, inflammatory cytokines, etc. Growth-promoting angiogenic effects of VEGF are mediated predominantly via its signaling receptor Kinase insert Domain containing Receptor (KDR). The expression of KDR is low on most endothelial cells; however, activation with angiogenic agents results in a significant upregulation of KDR on endothelial cells. Most angiogenized blood vessels express high levels of KDR. KDR is a receptor protein tyrosine kinase with an extracellular VEGF-binding domain consisting of 7 immunoglobulin-like domains and a cytoplasmic domain containing the catalytic tyrosine kinase domain split by a kinase-insert region. Binding to VEGF causes dimerization of KDR resulting in its autophosphorylation and initiation of signaling cascade. Tyrosine kinase activity of KDR is essential for mediation of its functional effects as a receptor for VEGF. Inhibition of KDR-mediated functional effects by inhibiting KDR's catalytic activity is considered to be an important therapeutic strategy in the treatment of disease states such as cancer that depend on blood vessel growth. As is shown below, the compounds of this invention inhibit the tyrosine kinase activity of KDR and are therefore useful for the treatment of the aforementioned disease states.

The Src family of cytoplasmic protein tyrosine kinases consists of at least eight members that participate in a variety of signaling pathways (Schwartzberg, P. L., Oncogene 17: 1463–1468, 1998). The prototypical member of this tyrosine kinase family is p60$^{src}$ (Src). Src is involved in proliferation and migration responses in many cell types. In limited studies, Src activity was found to be elevated in breast, colon (~90%), pancreatic (>90%) and liver (>90%) tumors. Greatly increased Src activity was also associated with metastasis (>90%) and poor prognosis. Antisense Src message impedes growth of colon tumor cells in nude mice (Staley et al., Cell Growth & Differentiation. 8(3):269–74, 1997), suggesting that Src inhibitors should slow tumor growth. In addition to its role in cell proliferation, Src also acts in stress response pathways, including the hypoxia response, and nude mice studies with colon tumor cells expressing antisense Src message have reduced vascularization (Ellis, et al., J. Biol. Chem., 273(2):1052–7, 1998), which suggests that Src inhibitors would be anti-angiogenic as well as anti-proliferative. The compounds of this invention inhibit Src kinase and are therefore useful for the treatment of disease states that that depend, at least in part, on deregulation of Src kinases.

In addition to the above utilities some of the compounds of this invention are useful for the preparation of other compounds of this invention.

The compounds of this invention are certain substituted 3-cyano-[1.7], [1.5], and [1.8] naphthyridines. Throughout this patent application, the naphthyridines ring systems will be numbered as indicated in the formulas below.

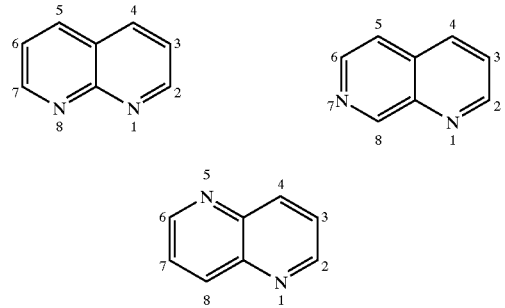

Some 3-cyano-quinoline derivatives are inhibitors of tyrosine kinases and are described in WO-9843960. The patent U.S. Pat. No. 5,780,482 and application WO-9500511 describe some condensed 4-aminopyridine compounds that have antirheumatic activity and can contain a cyano group at the 3-position. The application WO-9813350 describes some naphthyridines that are inhibitors of VEGF but these inhibitors do not have the important 3-cyano substituent.

Certain quinazoline derivatives are known to be inhibitors of protein tyrosine kinases. The application EP-520722 describes 4-anilinoquinazolines that contain simple substituents such as chloro, trifluoromethyl, or nitro groups at positions 5 to 8. The applications EP-566226 and U.S. Pat. No. 5,616,582 are similar but with a much larger variety of substituents now allowed at positions 5 to 8. The application WO-9609294 describes compounds with similar substituents at positions 5 to 8 and with the substituent at 4-position consisting of some polycyclic ring systems. Some simple substituted quinazolines are also described in the applications WO-9524190, WO-9521613, and WO-9515758. The applications EP-602851 (U.S. Pat. No. 5,580,870) and WO-9523141 cover similar quinazoline derivatives where the aryl group attached at position 4 can be a variety of heterocyclic ring structures. The application EP-635498 and U.S. Pat. No. 5,475,001 describe certain quinazoline derivatives that have alkenoylamino and alkynoylamino groups among the substituents at position 6 and a halogen atom at position 7. The applications WO-9519774 and WO-9823613 describes compounds where one or more of the carbon atoms at positions 5–8 of a quinazoline can be replaced with heteroatoms resulting in a large variety of bicyclic systems where the left-hand ring is a 5 and 6-membered heterocyclic ring; in addition, a variety of substituents are allowed on the left-hand ring. The application EP-682027-A1 describes certain pyrrolopyrimidine inhibitors of PTKs. The application WO-9519970 describes compounds in which the left-hand aromatic ring of the basic quinazoline structure has been replaced with a wide variety of different heterocyclic rings so that the resulting inhibitors are tricyclic.

DESCRIPTION OF THE INVENTION

This invention provides a compound of formula 1:

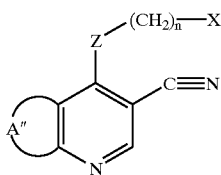

I wherein:

X is cycloalkyl of 3 to 7 carbon atoms, which may be optionally substituted with one or more alkyl of 1 to 6 carbon atom groups; or X is pyridinyl, pyrimidinyl, or Ph; or X is a bicyclic aryl or bicyclic heteroaryl ring system of 8 to 12 atoms, where the bicyclic heteroaryl ring contains 1 to 4 heteroatoms selected from N, O, and S; wherein the bicyclic aryl or bicyclic heteroaryl ring may be optionally mono-, di-, tri-, or tetra-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino; or X is the radical

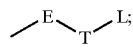

E is pyridinyl, pyrimidinyl, or Ph;

T is substituted on E at carbon and is

—NH(CH$_2$)$_m$, —O(CH$_2$)$_m$—, —S(CH$_2$)$_m$—, —NR(CH$_2$)$_m$—, —(CH$_2$)$_m$—

—(CH$_2$)$_m$NH—, —(CH$_2$)$_m$O—, —(CH$_2$)$_m$S—, or —(CH$_2$)$_m$NR—; #

L is a Ph; or

L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Pyridinyl, pyrimidinyl, or Ph are pyridinyl, pyrimidinyl, or phenyl radicals, respectively, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—, —O—, —S—, or —NR—;

R is alkyl of 1–6 carbon atoms, or carboalkyl of 2–7 carbon atoms;

A" is a diavalent moiety selected from the group

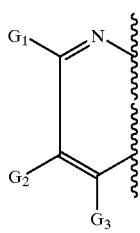 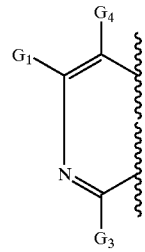 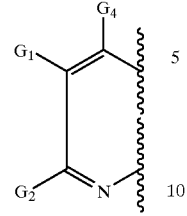

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_2NH$,

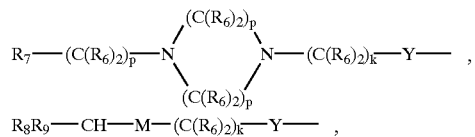

$R_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, with the proviso that $G_3$ and $G_4$ are not $R_2NH$;
Y is a divalent radical selected from the group consisting of

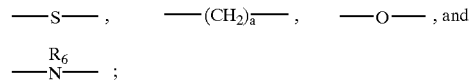

$R_7$ is —$NR_6R_6$, —$OR_6$, —J, —$N(R_6)_3^+$, or —$NR_6(OR_6)$;
M is >$NR_6$, —O—, >N—$(C(R_6)_2)_p NR_6R_6$, or >N—$(C(R_6)_2)_p$—$OR_6$;
W is >$NR_6$, —O— or is a bond;
Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4triazole, thiazole, thiazolidine, tetrazole, piperazine, furan, thiophene, tetrahydrothiophene, tetrahydrofuran, dioxane, 1,3-dioxolane tetrahydropyran, and

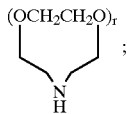

which may be optionally mono- or di-substituted on carbon with $R_6$, hydroxy, —$N(R_6)_2$, —$OR_6$—$(C(R)_2)_s$ $OR_6$ or —$(C(R_6)_2)_s N(R_6)_2$;
optionally mono-substituted on nitrogen with $R_6$; and
optionally mono or di-substituted on a saturated carbon with divalent radicals —O— or —$O(C(R_6)_2)_s O$—;
$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;
$R_2$, is selected from the group consisting of

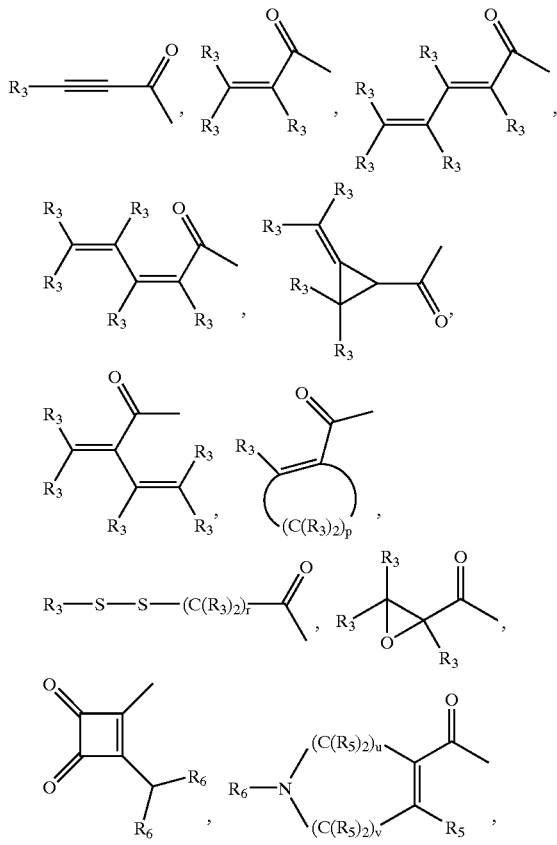

-continued

[chemical structures]

$R_3$ is hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$[(C(R_6)_2)_p]$N—$(C(R_6)_2)_r$—, $R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_5$ is hydrogen, alkyl of 1–6 carbon atoms, carboxy, carboalkoxy of 1–6 carbon atoms, phenyl, carboalkyl of 2–7 carbon atoms, $R_7$—$(C(R_6)_2)_p$—N$[(C(R_6)_2)_p]$N—$(C(R_6)_2)_r$—, $R_7$—$(C(R_6)_2)_s$—, $R_7(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$ and $R_9$ are each, independently, —$(C(R_6)_2)_r NR_6R_6$, or —$(C_6)_2)_r OR_6$;

J is independently hydrogen, chlorine, fluorine, or bromine;
Q is alkyl of 1–6 carbon atoms or hydrogen;
a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;
or a pharmaceutically acceptable salt thereof,
provided that
when $R_6$ is alkenyl of 2–7 carbon atoms or alkynyl of 2–7 carbon atoms, such alkenyl or alkynyl moiety is bound to a nitrogen or oxygen atom through a saturated carbon atom;
and provided that
when $R_3$ is bound to sulfur, it cannot be hydrogen, carboxy, carboalkoxy, or carboalkyl;
and provided that
when Y is —$NR_6$— and $R_7$ is —$NR_6R_6$, —$N(R_6)_3^+$, or —$NR_6(OR_6)$, then g=2–6;
when M is —O— and $R_7$ is —$OR_6$ then p=1–4;
when Y is —$NR_6$— then k=2–4;
when Y is —O— and M or W is —O— then k=1–4
when W is not a bond with Het bonded through a nitrogen atom then q=2–4
and when W is a bond with Het bonded through a nitrogen atom and Y is —O— or —$NR_6$— then k=2–4;
and finally provided that
when A″ is the moiety

[chemical structures with $G_1$, $G_2$, $G_3$, $G_4$]

n=0,
Z is NH,
$G_1$ is hydrogen, halogen, alkyl, alkoxy, hydroxy, alkanoyloxy of 2–6 carbon atoms, or phenoxy, and
$G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino,
then X can not be a pyridinyl, pyrimidinyl, or phenyl ring that is substituted with a hydroxy or alkoxy group.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Preferred bicyclic aryl or bicyclic heteroaryl ring systems include naphthalene, 1,2,3,4-tetrahydronaphthalene, tetralin, indane, 1-oxo-indane, 1,2,3,4-tetrahydroquinoline, naphthyridine, benzofuran, 3-oxo-1,3-dihydro-isobenzofuran, benzothiaphene, 1,1-dioxo-benzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzooxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydro-benzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzoazine, phthalazine, 1,4-dioxo-1,2,3,4-tetrahydro-phthalazine, 2-oxo-1,2-dihydro-quinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. A thio substituent on the bicyclic aryl or bicyclic heteroaryl moiety means that one of the carbon atoms has a thiocarbonyl group. When a compound of this invention contains a moiety which contains a heteroaryl ring, such heteroaryl ring does not contain O—O, S—S, or S—O bonds in the ring.

When L is a 5 or 6-membered heteroaryl ring, it may be fully unsaturated, partially saturated, or fully saturated. The heteroaryl ring can be bound to T via carbon or nitrogen. An oxo substituent on the heteroaryl ring means that one of the carbon atoms has a carbonyl group. A thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, and N,N-dialkylcarbamoyl, N-alkylaminoalkoxy, N,N-dialkylaminoalkoxy include both straight chain as well as branched carbon chains. The alkenyl portion of the alkenyl, alkenoyloxymethyl, alkenyloxy, alkenylsulfonamido, substituents include both straight chain as well as branched carbon chains and one or more sites of unsaturation and all possible configurational isomers. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$ radical, where $R"$ is an alkyl radical of 1–6 carbon atoms. Carboxyalkyl is defined as a $HO_2C$—$R'"$— radical where $R'"$ is a divalent alkyl radical of 1–6 carbon atoms. Carboalkoxyalkyl is defined as a $R"O_2C$—$R'"$— radical where $R'"$ is a divalent akyl radical and where $R"$ and $R'"$ together have 2–7 carbon atoms. Carboalkyl is defined as a —$COR"$ radical, where $R"$ is an alkyl radical of 1–6 carbon atoms. Alkanoyloxy is defined as a —$OCOR"$ radical, where $R"$ is an alkyl radical of 1–6 carbon atoms. Alkanoyloxymethyl is defined as $R"CO_2CH_2$— radical, where $R"$ is an alkyl radical of 1–6 carbon atoms. Alkoxymethyl is defined as $R"OCH_2$— radical, where $R"$ is an alkyl radical of 1–6 carbon atoms. Alkylsulphinyl is defined as $R"SO$— radical, where $R"$ is an alkyl radical of 1–6 carbon atoms. Alkylsulphonyl is defined as $R"SO_2$-radical, where $R"$ is an alkyl radical of 1–6 carbon atoms. Alkylsulfonamido, alkenylsulfonamido, alkynylsulfonamido are defined as $R"SO2NH$— radical, where $R"$ is an alkyl radical of 1–6 carbon atoms, an alkenyl radical of 2–6 carbon atoms, or an alkynyl radical of 2–6 carbon atoms, respectively. N-alkylcarbamoyl is defined as $R"NHCO$— radical, where $R"$ is an alkyl radical of 1–6 carbon atoms. N,N-dialkylcarbamoyl is defined as $R" R'NCO$— radical, where $R"$ is an alkyl radical of 1–6 carbon atoms, R' is an alkyl radical of 1–6 carbon atoms and R', and $R"$ may be the same or different. When X is substituted, it is preferred that it is mono-, di-, or tri-substituted, with mono- and di-substituted being most preferred. It is preferred that of the substituents $G_3$ and $G_4$, at least one is hydrogen and it is most preferred that both be hydrogen. It is also preferred that X is a phenyl ring, Z is —NH—, and n=0.

Het is a heterocycle, as defined above which may be optionally mono- or di-substituted on carbon with $R_6$, optionally mono-substituted on nitrogen with $R_6$, optionally mono- or di-substituted on carbon with hydroxy, —$N(R_6)_2$, or —$OR_6$, optionally mono or di-substituted on carbon with —$(C(R_6)_2)_sOR_6$ or —$(C(R_6)_2)_sN(R_6)_2$, and optionally mono or di-substituted on a saturated carbon with divalent —O— or —$O(C(R_6)_2)_sO$— (carbonyl and ketal groups, respectively); in some cases when Het is substituted with —O— (carbonyl), the carbonyl group can be hydrated. Het may be bonded to W when q=0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q=0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with $R_6$, such substitution may be on a ring carbon, or in the case of a nitrogen containing heterocycle, which also contains a saturated carbon-nitrogen, such nitrogen may be substituted with $R_6$ or in the case of a nitrogen containing heterocycle, which also contains an unsaturated carbon-nitrogen, such nitrogen may be substituted with $R_6$ in with case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-susbitituted 1,4-piperazine, N-subsitituted piperadine, and N-substituted pyrrolidine.

The compounds of this invention may contain one or more asymmetric carbon atoms; in such cases, the compounds of this invention include the individual diastereomers, the racemates, and the individual R and S entantiomers thereof. Some of the compound of this invention may contain one or more double bonds; in such cases, the compounds of this invention include each of the possible configurational isomers as well as mixtures of these isomers. When a compound of this invention contains a moiety containing the same substituent more than once (for example, when $R_7$ is —$NR_6R_6$), each substituent ($R_6$, in this example) may be the same or different.

The compounds of this invention can be prepared from commercially available starting materials or starting materials which can be prepared using literature procedures. More specifically, the preparation of the compounds and intermediates of this invention encompassed by Formulas 8a–c is described below in Flowsheet 1 where X, n, $G_2$, $G_1$, and $G_4$ are as described above. The reaction of 2 with a chlorinating reagent such as thionyl chloride or oxalyl chloride in methylene chloride using dimethylformamide as a catalyst gives the acid chlorides of formula 3. Condensation of 3 with reagent 4 in refluxing methylene chloride gives intermediate 5. Heating 5 with ammonium hydroxide in ethanol gives the quinolone 6 or the corresponding hydroxy naphthyridine tautomer. Chlorination with phosphorous oxychloride or oxalyl chloride furnishes 7. Condensation of 7 with various amines, anilines, alcohols, phenols, mercaptans, and thiophenols give the compounds of this invention 8a–c. Thus, 7 can be reacted with an amine or aniline by heating in an inert solvent such as tetrahydrofuran, butanol, or methoxyethanol to give compounds of Formula 8a where Z is —NH—. The reaction of 7 with a mercaptan or thiophenol in an inert solvent can be accomplished using a base such as sodium hydride to give compounds of Formula 8c where Z is —S—. The reaction of 7 with an alcohol or phenol in an inert solvent can be accomplished using a base such as sodium hydride to give compounds of Formula 8b where Z is —O—.

Flowsheet 1

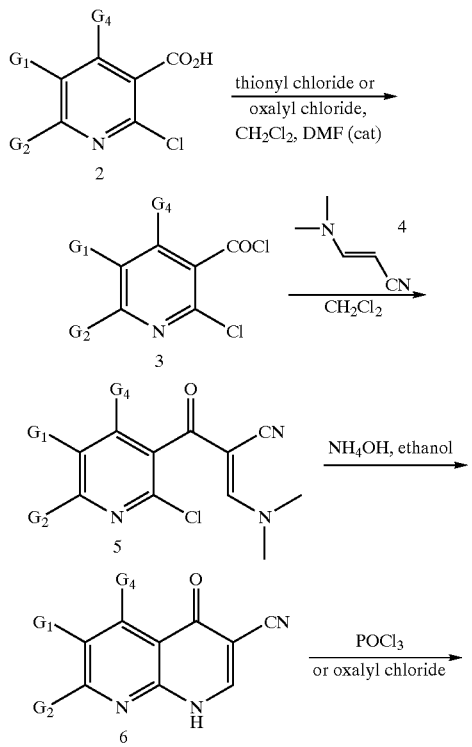

The preparation of the compounds of this invention encompassed by Formula 12, which are important intermediates for the preparation of other compounds of this invention, is described below in Flowsheet 2 where Z, X, n, $G_2$ and $G_4$ are as described above. Nitration of 9 with fuming nitric acid and sulfuric acid followed by chlorination 5 with refluxing phosphorous oxychloride gives 10. By using the methods described above in Flowsheet 1, 10 is converted to compounds represented by formula 11. Reduction of 11 with iron and ammonium chloride in a water-methanol mixture, at reflux, gives the compounds of this invention represented by formula 12. Compound 12, in turn, can be used to prepare other compounds of this invention.

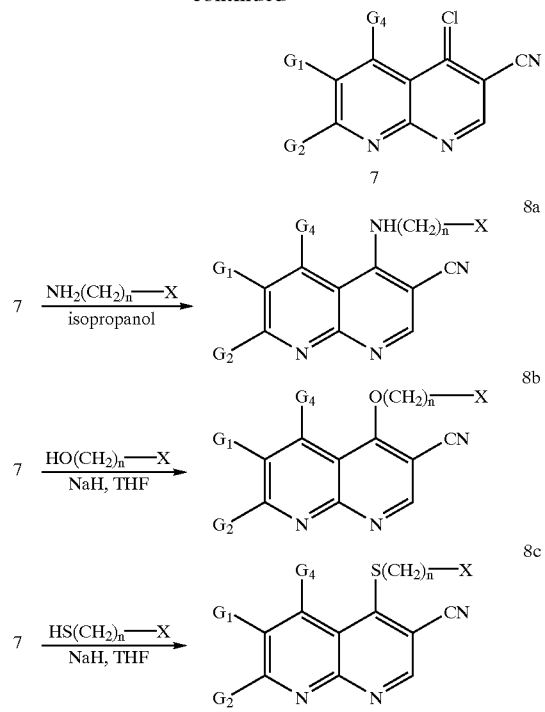

Flowsheet 2

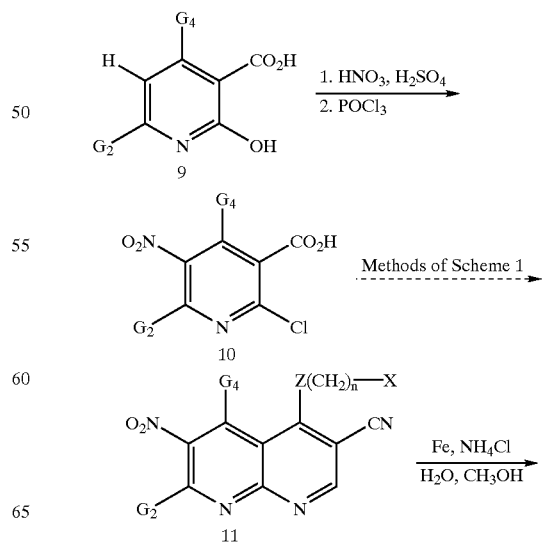

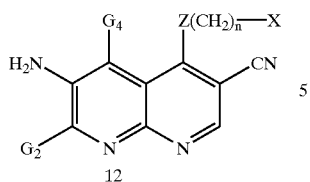

12

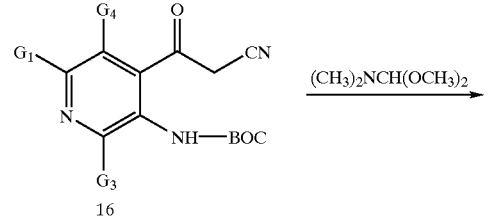

16

The preparation of the compounds and intermediates of this invention encompassed by Formulas 19a–c is described below in Flowsheet 3 where X, n, $G_1$, $G_3$, and $G_4$ are as described above. Reduction of the nitro group of 13 using hydrogen and a nickel catalyst followed by protection of the amino group as a t-butoxycarbonatederivative (BOC group) gives 14. Lithiation of 14 in ether using n-butyl lithium occurs at low temperature. Trapping with carbon dioxide followed by acidification gives a carboxylic acid which can be converted to the methyl ester by treatment with trimethylsilyl diazomethane in methanol. Alternatively, the lithiated species can be reacted with ethylchloroformate to give 15 directly. The lithium enolate of acetonitrile is prepare in tetrahydrofuran by addition of acetonitrile to a cold solution of n-butyl lithium. Addition of a tetrahydrofuran solution of 15 to the solution of lithio acetonitrile at low temperature gives, after work up, compound 16. The reaction of 16 with dimethylformamide dimethylacetal gives the hydroxy naphthyridine intermediate 17 or a tautomer thereof. Chlorination with phosphorous oxychloride or oxalyl chloride furnishes 18. Condensation of 18 with various amines, anilines, alcohols, phenols, mercaptans, and thiophenols give the compounds of this invention 19a–c.

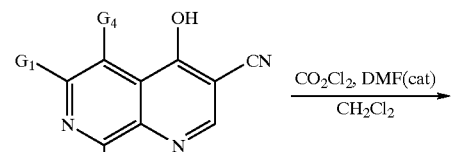

17

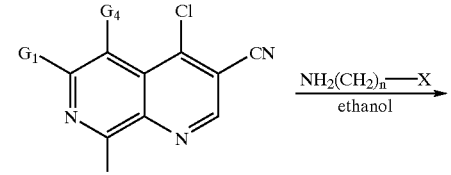

18

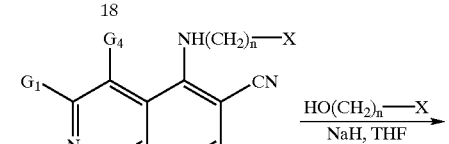

19a

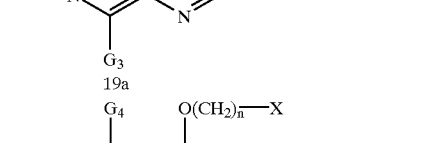

19b

Flowsheet 3

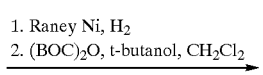

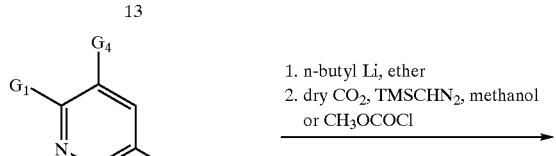

14

15

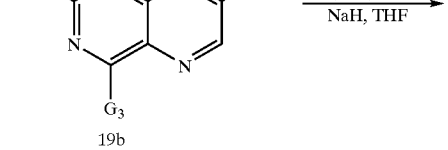

19c

The preparation of the compounds of this invention encompassed by Formulas 22a–d, which are important intermediates for the preparation of other compounds of this invention, is described below in Flowsheet 4 where Z, X, n, $G_3$, and $G_4$ are as described above and J" is fluorine or chlorine. The chloropyridine 20a can be converted to the corresponding fluoropyridine 20b by heating a solution of it with KF in dimethylsulfoxide. By using the methods describes above in Flowsheet 3, 20 is converted to compounds represented by formula 21. The fluoride atom of 21 can be displaced with p-methoxybenzylamino group by heating with p-methoxybenzylamine in an inert solvent. Cleavage of the p-methoxybenzylamino group using trifluoroacetic acid gives the 6-amino derivative 22a. Condensation of 21 with various other amines, anilines, alcohols, phenols, mercaptans, and thiophenols (some of which are listed in Lists A and B below) give the compounds of this invention 22b–d.

The preparation of the compounds and intermediates of this invention encompassed by Formulas 29a–c is described below in Flowsheet 5 where X, n, G., $G_2$, and $G_3$ are as described above. The nitro group of 23 can be reduced to the amino group by catalytic hydrogenation in an inert solvent. The condensation of 24 and the reagent 25 by heating in the absence of solvent gives 26. Thermal cyclization of 26 in refluxing Dowtherm or diphenyl ether gives the compound 27 or its corresponding tautomer. Chlorination of 27 in refluxing phosphorous oxychloride furnishes 28. Condensation of 28 with various amines, anilines, alcohols, phenols, mercaptans, and thiophenols gives the compounds of this invention 29a–c.

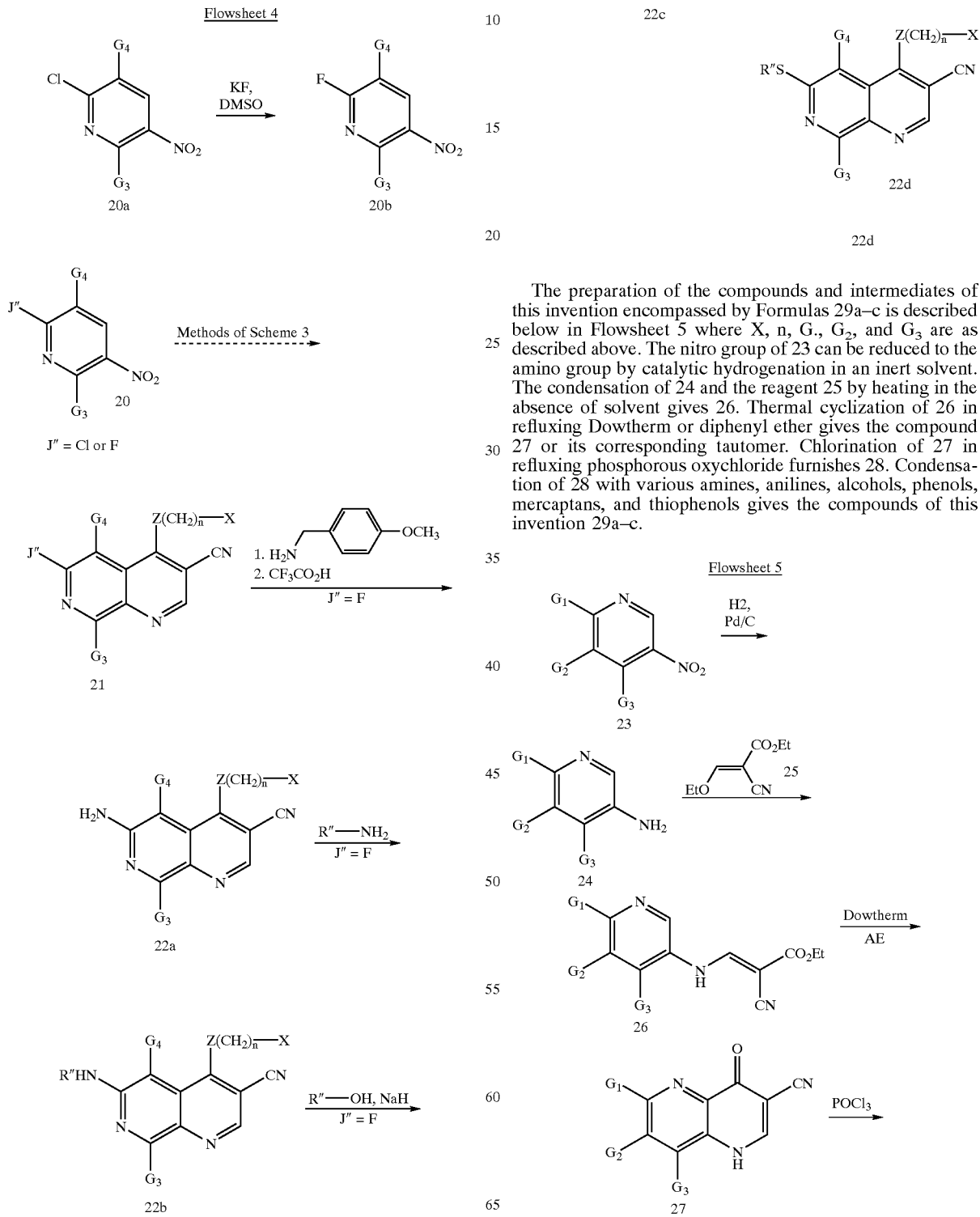

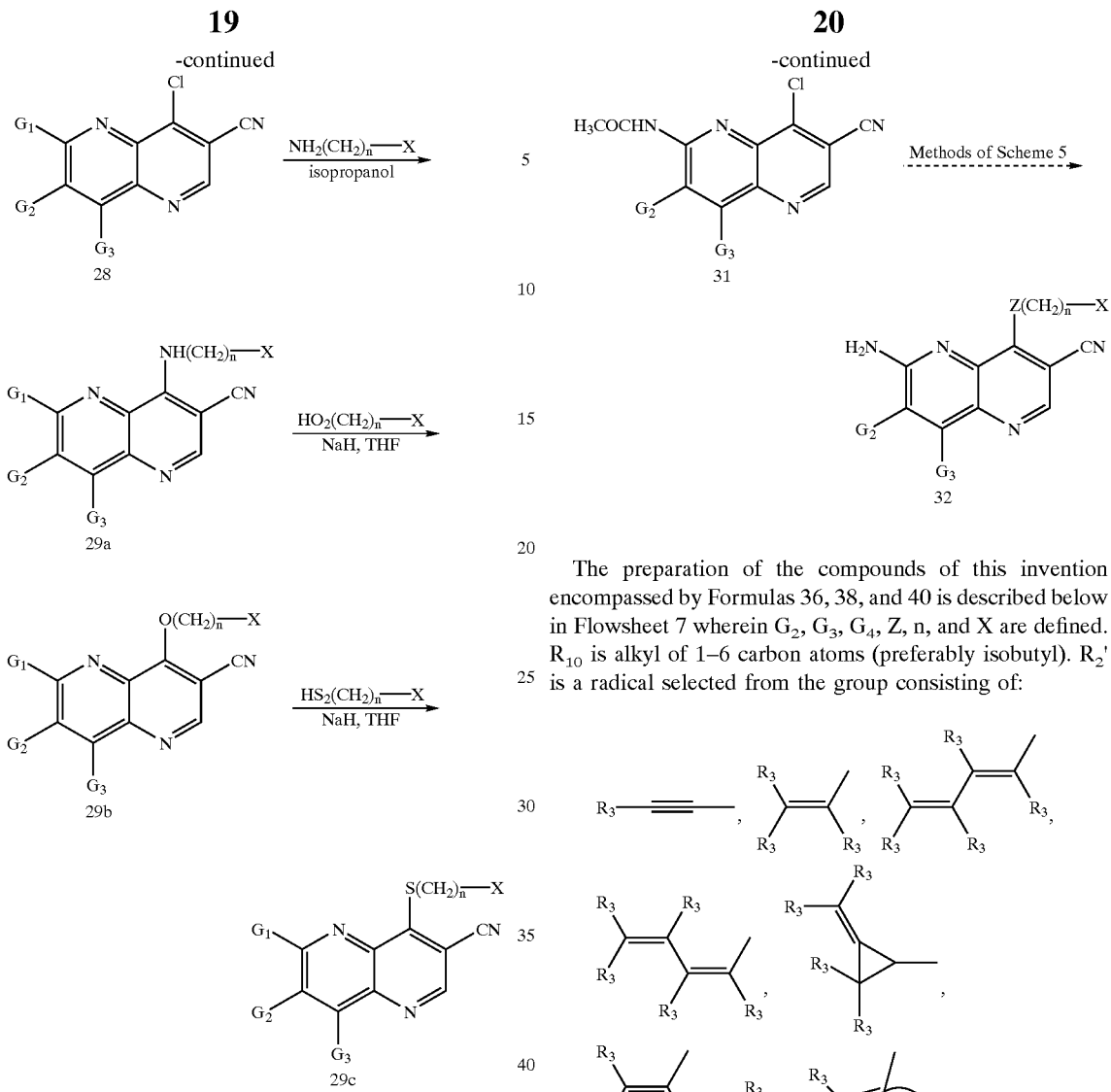

The preparation of the compounds of this invention encompassed by Formula 32, which are important intermediates for the preparation of other compounds of this invention, is described below in Flowsheet 6 where Z, X, n, $G_2$ and $G_3$ are as described above. Starting with compounds 30 where the amino group is protected as its acetate derivative and using the methods outlined above in Scheme 5, the compounds represented by formula 31 are obtained. Condensation of 31 with various amines, anilines, alcohols, phenols, mercaptans, and thiophenols as described in Flowsheet 5 gives the compounds of this invention 32. The conditions of these condensation reactions also results in removal of the acetate protecting group.

The preparation of the compounds of this invention encompassed by Formulas 36, 38, and 40 is described below in Flowsheet 7 wherein $G_2$, $G_3$, $G_4$, Z, n, and X are defined. $R_{10}$ is alkyl of 1–6 carbon atoms (preferably isobutyl). $R_2'$ is a radical selected from the group consisting of:

wherein $R_6$, $R_3$, $R_5$, J, s, r, u, and v are defined. According to the reactions outlined in Flowsheet 7, acylation of 33 with either an acid chloride of Formula 34 or a mixed anhydride of Formula 35 (which is prepared from the corresponding carboxylic acid) in an inert solvent such as tetrahydrofuran (THF) in the presence of an organic base such as pyridine, triethylamine, diisopropylethylamine, or N-methyl morpholine gives the compounds of this invention of Formula 36. In those cases where 34 or 35 have an asymmetric carbon atom, they can be used as the racemate or as the individual R or S entantiomers in which case the compounds of this invention will be in the racemic or R and S optically active forms, respectively. In those cases, where the $R_2'$ contains primary or secondary amino groups, the amino groups will first have to be protected prior to anhydride or acid chloride formation. Suitable protecting groups include, but are not limited to, tert-butoxycarbonyl (BOC) and benzyloxycarbonyl (CBZ) protecting groups. The former protecting group can be removed from the final products by treatment with an acid such as trifluoroactic acid while the latter protecting group can be removed by catalytic hydrogenation. In those cases where the $R_2'$ contains hydroxyl groups, the hydroxyl groups may first have to be protected prior to anhydride or acid chloride formation. Suitable protecting groups include, but are not limited to, t-butyldimethylsilyl, tetrahydropyranyl, or benzyl protecting groups. The first two protecting groups can be removed from the final products by treatment with an acid such as acetic acid or hydrochloric acid while the latter protecting group can be removed by catalytic hydrogenation. In those cases, in intermediates 33, 37, or 39 where X contains primary or secondary amino groups or hydroxyl groups, it may be necessary to protect these groups prior to the reaction with 34 or 35. The same amine or alcohol protecting groups describe above can be used and they can be removed from the products as previously described. In a similar manner, 37 can be converted to 38 and 39 can be converted to 40.

By using methods similar to that describe above in Flowsheet 7, the intermediates 41 can be converted to the compounds of this invention, 42. The analogous [1.8]-naphthyridine can be prepared in the same way.

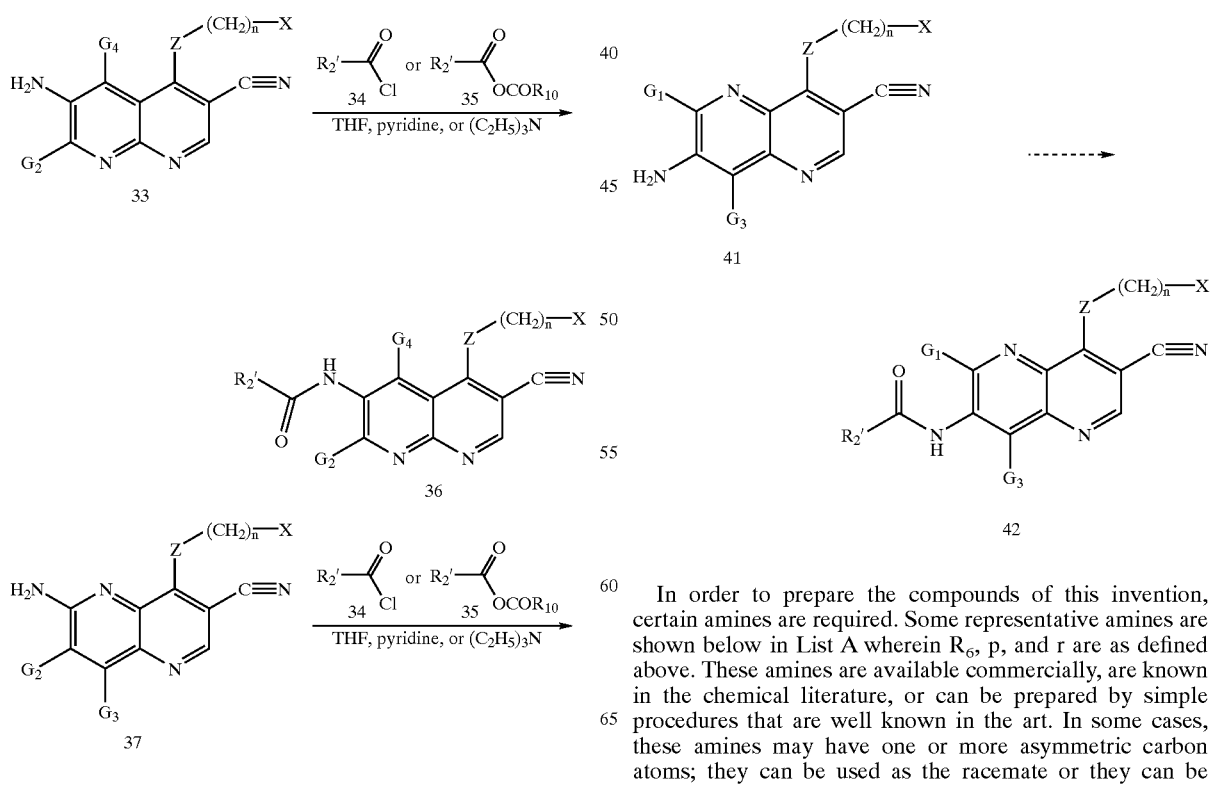

In order to prepare the compounds of this invention, certain amines are required. Some representative amines are shown below in List A wherein $R_6$, p, and r are as defined above. These amines are available commercially, are known in the chemical literature, or can be prepared by simple procedures that are well known in the art. In some cases, these amines may have one or more asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these amines, and other similar amines, will be represented by the generic structure of the formula:

(R')$_2$NH, wherein this formula can represent a primary or secondary amine.

List A

List B

In order to prepare the compounds of this invention certain alcohols are required. Some representative alcohols are shown below in List B wherein $R_6$, p, and r are as defined above. These alcohols are available commercially, are known in the chemical literature, or can be prepared by simple procedures that are well known in the art. In some cases, these alcohols may have one or more asymmetric carbon atoms; they can be used as the racemate or they can be resolved and used as the individual R or S entantiomers in which case the compounds of this invention will be in the racemic or optically active forms, respectively. Throughout this application in the Flowsheets shown below, these alcohols, and other similar alcohols, will be represented by the generic structure of the formula:

R'OH

In order to prepare some of the compounds of this invention certain mixed anhydrides are required; these are prepared as outlined below in the following Flowsheets wherein $R_6$, $R_{10}$, X, Z, n, and s are as defined above. J' is a halogen atom chlorine, bromine, or iodine, or is a toslyate (p-toluenesulfonate) or mesylate (methanesulfonate) group. The reaction of 43 with an amine of List A is accomplished by heating in an inert solvent such as tetrahydrofuran or N,N-dimethylformamide, or using potassium or cesium carbonate in acetone. The temperature and duration of the heating will depend on the reactivity of 43; longer reaction times and higher temperatures may be required when s is greater than 1. Treatment of 44 with an alkyl lithium reagent followed by quenching with an atmosphere of dry carbon dioxide furnishes the carboxylic acids of formula 45. These can be converted to mixed anhydrides of Formula 47 using a reagent such as isobutylchloroformate in an inert solvent such as tetrahydrofuran in the presence of a base such as N-methylmorpholine. These anhydrides can then be used to prepare the compounds of this invention as described in the above flowsheets. The reaction of 43 with an alcohol of List B is accomplished using sodium hydride or other non-nucleophic base such as potassium or cesium carbonate in an inert solvent such as tetrahydrofuran, acetone, or N,N-dimethylformamide. In some cases, the alcohol of List B can also be the solvent of the reaction. Treatment of 48 with an alkyl lithium reagent followed by quenching with an atmosphere of dry carbon dioxide furnishes the carboxylic acids of formula 49. These can be converted to mixed anhydrides formula 50 using a reagent such as isobutylchloroformate in an inert solvent such as tetrahydrofuran in the presence of a base such as N-methylmorpholine. These anhydrides can then be used to prepare the compounds of this invention as described in the above flowsheets.

Flowsheet 8

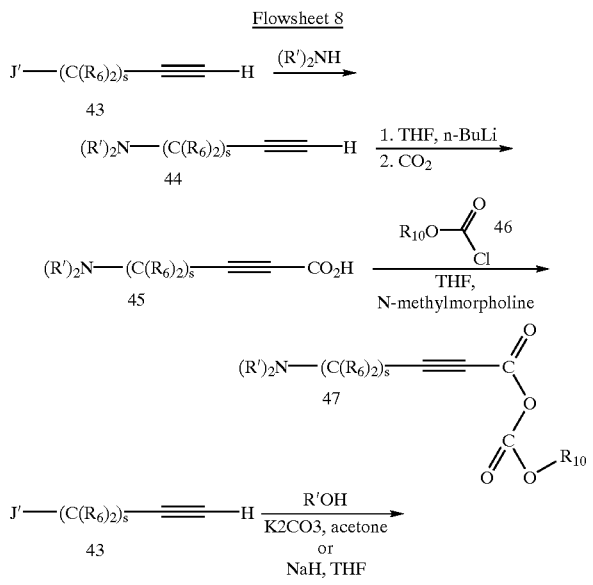

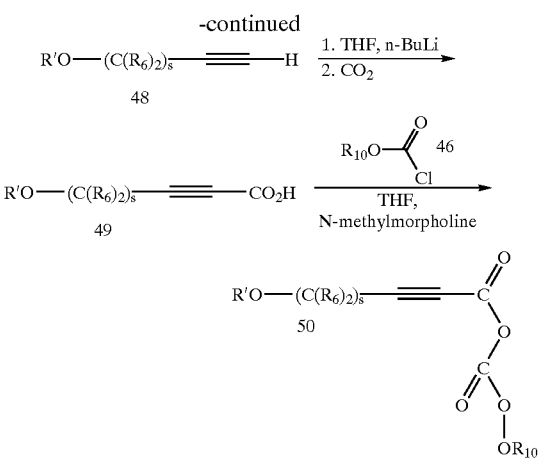

As outline in Flowsheet 9 below wherein $G_2$, $G_3$, $G_4$, $R_6$, $R_{10}$, X, Z, n, and s are as defined above, alcohols 51 can be protected with a t-butyl dimethysilyl protecting group by the reaction with the respective silyl chloride in methylene chloride in the presence of triethylamine and 4-N,N-dimethylamino pyridine (DMAP). The resulting protected alcohols, 52, are converted to the acetylenic Grignard reagents which, in turn, are maintained under an atmosphere of dry carbon dioxide to give the carboxylic acids 53. As described above these are converted to the mixed anhydrides 55 which on reaction with the 6-amino-[1,7] naphthyridine 56 gives 57. In the final step of the sequence, the silyl protecting group is removed by treating with acid in a protic solvent mixture to give the compounds represented by Formula 58. In the same manner the corresponding [1.8] naphthyridine 59 and the [1.5] naphthyridine 60 can be prepared.

Flowsheet 9

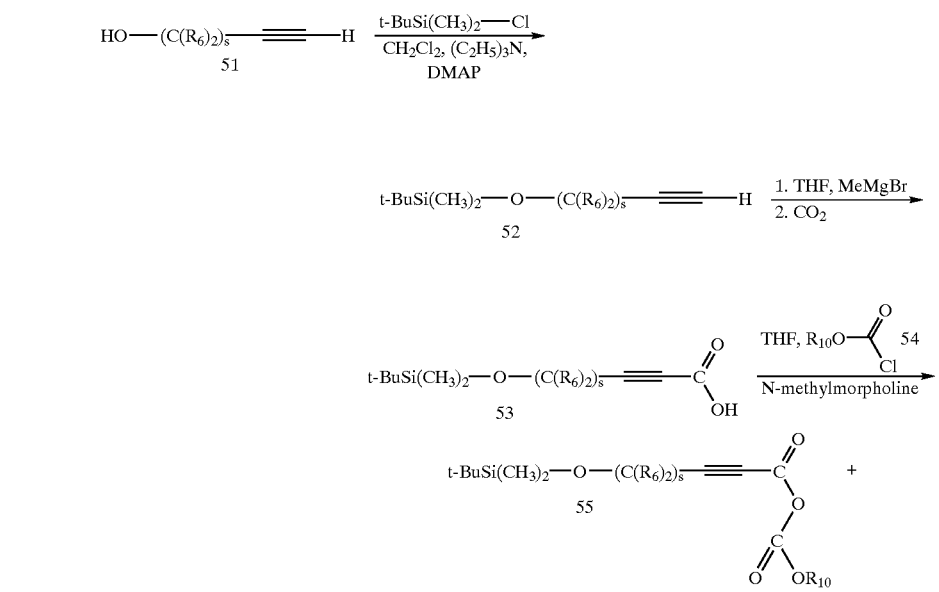

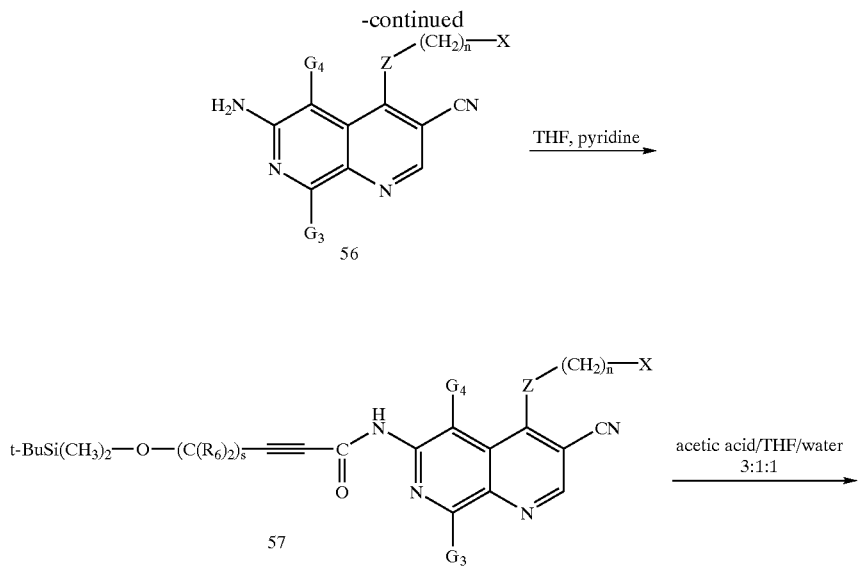

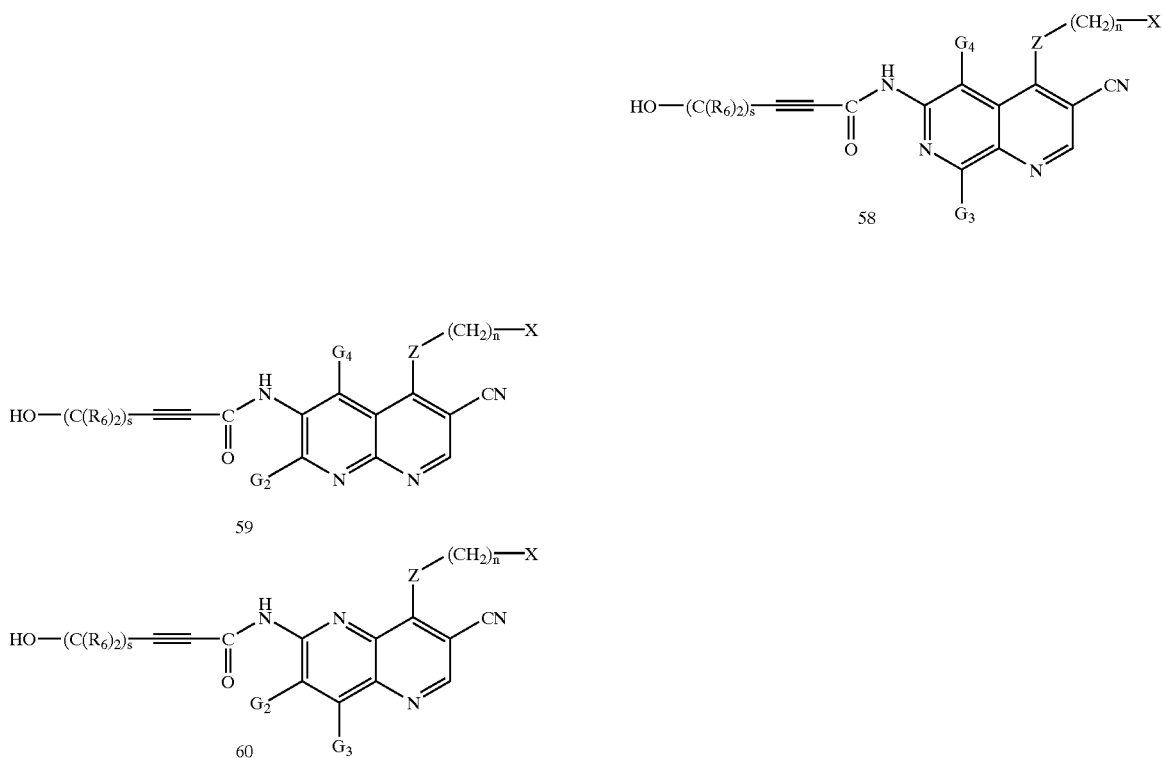

Compounds of this invention are also prepared as shown below in Flowsheet 10 wherein $G_2$, $G_3$, $G_4$, $R_6$, RIO, X, Z, n, and s are as defined above. J' is chlorine, bromine, or iodine, or is a toslyate or mesylate group. Treatment of 61 with an alkyl lithium reagent at low temperature followed by quenching with an atmosphere of dry carbon dioxide furnishes the carboxylic acids of formula 62. These can be converted to mixed anhydrides of Formula 63 using a reagent such as isobutylchloroformate in an inert solvent such as tetrahydrofuran in the presence of a base such as N-methylmorpholine. These anhydrides can then be used to prepare the compounds of this invention as by the reaction with the 6-amino-[1,7] naphthyridine 64 described above in the Flowsheets. The reaction of 65 with an alcohol of List B is accomplished using sodium hydride or other non-nucleophic base in an inert solvent such as tetrahydrofuran or N,N-dimethylformamide to give the compounds of this invention represented by 66. In some cases, the alcohol of List B can also be the solvent of the reaction. The reaction of 65 with an amine of List A gives the compounds of this invention represented by 67 is accomplished by heating in an inert solvent such as tetrahydrofuran or N,N-dimethylformamide, or using potassium or cesium carbonate in acetone. The temperature and duration of the heating will depend on the reactivity of 65; longer reaction times and higher temperatures may be required when s is greater than 1.
Flowsheet 10
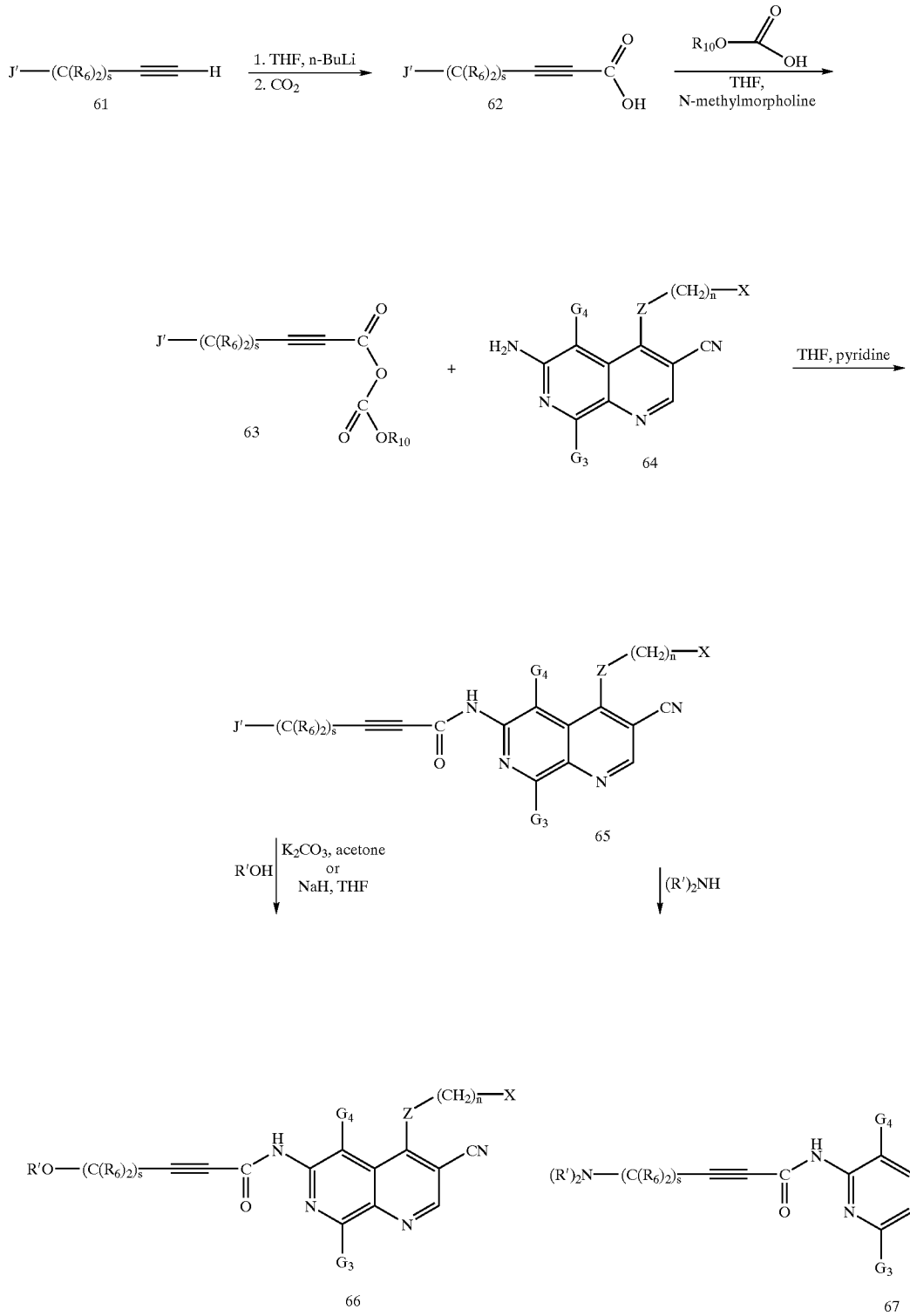

Using methods similar to that summarized above the [1.5] naphthyridines 68–70 and the [1.8] naphthyridines 71 and 72 can be prepared.

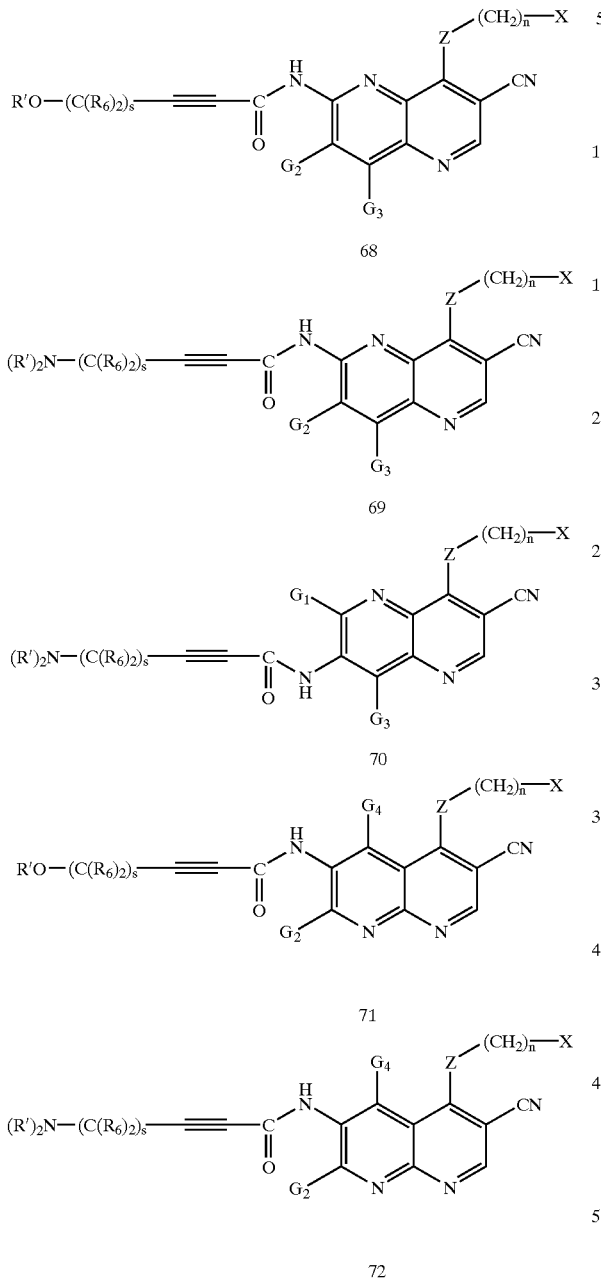

Other carboxylic acid chlorides and anhydrides needed to prepare some of the compounds of the invention are prepared as shown below in Flowsheet 11 wherein $R_6$, $R_3$, $R_{10}$, X, Z, J', n, and s are as defined above. Q' is an alkyl group of 1–6 carbon atoms. The esters 73, 77, or 82 can be hydrolyzed with a base such as barium hydroxide to give the respective carboxylic acid 74, 78, or 83. These acid can be converted to the respective carboxylic acid chlorides 75 or 80 by using oxalyl chloride and catalytic N,N-dimethylformamide in an inert solvent or respective mixed anhydrides 79 or 84 by using isobutyl chloroformate and an organic base such as N-methylmorpholine. The leaving group J' in compounds represented by Formula 81 and 76 can be displaced by the amines of List A or the alcohols of List B by using procedures previously described to give the intermediates 82 and 77, respectively. The carboxylic acid chlorides 75 and 80 and the anhydrides 79 and 84 can be used to prepare some of the compounds of this invention by using the methods outlined herein above in the Flowsheets.

Flowsheet 11

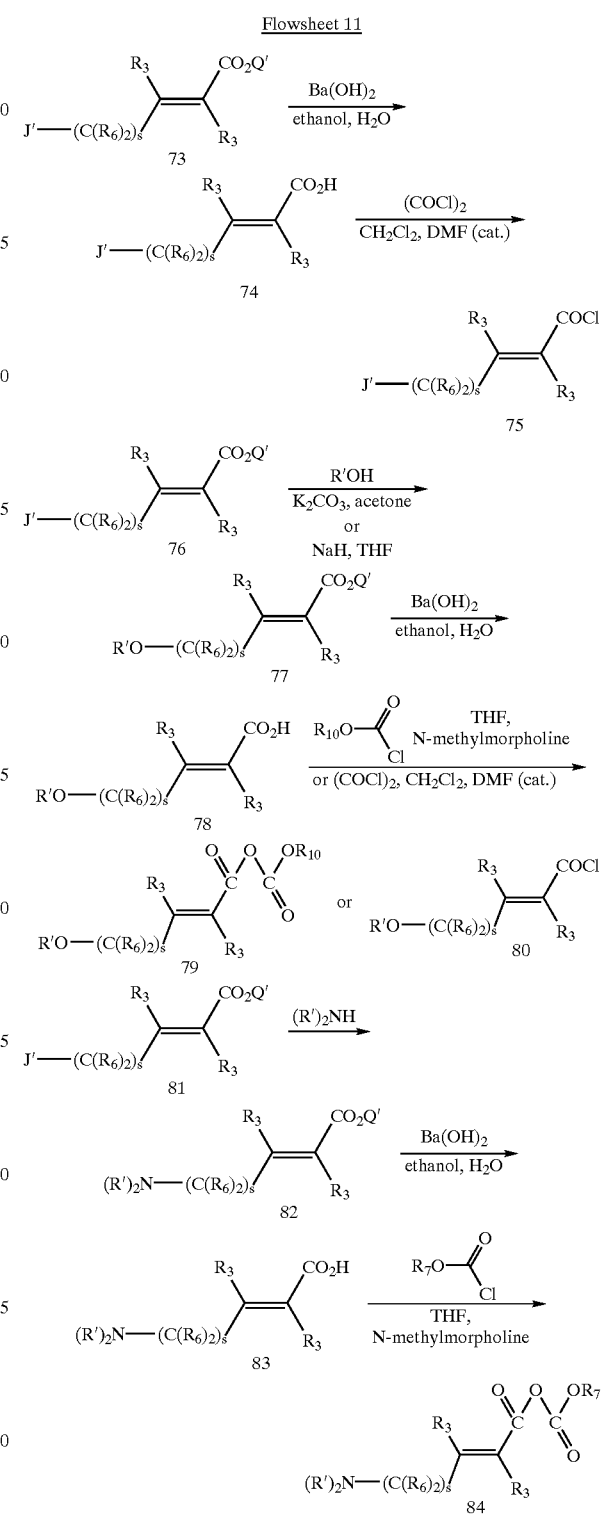

By using the methods identical to those outlined above in Flowsheet 11, it is possible to prepare the analogous carboxylic acid chlorides and anhydrides given below in List C wherein $R_6$, $R_3$, p, and s are as previously defined. G is the radical:

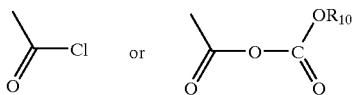

and A is the radical:
—N(R')$_2$, —O', or —J'
wherein —N(R')$_2$ is derived from the amines of List A, —OR' are derived from the alcohols of List B, and J' is a leaving group as defined previously. By making use of these carboxylic acid chlorides and anhydrides, by following the methods summarized in the above in Flowsheets, and by pursuing the details described in the examples given below, many of the compounds of this invention can be prepared.

List C

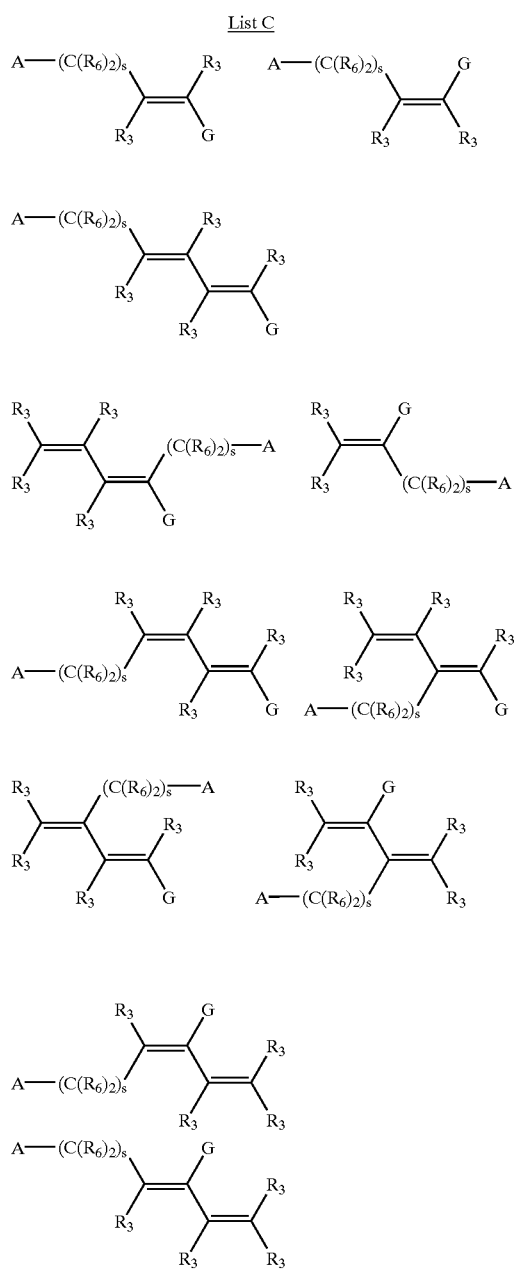

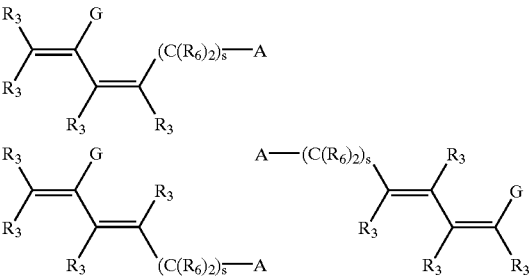

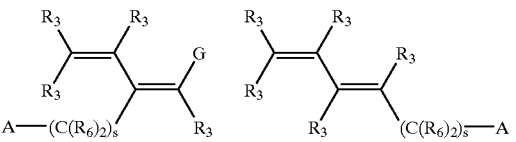

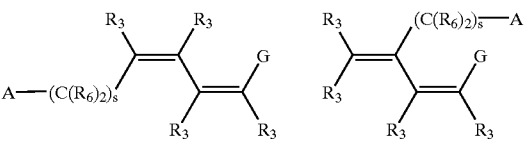

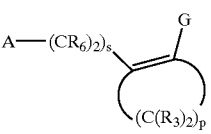

Compounds of this invention represented by Formulas 88–95 can be prepared as shown in Flowsheet 12 wherein $G_1$, $G_2$, $G_3$, $G_4$, $R_6$, $R_{10}$, X, Z, J', n, and s are as defined above. The reaction of the carboxylic acid chlorides 85 and the 6-amino-[1,7] naphthyridines 86 using an organic base in an inert solvent gives the compounds of this invention represented by Formula 87. The reaction of 87 with an alcohol of List B is accomplished using sodium hydride or other non-nucleophic base such as potassium or cesium carbonate in an inert solvent such as tetrahydrofuran, acetone, or N,N-dimethylformamide to give the compounds of this invention represented by 88. In some cases, the alcohol of List B can also be the solvent of the reaction. The reaction of 87 with an amine of List A to give the compounds of this invention represented by 89 is accomplished by heating in an inert solvent such as tetrahydrofuran or N,N-dimethylformamide. The temperature and duration of the heating will depend on the reactivity of 87; longer reaction times and higher temperatures may be required when s is greater than 1. In addition, by using this method, the carboxylic acid chlorides and mixed anhydrides listed in List C can be used to prepare the analogous compounds of this invention. By applying the methods summarized above, The corresponding [1.8]-naphthyridines 90 and 91 and the corresponding [1.5]-naphthyridines 92–95 can be prepared.

Flowsheet 12
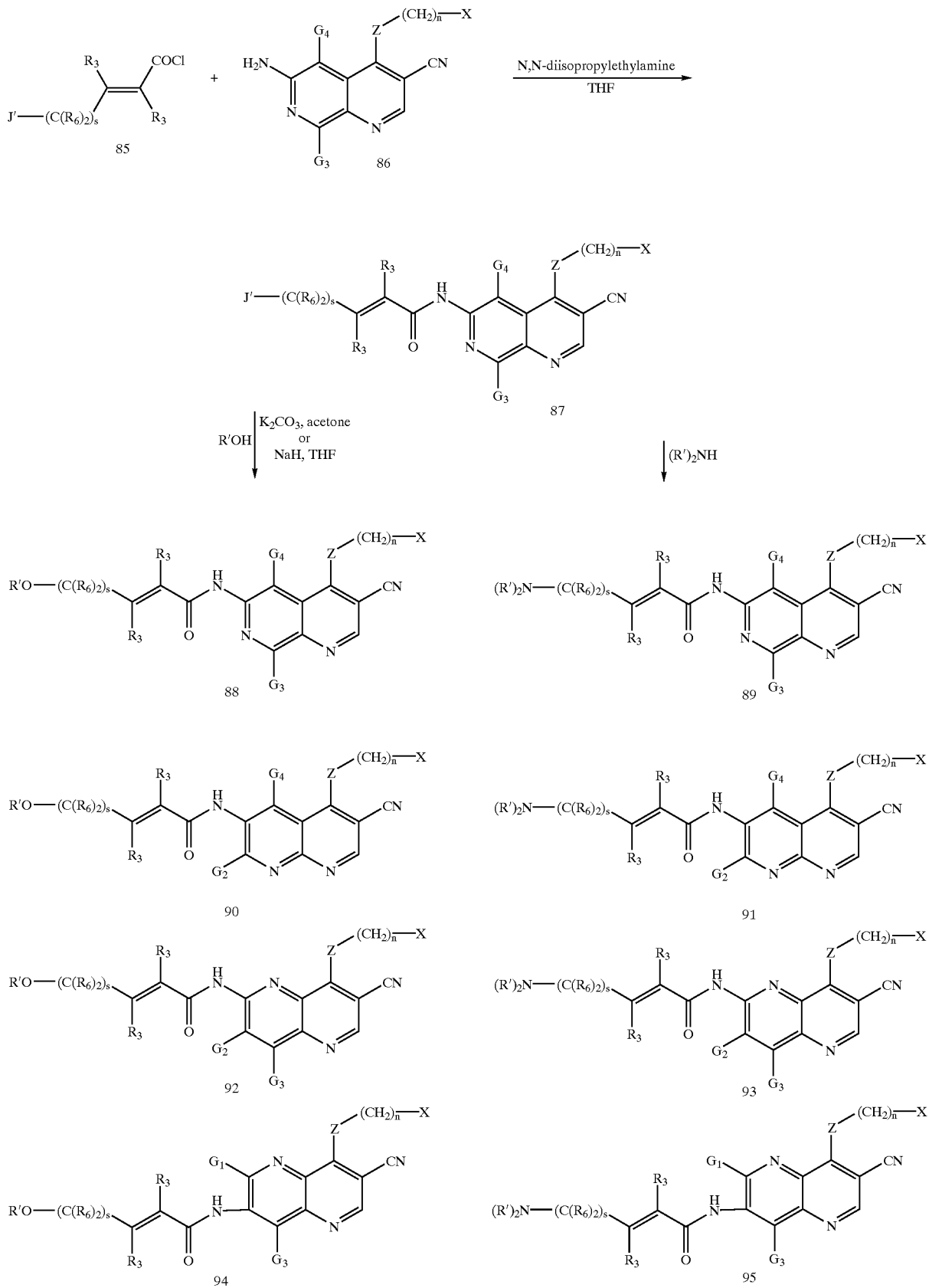

The reaction of 96 with a nitrogen containing heterocycle BET which also contains an unsaturated carbon-nitrogen bond is accomplished by refluxing in an inert solvent and gives the [1,7]-naphthyridines compounds 97 of this invention where the compound bears a positive charge. The counter anion J' can be replaced with any other pharmaceutically acceptable anion using the appropriate ion exchange resin. The corresponding [1.8]-naphthyridines and [1.5]-naphthyridines can be prepared in an analogous manner.

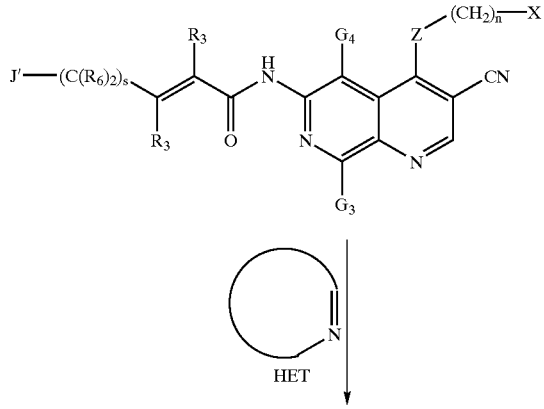

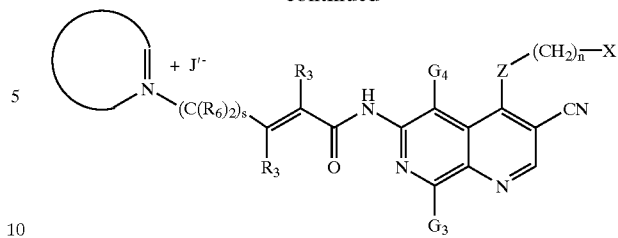

Some of the compounds of this invention can be prepared as outline below in Flowsheet 13 wherein $G_3$, $G_4$, $R_6$, $R_{10}$, X, Z, J, n, and r are as defined above. The acetylenic alcohols 98 can be coupled to the halides, mesylates, or tosylates 99 using a base such as sodium hydride in an inert solvent such as tetrahydrofuran. The resulting acetylene, 100, is then treated with an alkyl lithium reagent at low temperature. Maintaining the reaction under an atmosphere of carbon dioxide then gives the carboxylic acids 101. These, in turn, are reacted with the 6-amino-[1.7]-naphthyridines, 102, via the mixed anhydrides to give the compounds of this invention represented by Formula 103. Alternatively, the intermediates 106 can be prepared starting with an alcohol 104 by first treating it with a base such as sodium hydride in an inert solvent such as tetrahydrofuran and then adding an acetylene 105 that has an appropriate leaving group. In a similar manner, the amino alcohols represented by the formula: $(R_6)_2N-(C(R_6)_2)_r-OH$ by reacting with 105 can be converted to the compounds of this invention represented by the formula 107. In an entirely analogous manner the corresponding [1.5] and [1.8]-naphthyridines are prepared.

Flowsheet 13

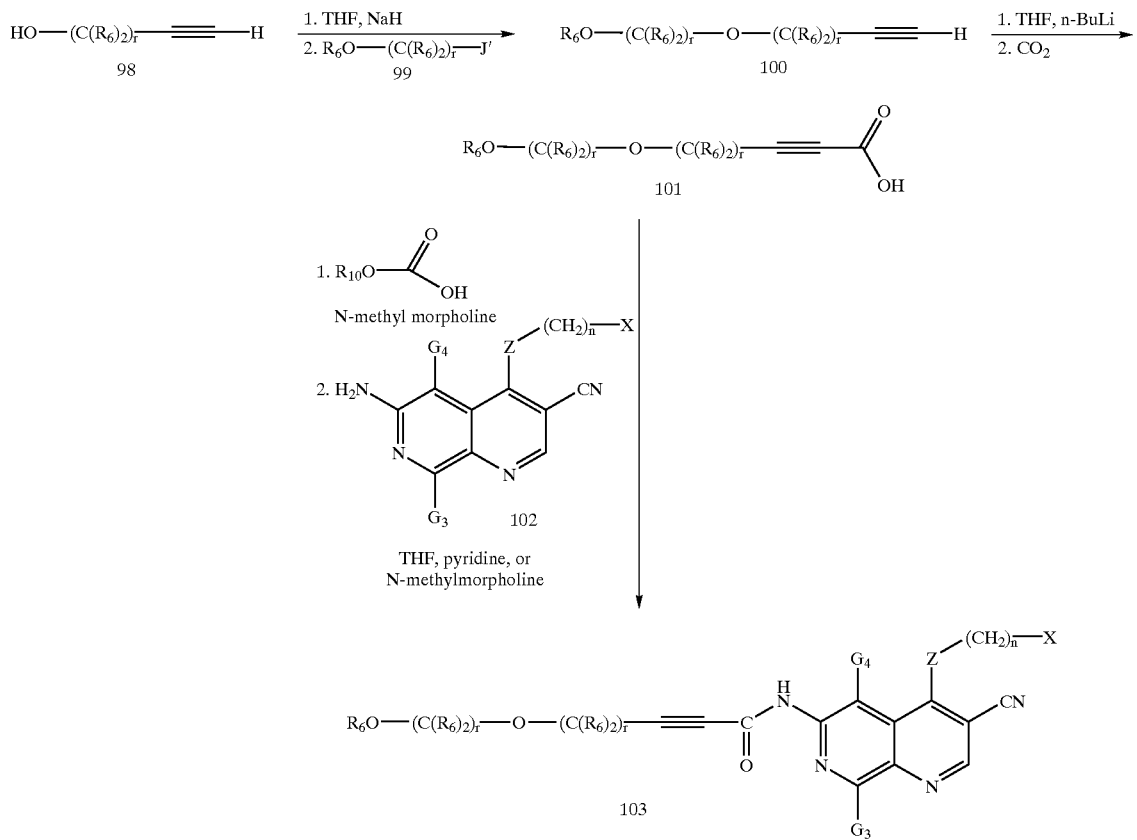

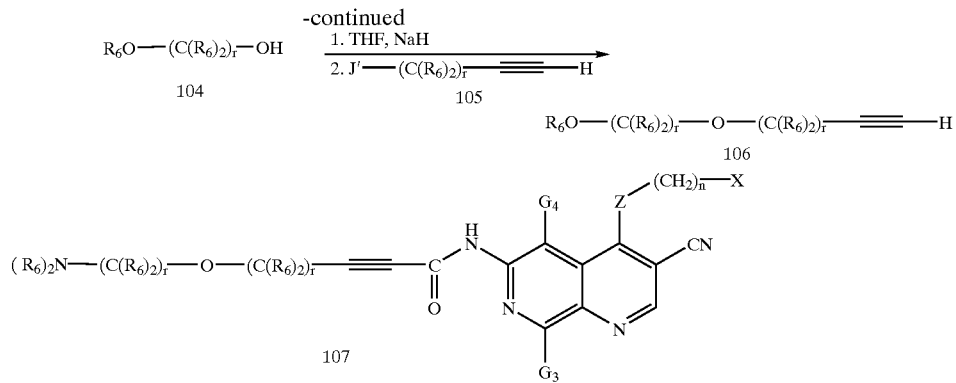

The compounds of this invention represented by Formula 111 and 112 are prepared as shown below in Flowsheet 14 wherein $G_3$, $G_4$, $R_6$, and n defined above and the amines $HN(R'')_2$ are selected from the group:

 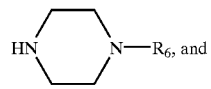 

Refluxing 108 and 109 in a solvent such as ethanol gives the intermediate 110 which can react with an amine in refluxing ethanol to give the compounds of this invention represented by Formula 112. Treating 110 with an excess of a sodium alkoxide in an inert solvent or a solvent from which the alkoxide is derived gives the compounds of this invention of Formula 111. In an entirely analogous manner the corresponding [1.5] and [1.8]-naphthyridines are prepared.

Flowsheet 14

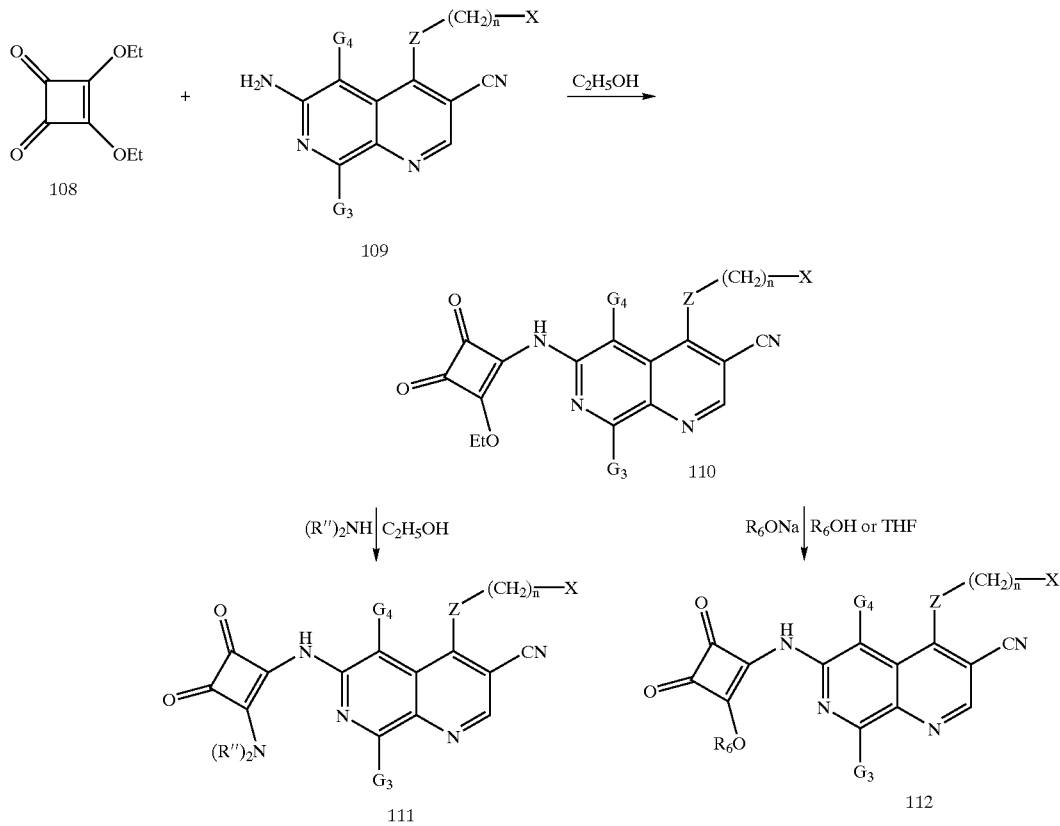

Compounds of this invention represented by Formula 118 can be prepared as shown in Flowsheet 15 wherein $G_3$, $G_4$, $R_6$, $R_3$, $R_{10}$, X, Z, n, and r are as defined above. The reaction of the mecapto carboxylic acids 113 with the reagents 114 give the compounds represented by Formula 115. Alternatively, 115 can be prepared from the mercaptan $R_3SH$ using the mercapto acid 113, triethylamine and 2,2'-dipyridyl disulfide. Mixed anhydride formation to give 116 followed by condensation with the 6-amino-[1,7]-naphthyridines 117 give the compounds of this invention. In an entirely analogous manner the corresponding [1.5] and [1.8]-naphthyridines are prepared.

Flowsheet 15

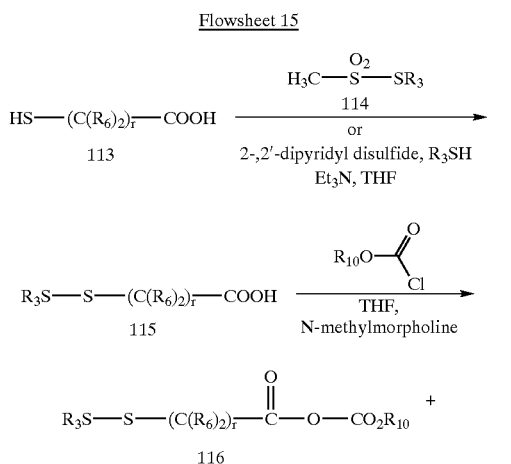

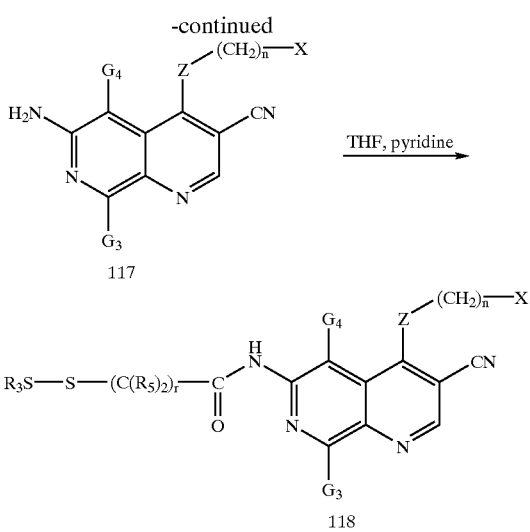

Compounds of this invention represented by Formulas 121–123 can be prepared as shown in Flowsheet 16 wherein $G_3$, $G_4$, $R_5$, J', X, Z, and n are as defined above. Q' is alkyl of 1–6 carbon atoms, alkoxy of 1–6 carbon atoms, hydroxy, or hydrogen. Akylation of 119 with the 6-amino-[1,7]-naphthyridines 120 can be accomplished by heating in an inert solvent such as N,N-dimethylformamide using a base such as potassium carbonate to give the compounds of this invention represented by the Formula 121. When Q' is alkoxy, the ester group can be hydrolyzed to an acid using a base such as sodium hydroxide in methanol. In a similar manner, by using intermediates 124 and 125, the compounds of this invention represented by Formulas 122 and 123 can be prepared, respectively. In an entirely analogous manner the corresponding [1.5] and [1.8]-naphthyridines are prepared.

Flowsheet 16

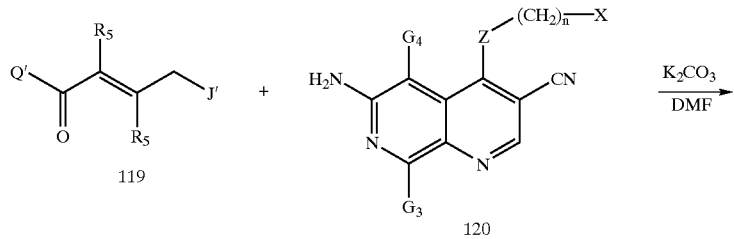

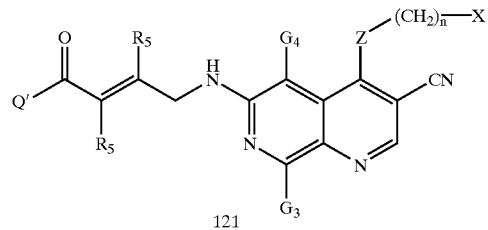

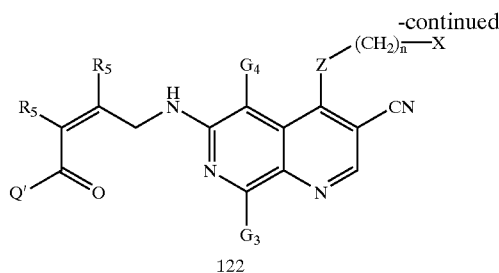

122

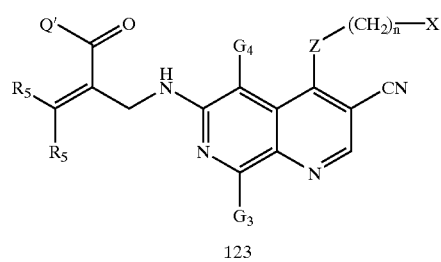

123

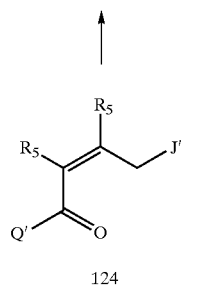

124

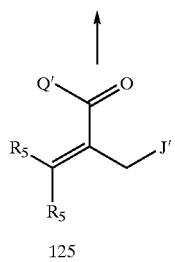

125

Compounds of this invention represented by Formula 128 can be prepared as shown in Flowsheet 17 wherein $G_3$, $G_4$, $R_5$, X, Z, and n are as defined above. The reaction of reagent 126 with the 6-amino-[1,7]-naphthyridines 127 is accomplished using an excess of an organic base such as triethylamine and an inert solvent such as tetrahydrofuran to give compounds of this invention represented by Formula 128. In an entirely analogous manner the corresponding [1.5] and [1.8]-naphthyridines are prepared.

Flowsheet 17

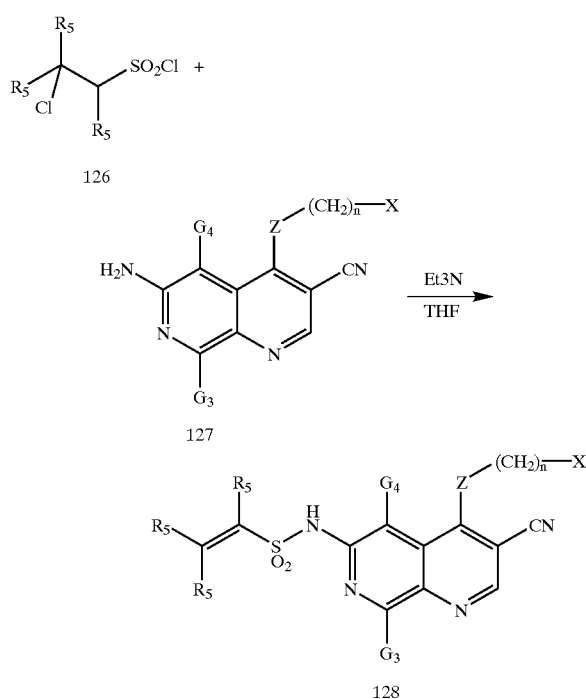

With respect to the above Flowsheets 1–17, in those cases where $G_1$, $G_2$, $G_3$, $G_4$, or other substituent may contain an asymmetric carbon atom, the intermediates can be used as the racemate or as the individual R or S entantiomers in which case the compounds of this invention will be in the racemic or R and S optically active forms, respectively. In cases where the substituents may contribute more than one asymmetric carbon atom, diasteriomers may be present; these can be separated by methods well known in the art including, but not limited to, fractional crystallization and chromatographic methods. In those cases where $G_1$, $G_2$, $G_3$, $G_4$, or other substituents contain primary or secondary amino groups, the amino groups may first have to be used in protected form prior to applying the chemistry described in the above Flowsheets. Suitable protecting groups include, but are not limited to, tert-butoxycarbonyl (BOC) and benzyloxycarbonyl (CBZ) protecting groups. The former protecting group can be removed from the final products by treatment with an acid such as trifluoroactic acid while the latter protecting group can be removed by catalytic hydrogenation. In those cases where the $G_1$, $G_2$, $G_3$, $G_4$, or other substituents contain hydroxyl groups, the hydroxyl groups may first have to be used in protected form prior to applying the chemistry described in the above Flowsheets. Suitable protecting groups include, but are not limited to, t-butyldimethylsilyl, tetrahydropyranyl, or benzyl protecting groups. The first two protecting groups can be removed from the final products by treatment with an acid such as acetic acid, hydrofluoric acid, or hydrochloric acid while the latter protecting group can be removed by catalytic hydrogenation.

There are certain functional group manipulations that are useful to prepare the compounds of this invention that can be applied to various intermediate 3-cyano-naphthyridines as well as to the final compounds of this invention. These manipulations refer to the substituents $G_1$, $G_2$, $G_3$, or $G_4$ that are located on the 3-cyano-naphthyridines shown in the above Flowsheets. Some of these functional group manipulations are described below:

Where one or more of $G_0$, $G_2$, $G_3$, or $G_4$ is a nitro group, it can be converted to the corresponding amino group by reduction using a reducing agent such as iron in acetic acid or by catalytic hydrogenation. Where one or more of $G_1$, $G_2$, $G_3$, or $G_4$ is an amino group, it can be converted to the corresponding dialkyamino group of 2 to 12 carbon atoms by alkylation with at least two equivalents of an alkyl halide of 1 to 6 carbon atoms by heating in an inert solvent or by reductive alkylation using an aldehyde of 1 to 6 carbon atoms and a reducing agent such as sodium cyanoborohydride. Where one or more of $G_1$, $G_2$, $G_3$, or $G_4$ is a methoxy group, it can be converted to the corresponding hydroxy group by reaction with a demethylating agent such as boron tribromide in an inert solvent or by heating with pyridinium chloride with or without solvent. Where one or more of $G_1$, $G_2$, $G_3$, or $G_4$ is an amino group, it can be converted to the corresponding alkylsulfonamido, alkkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Where one or more of $G_1$, $G_2$, $G_3$, or $G_4$ is an amino group, it can be converted to the corresponding alkyamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof. Where one or more of $G_0$, $G_2$, $G_3$, or $G_4$ is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a catalyst. Where one or more of $G_1$, $G_2$, $G_3$, or $G_4$ is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a catalyst. Where one or more of $G_1$, $G_2$, $G_3$, or $G_4$ is hydroxy, it can be converted to the corresponding alkynoyloxy group of 1–6 carbon atoms by reaction with an appropriate carboxylic acid chloride, anhydride, or mixed anhydride in a inert solvent using pyridine or a trialkylamine as a catalyst. Where one or more of $G_1$, $G_2$, $G_3$, or $G_4$ is carboxy or a carboalkoxy group of 2–7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms. Where one or more of $G_1$, $G_2$, $G_3$, or $G_4$ is a halomethyl group, it can be converted to an alkoxymethyl group of 2–7 carbon atoms by displacing the halogen atom with a sodium alkoxide in an inert solvent. Where one or more of $G_1$, $G_2$, $G_3$, or $G_4$ is a halomethyl group, it can be converted to an aminomethyl group, N-alkylaminomethyl group of 2–7 carbon atoms or N,N-dialkylaminomethyl group of 3–14 carbon atoms by displacing the halogen atom with ammonia, a primary, or secondary amine, respectively, in an inert solvent.

In addition to the methods described herein above and in the examples below, WO-9843960 describes methods that are useful for the preparation of the compounds of this invention. In addition there are some patent applications that describe the preparation of certain quinazolines, many of the synthetic methods therein are applicable to the preparation of substituted 3-cyano-[1,7], [1.5], and [1 8] naphthyridines of this invention. The chemical procedures described in the application WO-9633981 can be used to prepare the naphthyridine intermediates used in this invention wherein $G_1$, $G_2$, $G_3$, or $G_4$ are alkoxyalkylamino groups. The chemical procedures described in the application WO-9633980 can be used to prepare the 3-cyano-naphthyridine intermediates used in this invention wherein $G_1$, $G_3$, $G_2$, or $G_4$ are aminoalkylalkoxy groups. The chemical procedures described in the application WO-9633979 can be used to prepare the naphthyridine intermediates used in this invention wherein $G_1$, $G_3$, $G_2$, or $G_4$ are alkoxyalkylamino groups. The chemical procedures described in the application WO-9633978 can be used to prepare the naphthyridine intermediates used in this invention wherein $G_1$, $G_3$, $G_2$, or $G_4$ are aminoalkylamino groups. The chemical procedures described in the application WO-9633977 can be used to prepare the naphthyridineintermediates used in this invention wherein $G_1$, $G_3$, $G_2$, or $G_4$ are aminoalkylalkoxy groups. Although the above patent applications describe compounds where the indicated functional group have been introduced onto the 6-position of a quinazoline, the same chemistry can be used to introduce the same groups unto positions occupied by the $G_1$, $G_3$, $G_2$, and $G_4$ substituents of the naphthyridine compounds of this invention.

Representative compounds of this invention were evaluated in several standard pharmacological test procedures that showed that the compounds of this invention possess significant activity as inhibitors of protein tyrosine kinase and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R) Using Recombinant Enzyme Representative test compounds were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR. A recombinant baculovirus (vHcEGFR52) was constructed containing the EGFR cDNA encoding amino acids 645–1186 preceded by Met-Ala-(His)$_6$. Sf9 cells in 100 mm plates were infected at an moi of 10 pfu/cell and cells were harvested 48 h post infection. A cytoplasmic extract was prepared using 1% Triton X-100 and applied to Ni-NTA column. After washing the column with 20 mM imidazole, HcEGFR was eluted with 250 mM imidazole (in 50 mM Na$_2$HPO$_4$, pH 8.0, 300 mM NaCl). Fractions collected were dialyzed against 10 mM HEPES, pH 7.0, 50 mM NaCl, 10% glycerol, 1 ug/mL antipain and leupeptin and 0.1 mM Pefabloc SC. The protein was frozen in dry ice/methanol and stored −70° C.

Test compounds were made into 10 mg/m stock solutions in 100% dimethylsulfoxide (DMSO). Prior to experiment, stock solutions were diluted to 500 uM with 100% DMSO and then serially diluted to the desired concentration with HEPES buffer (30 mM HEPES pH 7.4).

For the enzyme reaction, 10 uL of each inhibitor (at various concentrations) were added to each well of a 96-well plate. To this was added 3 uL of enzyme (1:10 dilution in 10 mM HEPES, pH 7.4 for final conc. of 1:120). This was allowed to sit for 10 min on ice and was followed by the addition of 5 ul peptide (80 uM final conc.), ~10 ul of 4x Buffer (Table A), 0.25 uL $^{33}$P-ATP and 12 uL H$_2$O. The reaction was allowed to run for 90 min at room temperature and was followed by spotting the entire volume on to precut P81 filter papers. The filter discs were washed 2x with 0.5% phosphoric acid and radioactivity was measured using a liquid scintillation counter.

TABLE A

| Reagent | Final | 100 Rxns |
| --- | --- | --- |
| 1 M HEPES (pH 7.4) | 12.5 mM | 50 uL |
| 10 mM Na$_3$VO$_4$ | 50 uM | 20 uL |
| 1 M MnCl$_2$ | 10 mM | 40 uL |
| 1 mM ATP | 20 uM | 80 uL |
| $^{33}$P-ATP | 2.5 uCi | 25 uL |

The inhibition data for representative compounds of the invention are shown below in TABLE 1. The IC$_{50}$ is the concentration of test compound needed to reduce the total amount of phosphorylated substrate by 50%. The % inhibition of the test compound was determined for at least three different concentrations and the IC$_{50}$ value was evaluated from the dose response curve. The % inhibition was evaluated with the following formula:

% inhibition=100-[CPM(drug)/CPM(control)]×100 where CPM(drug) is in units of counts per minute and is a number expressing the amount of radiolabeled ATP ($\gamma$-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabeled ATP ($\gamma$-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction; Where it was possible to determine an, IC$_{50}$ value, this is reported in TABLE 1 otherwise the % inhibition at 0.5 $\mu$M concentration of test compound is shown in TABLE 1.

TABLE 1

Inhibition of EGF-R Kinase (recombinant enzyme)

| Example | IC50($\mu$M) | % Inhibition @ 0.5 ($\mu$M) |
| --- | --- | --- |
| 21 | 0.003 | |
| 22 | 0.05 | |
| 23 | 0.007 | |
| 24 | 0.1 | |
| 25 | 0.1 | |
| 27 | >0.1 | |
| 30 | 0.8 | 47% |
| 35 | >10 | 9% |
| 43 | 1 | 37.1% |
| 44 | 1 | 25.4% |
| 57 | 0.008 | |
| 58 | >0.1 | |
| 59 | 0.0007 | |
| 61 | 0.02 | |
| 62 | 0.005 | 97.4% |
| 63 | 1 | |
| 64 | 0.006 | |
| 74 | 1 | 31.3% |

Inhibition of Epithelial Cell Kinase (ECK)

In this standard pharmacological test procedure, a biotinylated peptide substrate is first immobilized on neutravidin-coated microtiter plates. The test drug, the Epithelial Cell Kinase (ECK), Mg$^{++}$, sodium vanadate (a protein tyrosine phosphatase inhibitor), and an appropriate buffer to maintain pH (7.2) are then added to the immobilized substrate-containing microtiter wells. ATP is then added to initiate phosphorylation. After incubation, the assay plates are washed with a suitable buffer leaving behind phosphorylated peptide which is exposed to horse radish peroxidase (HRP)-conjugated anti-phosphotyrosine monoclonal antibody. The antibody-treated plates are washed again and the HRP activity in individual wells is quantified as a reflection of degree of substrate phosphorylation. This nonradioactive format was used to identify inhibitors of ECK tyrosine kinase activity where the IC$_{50}$ is the concentration of drug that inhibits substrate phosphorylation by 50%. The results obtained for representative compounds of this invention are listed in TABLE 2. Multiple entries for a given compound indication it was tested multiple times.

TABLE 2

Inhibition of Epithelial Cell Kinase (Eck)

| Example | IC50 ($\mu$M) |
| --- | --- |
| 24 | <.04 |
| 24 | .03 |
| 43 | >2.3 |
| 44 | >2.1 |
| 66 | >3.3 |
| 69 | >3.1 |
| 77 | >2.4 |

Inhibition of Kinase Insert Domain Containing Receptor (KDR; the Catalytic Domain of the VEGF Receptor)

In this standard pharmacological test procedure, KDR protein is mixed, in the presence or absence of an inhibitor compound, with a substrate peptide to be phosphorylated (a copolymer of glutaric acid and tyrosine, E:Y=4:1) and other cofactors such as Mg$^{++}$ and sodium vanadate (a protein tyrosine phosphatase inhibitor) in an appropriate buffer to maintain pH (7.2). ATP and a radioactive tracer (either P$^{32}$- or P$^{33}$-labeled ATP) is then add to initiate phosphorylation. After incubation, the radioactive phosphate associated with the acid-insoluble fraction of the assay mixture is then quantified as reflection of substrate phosphorylation. This radioactive format was used to identify inhibitors of KDR tyrosine kinase activity where the IC$_{50}$ is the concentration of drug that inhibits substrate phosphorylation by 50%. As an example, the compound of Example 66 inhibits KDR with an IC$_{50}$ of 33.9 $\mu$g/ml.

Mitogen Activated Protein Kinase (MAPK) Assay

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, was used. Recombinant human MEK 1 (MAPKK) was first used to activate recombinant human ERK2 (MAPK) and the activated MAPK (ERK) was incubated with substrate (MEP peptide or MYC peptide) in the presence of ATP, Mg$^{+2}$ and radiolabeled $^{33}$P ATP. The phosphorylated peptide was captured on a P 81 phosphocellulose filter (paper filter or embedded in microtiter plate) washed and counted by scintillation methods.

The peptide substrates used in the assay are MBP, peptide substrate (APRTPGGRR), or synthetic Myc substrate, (KKFELLPTPPLSPSRR•5 TFA. The recombinant enzymes used were prepared as GST fusion proteins of human ERK 2 and human MEK 1. Inhibitor samples were prepared as 10× stocks in 10% DMSO and an appropriate aliquot was used to deliver either 10 ug/ml for a single point screening dose or 100, 10, 1, and 0.1 uM final concentration for a dose response curve. Final DMSO concentrations were less than or equal to 1%.

The reaction was run as follows in 50 mM Tris kinase buffer, pH 7.4 in a reaction volume of 50 ul. The appropriate volume of kinase buffer and inhibitor sample was added to the tube. Appropriate dilution of enzyme was delivered to give 2–5 ug recombinant MAPK (Erk) per tube. The inhibitor was incubated with MAPK (Erk) for 30 min at 0 deg. C. Recombinant Mek (MAPKK) (0.5–2.5 ug) or fully activated Mek (0.05–0.1 units) was added to activate the Erk and incubated for 30 min at 30° C. Then substrate and gamma $^{33}$P ATP was were added to give a final concentration of 0.5–1 mM MBPP or 250–500 uM Myc; 0.2–0.5 uCi gamma $^{33}$P ATP/tube; 50 μM ATP final concentration. Samples were incubated at 30° C. for 30 minutes and the reaction was stopped by adding 25 μl of ice cold 10% TCA. After samples were chilled on ice for 30 min, 20 μl of sample was transferred onto P 81 phosphocellulose filter paper or, appropriate MTP with embedded P 81 filter. Filter papers or MTP were washed 2 times with a large volume of 1% acetic acid, then 2 times with water. The filters or MTP were briefly air dried before addition of scintillant and samples were counted in the appropriate scintillation counter set up for reading $^{33}$P isotope. Samples included a positive control (activated enzyme plus substrate); a no enzyme control; a no substrate control; samples with different concentrations of putative inhibitor; and samples with reference inhibitors (other active compounds or non-specific inhibitors such as staurosporine or K252 B).

The raw data was captured as cpm Sample replicates were averaged and corrected for background count. Mean cpm data was tabulated by group and % inhibition by a test compound was calculated as (corrected cpm control-corrected. cpm sample/control)×100=% inhibition. If several concentrations of inhibitor were tested, IC$_{50}$ values (the concentration which gives 50% inhibition) were determined graphically from the dose response curve for % inhibition or by an appropriate computer program The results obtained for representative compounds of this invention are listed in TABLE 3 where there may be separate entries for the same compound; this is an indication that the compound was evaluated more than one time.

TABLE 3

Inhibition of Mitogen Activated Protein Kinase (Mek-Erk)

| Example | IC50 (μM) |
|---|---|
| 21 | >100 |
| 21 | 10 |
| 21 | >50 |
| 22 | >100 |
| 22 | >100 |
| 23 | >100 |
| 23 | 100 |
| 24 | >100 |
| 24 | >100 |
| 25 | >100 |
| 25 | 8 |
| 25 | 50 |
| 26 | >100 |
| 27 | >100 |
| 27 | >100 |
| 28 | 6 |
| 30 | 50 |
| 35 | >100 |
| 37 | >100 |
| 43 | >100 |
| 44 | >100 |
| 49 | 25 |
| 49 | 25 |
| 57 | >100 |
| 58 | >100 |

Inhibition of Cancer Cell Growth as Measured by Cell Number

Human tumor cell lines were plated in 96-well plates (250 μl/well, 1–6×10$^4$ cells/ml) in RPMI 1640 medium, containing 5% FBS (Fetal Bovine Serum). Twenty four hours after plating, test compounds were added at five log concentrations (0.01–100 mg/ml) or at lower concentrations for the more potent compounds. After 48 hours exposure to test compounds, cells were fixed with trichloroacetic acid, and stained with Sulforhodamine B. After washing with trichloroacetic acid, bound dye was solubilized in 10 mM Tris base and optical density was determined using a plate reader. Under conditions of the assay the optical density is proportional to the number of cells in the well. IC$_{50}$s (concentrations causing 50% inhibition of cell growth) were determined from the growth inhibition plots. The test procedure is described in details by Philip Skehan et. at *J. Natl. Canc. Inst.*, 82, 1107–1112 (1990). These data are shown below in TABLE 4. Information about some of the cell lines used in these test procedures is available from the American Type Tissue Collection: Cell Lines and Hybridomas, 1994 Reference Guide, 8th Edition. The Her2Neu cell line is a 3T3 line that has bbeen transfected with Her2 receptor kinase.

TABLE 4

Inhibition of Cancer Cell Growth as Measured by Cell Number (IC$_{50}$ μg/mL)

| Ex. | MDA435 | A431 | SKBR3 | A2780S | A2780DDP | SW620 | LOX | MCF7 | 3T3 | Her2Neu |
|---|---|---|---|---|---|---|---|---|---|---|
| 30 | >5 | 2.761 | 4.826 | 1.771 | 4.002 | >5 | | | | |
| 57 | >5 | 3.918 | >5 | 3.33 | >5 | >5 | | | | |
| 58 | 2.4 | 0.4 | 2.9 | 1.0 | 1.8 | 4.1 | | | | |

TABLE 4-continued

Inhibition of Cancer Cell Growth as Measured by Cell Number (IC$_{50}$ µg/mL)

| Ex. | MDA435 | A431 | SKBR3 | A2780S | A2780DDP | SW620 | LOX | MCF7 | 3T3 | Her2Neu |
|-----|--------|------|-------|--------|----------|-------|-----|------|-----|---------|
| 59 | >5 | 0.4 | 4.1 | 3.5 | 3.1 | >5 | | | | |
| 61 | 0.88 | 0.23 | 0.12 | 0.06 | 0.13 | 0.17 | 0.07 | 0.40 | | |
| 62 | | | | | | | | | 0.373 | 0.106 |
| 62 | 0.4635 | 0.08798 | 0.03565 | | | 0.356 | | | 0.2716 | 0.04359 |
| 63 | 49 | 0.5 | 0.4 | 0.5 | 0.8 | 41 | 57 | | | |
| 64 | 0.98 | 0.31 | | 0.74 | 0.43 | | 3.60 | 3.87 | | |
| 64 | 3.942 | 0.209 | 1.876 | 2.363 | 2.246 | 4.621 | | | | |
| 65 | 47 | 59 | 41 | 31 | 52 | 42 | 56 | | | |
| 74 | >5 | 2.228 | 4.633 | | | >5 | | | 4.479 | >5 |
| 85 | 4.203 | 3.056 | 3.591 | 2.344 | 2.969 | 4.724 | | | | |

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. The compounds of this invention are also useful in treating, inhibiting the growth of, or eradicating neoplasms of the breast that express the receptor protein produced by the erbB2 (Her2) oncogene. Additionally, the compounds of this invention are useful in treating or inhibiting polycystic kidney disease and colonic polyps.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The following representative examples show the preparation of the compounds of this invention.

EXAMPLE 1

4-Chloro-but-2-ynoic Acid

Propargyl chloride (2 mL, 26.84 mmol) was dissolved in 40 mL of tetrahydrofuran under nitrogen and cooled to −78° C. After addition of n-butyllithium (5.4 mL, 13.42 mmol, 2.5 M in n-hexane) and stirring for 15 min, a stream of dry carbon dioxide was passed through it at −78° C. for two hours. The reaction solution was filtered and neutralized with 3.5 mL of 10% sulfuric acid. After evaporation of the solution, the residue was extracted with ether. The ether solution was washed with saturated brine solution, and dried over sodium sulfate. After evaporation of the dry ether solution, 0.957 g (60%) of an product was obtained as an oil: ESMS m/z 116.6 (M−H$^+$).

EXAMPLE 2

4-Dimethylamino-but-2-ynoic Acid n-Butyl lithium in hexane (96 mL, 2.5 M in n-hexane) was slowly added to 1-dimethylamino-2-propyne (20 g, 240 mmol) in 100 mL of tetrahydrofuran under nitrogen. The mixture was stirred for 1 h at −78° C., then dry carbon dioxide was pass through the reaction overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15.6 g of 4-dimethylamino-but-2-ynoic acid: mass spectrum (m/e):M−H 126.

EXAMPLE 3

Bis-(2-methoxy-ethyl)-prop-2-ynyl-amine

Propargyl bromide (17.8 g, 150 mmol) was added dropwise to a mixture of bis(2-methoxyethyl)amine (20 g, 150 mmol) and cesium carbonate (49 g, 150 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 20 g of bis-(2-methoxy-ethyl)-prop-2-ynyl-amine: mass spectrum (m/e): M+H 172.

EXAMPLE 4

4-[Bis-(2-methoxy-ethyl)-amino]-but-2-ynoic Acid n-Butyl lithium in hexane (42 mL, 2.5 M in n-hexane) was slowly added to bis-(2-methoxy-ethyl)-prop-2-ynyl-amine (18 g, 105 mmol) in 80 mL of tetrahydrofuran under nitrogen. The mixture was stirred for 1 h at −78° C., then dry carbon dioxide was passed through the reaction overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 18 g of 4-[bis-(2-methoxyethyl)-amino]-but-2-ynoic acid: mass spectrum (m/e):M−H 214.

EXAMPLE 5

1-Methyl-4-prop-2-ynyl-piperazine

Propargyl bromide (23.8 g, 200 mmol) was added dropwise to a mixture of 1-methyl-piperazine (20 g, 200 mmol) and cesium carbonate (65 g, 200 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 7.5 g of 1-methyl-4-prop-2-ynyl-piperazine: mass spectrum (m/e): M+H 139.

EXAMPLE 6

4-(4-Methyl-piperazin-1-yl)-but-2-ynoic Acid n-Butyl lithium in hexane (17.2 mL, 2.5 M in n-hexane) was slowly added to 1-methyl-4-prop-2-ynyl-piperazine (6.0 g, 43.5 mmol) in 40 mL of tetrahydrofuran under nitrogen. The mixture was stirred for 1 hr at −78 C., then dry carbon dioxide was passed through the reaction overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 7 g of 4-(4-methyl-piperazin-1-yl)-but-2-ynoic acid: mass spectrum (m/e):M−H 181.

EXAMPLE 7

(2-Methoxy-ethyl)-methyl-prop-2-ynyl-amine

Propargyl bromide (26.8 g, 225 mmol) was added dropwise to a mixture of N-(2-methoxyethyl)methyl amine (20 g, 225 mmol) and cesium carbonate (73 g, 225 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 14 g of (2-methoxy-ethyl)-methyl-prop-2-ynyl-amine: mass spectrum (m/e): M+H 127.

EXAMPLE 8

4-[(2-Methoxy-ethyl)-methyl-amino]-but-2-ynoic Acid n-Butyl lithium in hexane (37.8 mL, 2.5 M in n-hexane) was slowly added to (2-methoxy-ethyl)-methyl-prop-2-ynyl-amine (12.0 g, 94.5 mmol) in 90 mL of tetrahydrofuran under nitrogen. The mixture was stirred for 1 hr at −78° C., then dry carbon dioxide was passed through the reaction overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 15 g of 4-[(2-methoxy-ethyl)-methyl-amino]-but-2-ynoic acid: mass spectrum (m/e): M−H 170.

EXAMPLE 9

Allyl-methyl-prop-2-ynyl-amine

Propargyl bromide (33.4 g, 281 mmol) was added dropwise to a mixture of isopropyl-methyl-amine (20 g, 281 mmol) and cesium carbonate (90 g, 281 mmol) in 350 mL of acetone. The mixture was stirred overnight under nitrogen at room temperature. The inorganic salts were then filtered off, and the solvent was removed. The residue was dissolved in saturated sodium bicarbonate solution and extracted with ethyl acetate. The organic extracts were then evaporated to give 4.6 g of allyl-methyl-prop-2-ynyl-amine: mass spectrum (m/e): M+H 110.

EXAMPLE 10

4-(Allyl-methyl-amino)-but-2-ynoic Acid n-Butyl lithium in hexane (16.4 mL, 2.5 M in n-hexane) was slowly added to allyl-methyl-prop-2-ynyl-amine (4.5 g, 46 mmol) in 50 mL of tetrahydrofuran under nitrogen. The mixture was stirred for 1 hr at −78° C., then dry carbon dioxide was passed through the reaction overnight. The resulting solution was poured into water and washed with ethyl acetate. The aqueous layer was evaporated under reduced pressure to give the crude acid. The dry acid was dissolved in methanol, and the insoluble salt was removed via filtration. The filtrate was collected and dried in vacuo to give 4.1 g of 4-(allyl-methyl-amino)-but-2-ynoic acid: mass spectrum (m/e): M−H 152.

EXAMPLE 11

4-Methoxymethoxy-but-2-ynoic Acid

To a suspension of 8.2 g of 60% sodium hydride in mineral oil in 271 mL of tetrahydrofuran at 0° C. with stirring under nitrogen was added dropwise 10 g of propargyl alcohol over 15 min. The mixture was stirred an additional 30 min. To the stirred mixture at 0° C was added 15.8 g of chloromethylmethyl ether. Stirring was continued at room temperature over night. The mixture was filtered and the solvent was removed from the filtrate. The residue was distilled (35–38° C., 4 mm) giving 8.5 g. of a liquid. The distillate was dissolved in 200 mL of ether. The solution was stirred under nitrogen and cooled to −78° C. as 34.1 mL of 2.5 molar n-butyl lithium in hexanes was added over 15 min. Stirring was continued for another 1.5 hr. Dry carbon dioxide was passed over the surface of the stirring reaction mixture as it warmed from −78° C. to room temperature. The mixture was stirred under a carbon dioxide atmosphere over night. The mixture was poured into a mixture of 14 mL of hydrochloric acid and 24 mL of water. The organic layer was separated and dried over magnesium sulfate. The solvent was removed and the residue was maintained at 100° C. at 4 mm for 1 hr giving 10.4 g of 4-methoxymethoxy-but-2-ynoic acid.

EXAMPLE 12

4-Bromo Crotonic Acid

Using the method of Braun [Giza Braun, J. Am. Chem. Soc. 52, 3167 (1930)], 11.76 mL (17.9 grams 0.1 moles) of methyl 4-bromo crotonate in 32 mL of ethanol and 93 mL of water was cooled to −11° C. The reaction was stirred vigorously, and 15.77 g (0.05 moles) of finely powdered barium hydroxide was added portionwise over a period of about an hour. Cooling and vigorous stirring were continued for about 16 hours. The reaction mixture was then extracted with 100 mL of ether. The aqueous layer was treated with 2.67 mL (4.91 g; 0.05 moles) of concentrated sulfuric acid. The resulting mixture was extracted with three 100 mL portions of ether. The combined ethereal extracts were washed with 50 mL of brine, then dried over sodium sulfate. The solution was taken to an oil in vacuo . This oil was taken up in about 400 mL of boiling heptane, leaving a gum. The heptane solution was separated and boiled down to about 50 mL. Cooling gave 3.46 g of product.

EXAMPLE 13

4-(2-Methoxy-ethoxy)-but-2-ynoic Acid

To a suspension of 6.04 g (151 mmol) of 60% sodium hydride in 200 ml of tetrahydrofuran at 0° C. was add 10 g (131,4 mmol) of 2-methoxyethanol dropwise. over 15 min. After 1 hr, 19.54 g (131.4 mmol) of 80% propargyl bromide was added dropwise. After stirring 17 hr at room temperature, the mixture was filtered and the solvent was removed. The residue was distilled (48–51° C., 4 mm) to give 11.4 g of a colorless liquid. This was dissolved in 250 ml of ether and cooled to −78° C. with stirring under nitrogen. To this solution was added 39.95 ml (99.9 mmol) of 2.5 M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 100 ml of 3N hydrochloric acid and solid sodium chloride. The organic layer was separated and dried over magnesium sulfate. The solvent was removed and the residue was maintained under vacuum giving 11.4 g of the title compound.: mass spectrum (electrospray, m/e, negative mode): M−H 156.8.

EXAMPLE 14

4-(Methoxymethoxy)-but-2-ynoic Acid

To a suspension of 8.2 g (205 mmol) of 60% sodium hydride in 271 ml of tetrahydrofuran was added dropwise at 0° C. with stirring 10.0 g (178.4 mmol) of propargyl alcohol. After 30 min, 15.8 g (196.2 mmol) of chloromethylmethyl ether was added. After stirring over the weekend at room temperature, the mixture was filtered and the solvent was remove. The residue was distilled (35–38° C., 4 mm) to give 8.54 g of a colorless liquid. This was dissolved in 200 ml of ether and cooled to −78° C. with stirring under nitrogen. To this solution was added 34.1 ml (85.3 mmol) of 2.5 M n-butyl lithium solution in hexanes dropwise over 15 min. After 1.5 hr, dry carbon dioxide was bubbled in as the mixture slowly warmed to room temperature. The mixture was maintained in a carbon dioxide atmosphere overnight. To the mixture was added 14 ml of hydrochloric acid in 24 ml water. The organic layer was separated and dried over magnesium sulfate. The solvent was removed and the residue was maintained under vacuum giving 10.4 g of the title compound as a liquid.

EXAMPLE 15

4-((2S)-2-methoxymethylpyrrolidin-1-yl)butynoic Acid n-Butyllithium solution in hexane (35.9 mmol) was added over 10 min to a solution of 5.49 g (35.9 mmol) of (2S)-2-methoxymethyl-1-prop-2-ynylpyrrolidine in 100 mL of THF at −78° C. under $N_2$. After stirring cold for 1 hr, $CO_2$ was bubbled into the solution as it slowly came to 25° C. After stirring overnight, 100 mL of water was added, the reaction was extracted with ethyl acetate and the extracts were discarded. The reaction was adjusted to pH 7 with 20% $H_2SO_4$ and solvent was removed. The residue was slurried with methanol and filtered. The filtrate was evaporated and dried in vacuo to give 7.06 g of 4-((2S)-2-methoxymethylpyrrolidin-1-yl)butynoic acid as a brown foam: mass spectrum (electrospray, m/e): M+H 198.0.

EXAMPLE 16

(2S)-2-Methoxymethyl-1-prop-2-ynylpyrrolidine

A mixture of 4.82 g (41.9 mmol) of S-2-(methoxymethyl) pyrrolidine, 13.7 g (41.9 mmol) of cesium carbonate and 5.00 g (41.9 mmol) of propargyl bromide in 80 mL of acetone was stirred at 25° C. overnight. The reaction was filtered and solvent was removed from the filtrate. The residue was diluted with a small amount of water and saturated $NaHCO_3$ and extracted with ether. The extract was treated with activated charcoal, dried and evaporated to give 5.93 g of (2S)-2-methoxymethyl-1-prop-2-ynylpyrrolidine as a yellow orange oil: mass spectrum (electrospray, m/e): M+H 153.8.

EXAMPLE 17

4-(1,4-Dioxa-8-azaspiro[4,5]dec-8-yl)but-2-ynoic Acid n-Butyllithium in hexane (55.8 mmol) was added dropwise to a solution of 10.1 g (55.8 mmol) of 3-(1,4-dioxa-8-azaspiro[4,5]dec-8-yl)but-2-yne in 185 mL of THF at −78° C. under $N_2$. After stirring at −78° C. for 1 h, $CO_2$ was bubbled into the solution as it slowly came to 25° C. After stirring overnight, the reaction was diluted with 150 mL of water, extracted with ethyl acetate and the extracts were discarded. The solution was adjusted to pH 6 with 2 M sulfuric acid and evaporated. The residue was slurried with methanol and filtered. The filtrate was evaporated and dried in vacuo to give 4.5 g of 4-(1,4-dioxa-8-azaspiro[4,5]dec-8-yl)but-2-ynoic acid as a brown amorphous solid: mass spectrum electrospray, m/e): M+H 225.8.

EXAMPLE 18

3-(1,4-Dioxa-8-azaspiro[4,5]dec-8-yl)but-2-yne

A mixture of 10.0 g (69.9 mmol) of 1,4-dioxa-8-azaspiro[4,5]decane, 22.8 g (69.9 mmol) of cesium carbonate and 8.32 g (69.9 mmol) of propargyl bromide in 165 mL of acetone was stirred overnight at 25° C. The reaction was filtered and the filtrate was evaporated to dryness. A small amount of water and saturated $NaHCO_3$ was added to the residue and it was extracted with ether. The ethereal extracts were treated with activated charcoal, dried and evaporated to give 10.8 g of 3-(1,4-dioxa-8-azaspiro[4,5]dec-8-yl)but-2-yne as a yellow orange oil: mass spectrum (electrospray, m/e): M+H 181.8.

EXAMPLE 19

2-(2-Chloro-5-nitro-pyridine-3-carbonyl)-3-dimethylamino-acrylonitrile

A solution of 10.6 g (52.5 mmol) of 3-carboxy-2-chloro-5-nitro pyridine (J. Med. Chem. 1895, 1992) and 8.86 g (69.8 mmol) of oxalyl chloride was stirred in 200 ml of methylene chloride. About 0.2 ml of N,N-dimethylformamide was added and the mixture was stirred for 5.5 hr. Solvent is removed and the resulting acid chloride was used without additional purification. The acid chloride was dissolved in 163 ml of methylene chloride containing 5.55 g (55.5 mmol) of 3-dimethylamine-acrylonitrile and 7.46 g (57.7 mmol) of diisopropylethyl amine. The solution was refluxed under nitrogen for 16 hr. The mixture was diluted with chloroform and washed with a saturated solution of sodium bicaronate. The organic layer was dried over magnesium sulfate and place on a column of silica gel. The product was eluted with a combination of chloroform and ether. Solvent was removed and the residue was treated with a mixture of ethyl acetate-hexane 1:1 at which time the mixture crystallized. The solid was collected giving 8.9 g of the title compound as an orange solid:: mass spectrum (chemical ionization, m/e): M+H 281.

EXAMPLE 19

6-Nitro-4-oxo-1,4-dihydro-[1,8]naphthyridine-3-carbonitrile

A solution of 22.4 g (79.8 mmol) of 2-(2-chloro-5-nitro-pyridine-3-carbonyl)-3-dimethylamino-acrylonitrile was refluxed in a mixture of 500 ml of ethanol and 180 ml of conc. ammonium hydroxide for 2 hr. The mixture was cooled and solid was collected which was washed with ether. Concentrating the filtrate gave a second crop which was collected and washed with ether. Solids were combined. After drying, 19.3 g of the title compound was obtained as a yellow solid: mass spectrum (electrospray, m/e): M−H 215 (negative mode).

EXAMPLE 20

4-Chloro-6-nitro-[1,8]naphthyridine-3-carbonitrile

A mixture of 19.3 g (89.3 mmol) of 6-nitro-4-oxo-1,4-dihydro-[1.8]naphthyridine-3-carbonitrile in 386 ml of phosphorous oxychloride was refluxed for 24 hr. Excess phosphorous oxychloride was removed. The residue is mixed with ethyl acetate and 15 g of potassium hydroxide in 200 ml of ice water. The organic layer was separated and the aqueous layer was extract several more times with ethyl acetate. The combined volume of extracts was 4000 ml. The extracts were dried of magnesium sulfate and the solution was filter through a short silica gel column. The solvent was removed. The residue was stirred with ether and the solid was collected giving 15.7 g of the title compound as an orange solid: mass spectrum (electrospray, m/e): M+H 235.

EXAMPLE 21

4-(3-Bromo-phenylamino)-6-nitro-[1,8]naphthyridine-3-carbonitrile

A mixture of 7.5 g (32 mmol) of 4-chloro-6-nitro-[1.8]naphthyridine-3-carbonitrile and 5.5 g (32 mmol) of 3-bromo-aniline in 175 ml of isopropanol was stirred at reflux for 2 hr. and 45 min. The mixture was cooled, solid was collected, and washed with ether giving 12.9 g of the title compound as the yellow hydrochloride salt: mass spectrum (electrospray, m/e): M+H 370, 373.

EXAMPLE 22

6-Amino-4-(3-bromo-phenylamino)-[1,8]naphthyridine-3-carbonitrile

A mixture of 11.2 g (30.3 mmol) of 4-(3-bromo-phenylamino)-6-nitro-[1.8]naphthyridine-3-carbonitrile, 5.1 g (90.8 mmol) of powdered iron, and 8.1 g (151 mmol) of ammonium chloride was mechanically stirred at reflux in a mixture of 330 ml water and 560 ml methanol for 40 min. The liquid layer was decanted from the solids and diluted with ethyl acetate, saturated sodium bicarbonate, and brine. This mixture was extract multiple times with ethyl acetate (final volume 3500 ml). The combined extracts were dried with magnesium sulfate and filter through a short column of silica gel. The solvent was removed and the residue was stirred with ether. The solid was collected and dried give 8.04 g of the title compound as an orange solid: mass spectrum (electrospray, m/e): M+H 340, 342.1.

EXAMPLE 23

N-[5-(3-Bromo-phenylamino)-6-cyano-[1,8]naphthyridin-3-yl]-acrylamide

To a solution of 1.4 g (4.12 mmol) of 6-amino-4-(3-bromo-phenylamino)-[1.8]naphthyridine-3-carbonitrile and 1.67 g (16.5 mmol) of N-methyl-morpholine in a mixture of 6 ml of N,N-dimethylformamide and 35 ml of tetrahydrofuran was added with stirring at 0° C. a solution of 0.52 g (5.76 mmol) of acryloyl chloride in 10 ml of tetrahydrofuran over 10 min. After 3 hr at 0° C., the most of the solvent was removed saturated sodium bicarbonate was added. Solid was collected and washed with water. After air drying, the solid was extracted with 500 ml of boiling tetrahydrofuran. The tetrahydrofuran was removed and the residue was purified on a silica gel column eluting with ethyl acetate-methanol mixtures giving 0.29 g of the title compound as a yellow solid: mass spectrum (electrospray, m/e): M+H 394, 396.

EXAMPLE 24

But-2-ynoic Acid [5-(3-bromo-phenylamino)-6-cyano-[1,8]-naphthyridin-3-yl]-amide To a solution of 0.85 g (10.1 mmol) of tetrolic acid and 1.8 g (17.96 mmol) of N-methyl morpholine in 18 ml of tetrahydrofuran was stirred at 0° C. as 1.35 g (9.9 mmol) of isobutyl chloroformate was slowly added. After 15 min, this mixture was added to a solution of 1.3 g (3.8 mmol) of 6-amino-4-(3-bromo-phenylamino)-[1.8]naphthyridine-3-carbonitrile and 5 mg of 4-N,N-dimethylamino-pyridine in 10 ml pyridine. The mixture was stirred a room temperature for 2.25 hr. The tetrahydrofuran was removed, diluted sodium bicarbonate was added, and the solid was collected via filtration. The solid was air dried and chromatographed on silica gel eluting with ethyl acetate-methanol mixtures giving 0.46 g of the title compound as a tan powder: mass spectrum (electrospray, m/e): M+H 408.1, 406.0.

EXAMPLE 25

4-(3-Chloro-4-fluoro-phenylamino)-6-nitro-r[1,8]naphthyridine-3-carbonitrile

By using the method of Example 21, 2.5 g (10.66 mmol) of 4-chloro-6-nitro-[1.8]naphthyridine-3-carbonitrile and 1.55 g (10.66 mmol) of 3-chloro-4-fluoro-aniline was converted to 3.51 g of the title compound, a yellow solid, as its hydrochloride salt: mass spectrum (electrospray, m/e): M+H 344.1.

EXAMPLE 26

6-Amino-4-(3-chloro-4-fluoro-phenylamino)-[1,8]naphthyridine-3-carbonitrile

By using the method of Example 22, 3.2 g (8.4 mmol) of 4-(3-chloro-4-fluoro-phenylamino)-6-nitro-[1.8]naphthyridine-3-carbonitrile was reduced to give 2.07 g of the title compound as an tan powder.

EXAMPLE 27

But-2-ynoic acid [5-(3-chloro-4-fluoro-phenylamino)-6-cyano-[1,8]naphthyridin-3-yl]-amide By using the method of Example 24, 0.8 g (2.55 mmol) of 6-amino-4-(3-chloro-4-fluoro-phenylamino)-[1.8]naphthyridine-3-carbonitrile was converted to 0.5 g of the title compound as a brown solid: mass spectrum (electrospray, m/e): M+H 380.1.

EXAMPLE 28

N-[5-(3-Bromo-phenylamino)-6-cyano-[1,8]naphthyridin-3-yl]-2-chloro-acetamide

To a solution of 0.74 g (2.2 mmol) of 6-amino-4-(3-bromo-phenylamino)-[1.8]naphthyridine-3-carbonitrile and 0.7 g (5.44 mmol) of disopropylethyl amine in a 7 ml of N-methylpyrrolidone was added with stirring at 0° C. a solution of 0.29 g (2.6 mmol) of chloroacetyl chloride in 5 ml of tetrahydrofuran over 5 min. After 1 hr at 0° C. the mixture was warmed to room temperature. The mixture was poured into saturated sodium bicarbonate. Solid was collected and air dried. The solid was purified by chromatography on silica gel eluting with ethyl acetate-methanol mixtures giving 0.7 g of the title compound as a tan solid: mass spectrum (electrospray, m/e): M+H 416.1, 418.1.

EXAMPLE 29

4-Bromo-2-butenoyl Chloride

To a stirred solution of 123.9 g (522 mmol) trimethylsilyl-4-bromo-2-butenoate (Synthesis 745, 1983) and 72.9 g (50.3 ml, 676 mmol) of oxalyl chloride was added 7 drops of DMF. There is a very rapid gas evolution. The mixture is stirred a total of 4 hrs. The solvent is removed. The product was distilled at 0.4 mm . The fraction distilling at 60–62° C. is collected giving 79.8 g of the title compound as a pale yellow liquid.

EXAMPLE 30

4-Dimethylamino-but-2-enoic acid [5-(3-bromo-phenylamino)-6-cyano-[1,8]naphthyridin-3-yl]-amide To a suspension of 2.5 g (7.35 mmol) of 6-amino-4-(3-bromo-phenylamino)-[1.8]naphthyridine-3-carbonitrile and 0.95 g (7.35 mmol) of disopropylethyl amine in 40 ml tetrahydrofuran at 0° C. , with stirring, was added 1.42 g (7.72 mmol) of 4-bromo-2-butenoyl chloride followed by 5 ml of N-methyl pyrrolidone. After 1 hr, 55 ml of 2M dimethylamine in tetrahydrofuran was added. After 30 min, the solvents were removed. The mixture was mixed with ethyl acetate and saturated sodium bicarbonate. The organic layer was dried over magnesium sulfate and the solvent was removed. The product was purified by chromatography on silica gel eluting first with ethyl acetate-methanol 9:1 to remove less polar impurities and then with acetate-methanol-triethyl amine 40:10:1 to elute 0.49 g of the product which was obtained as and orange powder: mass spectrum (electrospray, m/e): M+H 450.9,453.0; (M+2H)+2 226.7, 225.8.

EXAMPLE 31

2-Ethoxy-5-nitropyridine

To anhydrous ethanol (250 ml) were added sodium (2.25 g, 97.8 mmol) then 2-chloro-5-nitropyridine (15 g, 9.46 mmol) under argon. The resulting mixture was heated at reflux for 10 hrs. After cooling slightly, the mixture was filtered to remove undissolved particles. The filtrate was condensed by rotary evaporation. The residue was triturated with abs ethanol (50 ml). The solid was collected by filtration and dried giving 13.5 g of the product: mp 90–92° C. mass spectrum (electrospray, m/e): 169 (M+H); IR cm-1: 1600, 1508, 1378, 1290, 1118, 1027; H-NMR δ (CDCl$_3$) 1.431 (3H, t, CH$_3$), 4.512 (2H, q, CH$_2$), 6.800 (1H, d, C3-H), 8.337 (1H, dd, C4-H), 9.068 (1H, d, C5-H). See: Friedman et. al., *J. Amer. Che. Soc.,* 69, 1947, 1204.

EXAMPLE 32

2-Cyano-3-(6-ethoxy-pyridin-3-ylamino)-acrylic Acid Ethyl Ester

Hydrogenation of 2-ethoxy-5-nitropyridine (6.2 g, 36.9 mmol) with 10% Pd/C (500 mg) in abs MeOH (350 ml) at atmospheric pressure gave 2-ethoxy-5-aminopyridine in an quantitative yield. The product was pure (TLC, NMR), therefore was used for the next step without further purification. 2-Ethoxy-5-aminopyridine was heated at reflux with ethyl(ethoxymethylene)cyanoacetate (12 g, 2 mole eq.) in toluene for 10 hrs. The reaction mixture was cooled, and the resulting solid was collected, which was pure on TLC and H-NMR. mass spectrum (electrospray, m/e): 262.0 (M+H); IR cm$^{-1}$: 2989, 2213, 1672, 1628, 1610; H-NMR δ (CDCl3): 1.235 (3H, t, CH$_3$), 1.304 (3H, t, CH$_3$), 4.166 (2H, q, CH$_2$), 4.274 (2H, q, CH$_2$), 6.815 (1H, d, C3-H), 7.760 and 7.880 (1H, d, d, cis and trans olefin H), 8.228 (1H, s, C2-H), 8.276 (1H, dd, C4-H), 10.:0 (1H, bs, NH).

EXAMPLE 33

6-Ethoxy-4-hydroxyl-[1,5]naphthyridine-3-carbonitrile

A sample of 2-cyano-3-(6-ethoxy-pyridin-3-ylamino)-acrylic acid ethyl ester was heated at 257–259° C. (internal temperature) in Dowtherm for 10–12 hrs under nitrogen. After cooling, the reaction mixture was poured into n-hexane. The black solid was collected, and treated with MeOH and CH$_2$Cl$_2$ mixture (1:5). The title compound (or tautomer) was collected and dried. mass spectrum (electrospray, m/e): 215.9 (M+H); IR cm-1: 3063, 2226; H-NMR δ (DMSO-d6): 1.355 (3H, t, CH$_3$), 4.412 (2H, q, CH$_2$), 7.244 (1H, d, C7-H), 7.983 (1H, d, C8-H), 8.682 (1H, s, C2-H), 10.50 (1H, bs, OH).

EXAMPLE 34

4-Chloro-6-ethoxy-[1,5]naphthyridine-3-carbonitrile

A solution of 6-ethoxy-4-hydroxyl-[1,5]naphthyridine-3-carbonitrile (500 mg, mmol) in POCl$_3$ was heated at reflux for 2 hrs under nitrogen. The temperature was reduced to 45–50° C. (bath) and heated at this temperature for an additional 2 hrs. After cooling, the solvent was removed by rotary evaporation. The residue was treated with a mixture of ice and water, made basic by using NH$_4$OH, and extracted with CH$_2$Cl$_2$. The combined extracts were washed (brine), dried (Na$_2$SO$_4$), and concentrated to give the title compound as a white solid (522 mg, 100%). H-NMR δ (DMSO-d$_6$): 1.437 (3H, t, CH$_3$), 4.572 (2H, q, CH$_2$), 7.495 (1H, d, C8-H), 8.407 (1H, d, C7-H), 9.108 (1H, s, C2-H).

EXAMPLE 35

4-(3-Bromo-phenylamino)-6-ethoxy-[1,5]naphthyridine-3-carbonitrile

4-Chloro-6-ethoxyl-[1,5]naphthyridine-3-carbonitrile (500 mg, 2.14 mmol) was heated at reflux with m-bromoaniline (0.69 ml, 3 eq) in the presence of pyridine HCl salt (250 mg, 1.1 eq) in ethoxyethanol (20 ml) under argon for 3 hrs. After cooling the mixture was diluted with water, made basic with NH$_4$OH, and extracted with CH$_2$Cl$_2$. The extracts were washed (Brine), dried (Na$_2$SO$_4$), and concentrated. The remaining solid was triturated with a mixture of CH$_2$Cl$_2$ and ether, giving the title compound as a yellow solid. mass spectrum (electrospray, m/e): 370.9 (M+H); IR cm-1: 3305, 2217; H-NMR δ (DMSO-d$_6$): 1.365 (3H, t, CH$_3$), 4.585 (2H, q, CH$_2$), 7.327 (1H, d, C8-H), 7.395 (2H, m, C4' and C6 Hs in bromoaniline), 7.503, (1H, m, C5'-H), 7.618 (1H, s, C2'-H), 8.194 (1H, d, C7-H), 8.516 (1H, s, C2-H), 9.684 (1H, bs, NH).

EXAMPLE 36

4-Hydroxyl-[1,5]naphthyridine-3-carbonitrile

3-Aminopyridine was heated at reflux with ethyl (ethoxymethylene)cyanoacetate (2 mole eq) in toluene for 10 hrs under argon. After cooling, the white solid was collected and dried. This material was heated at 255–257° C. in Dowtherm for 10 hrs. During this procedure ethanol was removed by distillation. After cooling, the reaction mixture was poured into a mixture of MeOH and CH$_2$Cl$_2$ (1:2) to remove non-polar material. The title compound was collected and dried. mass spectrum (electrospray, m/e): 171.8 (M+H).

EXAMPLE 37

4-(3-Bromophenylamino)-[1,5]naphthyridine-3-carbonitrile

A solution of 4-hydroxyl-[1.5]naphthyridine-3-carbonitrile (1.0 g, mmol) in 20 ml POCl$_3$ was refluxed for 3 hrs. After cooling, the solvent was removed by rotary evaporation. The residue was treated with ice-water mixture, made basic by NH$_4$OH, and extracted with CH$_2$Cl$_2$. Removal of the solvent gave 4-chloro-[1,5]naphthyridine-3-carbonitrile (285 mg, 28.5%). This was heated at reflux with 3-bromoaniline (3 eq) in the presence of pyridine HCl salt (350 mg) in ethoxyethanol for 3 hrs under argon. After cooling, the solvent was removed by rotary evaporation. The residue was partitioned between ice-water and ethyl acetate, made basic with (NH$_4$OH), extracted with ethyl acetate. The combined extracts were washed (brine) and dried (Na$_2$SO$_4$), and concentrated. The residue was triturated with ether. The title compound was collected and washed with ether, and dried. mass spectrum (electrospray, m/e): 326.9 (M+H); IR cm-1: 3372, 2209; H-NMR δ (DMSO-d$_6$): 7.36–7.90 (3H, m, C4' C5'-H and C6' Hs in bromoaniline), 7.64 (1H, s, C2'-H), 7.94 (1H, dd, C7-H), 8.36 (1H, dd, C8-H), 8.66 (1H, s, C2-H), 8.98 (1H, dd, C6-H), 10.47 (1H, bs, NH).

EXAMPLE 38

3-Morpholinopropanol

To a cooled (0° C., ice bath) solution of morpholine (31.5 ml, 0.36 mole) in toluene (300 ml) was added 3-bromopropanol (25 g, 0.18 mole) under argon. The cooling bath was then removed, the resulting mixture was warmed to room temperature, and stirred at room temperature for 1 hr. The mixture was heated at 100° C. (bath temperature) for 3 hrs under argon. After cooling, the mixture was diluted with ethyl acetate. The organic layer was washed (brine), dried (MgSO$_4$), and concentrated. The residue was chromatographed (silica gel, elution by 1:1 CH$_2$Cl$_2$-hexane) to give the title compound as a clear oil.

EXAMPLE 39

2-(3-Morpholin-4-yl-propoxy)-5-nitropyridine

To a cooled (0° C., ice bath) suspension of NaH (0.96 g, 20 mmol) in anhydrous tetrahydrofuran (100 ml) was added 3-morpholin-propanol (2.9 g, 20 mmol) under argon. This solution was stirred for an additional 1 hr. A solution of 2-chloro-5-nitropyridine (3.2 g, 20 mmol) in tetrahydrofuran (20 ml) was added all at once, and the resulting mixture was heated at reflux for 5 hrs under argon. After cooling, the solvent was removed by rotary evaporation, and the residue was dissolved in ethyl acetate. The ethyl acetate layer was washed (brine), dried (Na$_2$SO$_4$) and concentrated to dryness. The residue was chromatographed (flash column, silica gel, 10% ether in CH$_2$Cl$_2$) to give the title compound. mass spectrum (electrospray, m/e): 267.9 (M+H); IR cm-1: 2955, 1603, 1579, 1515; H-NMR δ (CDCl$_3$): 1.95–2.05 (2H, m), 2.46–2.54 (6H, m), 3.71–3.74 (4H, m), 4.489 (2H, t), 6.812 (1H, d, C3-H), 8.49 (1H, dd, C4-H), 9.065 (1H, d, C5-H).

EXAMPLE 40

2-Cyano-3-[6-(3-morpholin-4-yl-propoxy)-pyridin-3-ylamino]-acrylic Acid Ethyl Ester Hydrogenation of 2-(3-morpholin-4-yl-propoxy)-5-nitropyridine (10 g, 38.54 K mmol) with 10% Pd/C (MeOH) at room temperature under atmospheric pressure gave 2-(3-morpholin-4-yl-propoxy)-5-aminopyridine (9.2 g, 100%). This was heated at reflux with ethyl(ethoxymethylene)cyanoacetate (13.1 g, 77.4 mmol) in toluene for 8 hrs under argon. After cooling, the title compound, as a white solid, was collected and dried. (ca 50%). mass spectrum (electrospray, m/e): 361.0 (M+H); IR cm-1: 2214, 1704, 1637.

EXAMPLE 41

4-Hydroxy-6-(3-morpholin-4-yl-propoxy)-[1,5]naphthyridine-3-carbonitrile

A solution of 2-cyano-3-[6-(3-morpholin-4-yl-propoxy)-pyridin-3-ylamino]-acrylic acid ethyl ester (10 g) in Dowtherm (200 ml) was heated at 260° C. (internal temperature) under argon. During the first 8 hrs of heating, ethanol was removed through distillation head attached to apparatus. Then, the reaction mixture was heated at 260° C. for an additional S hrs. After cooling, the mixture was poured into hexanes. The solid was collected, and suspended in a mixture of $CH_2Cl_2$ and MeOH (ca 5:1). The black undissolved solid was removed, and the filtrate was diluted with ether. The yellowish brown solid was precipitated, collected, and dried to give the title compound mass spectrum (electrospray, m/e): 315.0 (M+H); IR cm-1: 2227, 1666, 1630; H-NMR δ (DMSO-$d_6$): 1.88–1.90 (2H, m), 2.26–2.29 (6H, m), 2.51 (2H, m), 3.49 (2H, m), 4.34 (2H, m), 6.852 (1H, d, C7-H), 8.147 (1H, d, C8-H) 8.715 (1H, s, C2-H), 11.2 (1H, bs, OH).

EXAMPLE 42

4-Chloro-6-(3-morpholin-4-yl-propoxy)-[1,5]naphthyridine-3-carbonitrile

To a suspension of 4-hydroxy-6-(3-morpholin-4-yl-propoxy)-[1.5]naphthyridine-3-carbonitrile in anhydrous $CH_2Cl_2$ (150 ml) was added oxalyl chloride (2.7 ml, 31.8 mmol) and DMF (0.1 ml, 20%) at room temperature under nitrogen. The suspension became a clear dark brown solution. The resulting mixture was stirred for an additional 1 hr. The solvent was removed by rotary evaporation. The residue was dissolved in ice-water mixture, made basic with ($NH_4OH$), and extracted with $CH_2Cl_2$. The extracts were washed (brine), dried ($Na_2SO_4$), and concentrated to give the title compound (400 mg, 38%). H-NMR δ (DMSO-$d_6$): 1.88 (2H, m), 2.26–2.29 (6H, m), 2.51 (2H, m), 3.49 (2H, m), 4.34 (2H, m), 6.834 (1H, d, C7-H), 8.147 (1H, d, C8-H), 8.711 (1H, s, C2-H).

EXAMPLE 43

4-(3-Hydroxy-4-methyl-phenylamino)-6-(3-morpholin-4-yl-propoxy)-[1,5]naphthyridine-3-carbonitrile A mixture of 4-chloro-6-(3-morpholin-4-yl-propoxy)-[1.5]naphthyridine-3-carbonitrile (400 mg, 1.202 mmol), 5-amino cresol (222 mg, 1.8 mmol) and pyridine HCl salt (208 mg, 1.8 mmol) in ethoxyethanol (20 ml) was heated at reflux for 6 hrs under argon. After cooling, the solvent was removed by rotary evaporation. The residue was dissolved in ethyl acetate and treated with sat $NaHCO_3$. The ethyl acetate layer was separated and the aqueous layer was extracted with ethyl acetate. The combined extracts were washed (sat $NaHCO_3$ aq sol, brine), dried ($Na_2SO_4$), and concentrated. The residue was triturated with $CH_2Cl_2$, and ether and hexane were added to form a solid. The yellow solid was collected (200 mg, 40%) and dried. mass spectrum (electrospray, m/e): 420 (M+H); IR cm-1: 3322, 2226, 1628.

EXAMPLE 44

4-(3-Bromo-phenylamino)-6-(3-morpholin-4-yl-propoxy)-[1,5]naphthyridine-3-carbonitrile A mixture of 4-chloro-6-(3-morpholin-4-yl-propoxy)-[1,5]naphthyridine-3-carbonitrile (700 mg, 2.10 mmol), 3-bromoaniline (0.458 ml, 4.2 mmol) and pyridine HCl salt (534 mg, 2.2 mmol) in ethoxyethanol (30 ml) was heated at reflux for 6 hrs under argon. After cooling, the solvent was removed by rotary evaporation. The residue was treated with ice water, made basic with $NH_4OH$, and extracted with ethyl acetate. The combined extracts were washed (sat brine), dried ($Na_2SO_4$), and concentrated. The oily residue was dissolved in $CH_2Cl_2$, and ether and n-hexane were added to form a solid. The title compound, as a yellow solid, was collected and dried. mass spectrum (electrospray, m/e): 469.9 (M+H); IR cm-1: 2224, 1668, 1628; H-NMR δ (DMSO-$d_6$): 1.88 (2H, m), 2.26–2.29 (6H, m), 2.51 (2H, m), 3.49 (2H, m), 4.34 (2H, m), 7.110–7.311 (3H, m), 7.835 (1H, d, C7-H), 8.240 (1H, d, C8-H), 8.556 (1H, s), 8.721 (1H, s, C2-H), 9.850 (1H, s, NH).

EXAMPLE 45

4-(3-Hydroxy-4-methyl-phenylamino)-6-(2-morpholin-4-yl-ethoxy)-[1,5]naphthyridine-3-carbonitrile By using the methods outlined above in Examples 39–43 and staring with 2-morpholin-ethanol, the title compound was obtained as a yellow solid. mass spectrum (electrospray, m/e): 405.9 (M+H); IR cm-1: 2227, 1628; H-NMR δ (DMSO-$d_6$): 2.08 (3H, bs), 2.44–2.48 (4H, m), 3.40–3.57 (4H, m), 4.226 (2H, m), 4.710 (2H, bs), 6.96–7.06 (2H, m), 7.06 (1H, bs), 7.028 (1H, d, C7-H), 8.097 (1H, d, C8-H), 8.706 (1H, s, C2-H), 9.32 (1H, bs, OH), 9.42 (1H, s, NH).

EXAMPLE 46

4-(3-Bromo-phenylamino)-6-(2-morpholin-4-yl-ethoxy)-[1,5]naphthyridine-3-carbonitrile By using the methods outlined above in Examples 39–44 and staring with 2-morpholin-ethanol, the title compound was obtained as a yellow solid. mass spectrum (electrospray, m/e): 455.9 (M+H); H-NMR δ (DMSO-$d_6$): 2.44–2.48 (4H, m), 3.40–3.57 (4H, m), 4.226 (2H, m), 4.710 (2H, bs), 7.110–7.311 (3H, m), 7.828 (1H, d, C7-H), 8.097 (1H, d, C8-H), 8.556 (1H, s), 8.706 (1H, s, C2-H), 9.42 (1H, s, NH).

EXAMPLE 47

6-Acetamido-4-hydroxyl-[1,5]naphthyridine-3-carbonitrile

2-Amino-5-nitropyridine was treated with acetic anhydride in dry pyridine in the presence of 4-dimethylaminopyridine at room temperature for 24 hrs under argon. The solvent was removed by rotary evaporation. The residue was dissolved in $CH_2Cl_2$, and ether was added to form a solid. The white solid was collected and dried giving 2-acetamido-5-nitropyridine. Hydrogenation of this material using 10% Pd on C in MeOH at room temperature under atmospheric pressure gave 2-acetamido-5-aminopyridine.

A solution of 2-acetamido-5-aminopyridine (1.6 g, 10.7 mmol) and ethyl(ethoxymethylene)cyanoacetate (3.6 g, 21.3 mmol) in toluene (50 ml) was heated at reflux for 10 hrs under argon. After cooling, the white solid was collected and dried. A solution of this solid in Dowtherm (250 ml) was heated at 255–260° C. for 6 hrs under nitrogen. During this process, ethanol was distilled off. The mixture was heated at 260° C. for an additional 5 hrs. After cooling, the mixture was poured in hexane. The solid was collected, dissolved in a 1:1 mixture of DMF and ethyl acetate, and ether was added to give the title compound as a solid. mass spectrum (electrospray, m/e): 228.7 (M+H); IR cm-1: 2228, 1682.; H-NMR δ (DMSO-$d_6$): 2.182 (3H, s, $CH_3$), 7.96 (1H, s, OH), 8.09 (1H, d, C7-H), 8.49 (1H, d, C8-H), 8.71 (1H, s, C2-H), 11.20 (1H, s, NH).

EXAMPLE 48

6-Acetamido-4-chloro-[1,5]naphthyridine-3-carbonitrile

A solution of 6-acetamido-4-hydroxyl-[1,5]naphthyridine-3-carbonitrile (1.0 g, 4.386 mmol) was heated at reflux in $POCl_3$ (20 ml) under nitrogen for 5 hrs. After cooling, the solvent was removed by rotary evaporation. Ice water was added to the black residue, which was cooled (ice bath) and stirred for 1 hr. The mixture was warmed to room temperature and stirred at room temperature for 1 hr. The mixture was cooled with ice bath, and made basic with $NH_4OH$. The aqueous layer was extracted with $CH_2Cl_2$. The combined extracts were washed with water, dried ($Na_2SO_4$) and concentrated to give the title compound as a dark blue solid (200 mg, 19%).

EXAMPLE 49

6-Amino-4-(3-bromo-phenylamino)-[1,5]naphthyridine-3-carbonitrile

A solution of 6-acetamido-4-chloro-[1,5]naphthyridine-3-carbonitrile (200 mg, 0.81 mmol), 3-bromoaniline (0.5 ml) and pyridine HCl (188 mg) in ethoxyethanol (20 ml) was heated at reflux for 3 hrs. After cooling, the solvent was removed by rotary evaporation, and the residue was cooled and made basic with $NH_4OH$. The aqueous layer was extracted with ethyl acetate. The combined extracts were washed (brine), dried ($Na_2SO_4$), and concentrated. The residue was chromatographed (flash column, silica gel, $CH_2Cl_2$: ether: MeOH=5:2:0.5) giving the title compound as a yellow solid (229 mg, 56%). mass spectrum (electrospray, m/e): 341.8 (M+H); IR cm-1: 2215, 1628; H-NMR δ (DMSO-$d_6$): 6.816 (2H, bs, $NH_2$), 7.093 (1H, d, C7-H), 7.35–7.43 (3H, m), 7.567 (1H, s), 7.931 (1H, d, C8-H), 8.333 (1H, s, C2-H), 9.236 (1H, s, NH).

EXAMPLE 50

6-Fluoro-pyridin-3-ylamine

To 100 g of 2-chloro-5-nitropyridine (Aldrich) in 600 mL of dimethyl sulfoxide under an inert atmosphere was added 100 g of anhydrous KF. The reaction was heated at 70° C. for 18 hours before cooling and diluting with 500 mL each of brine, ethyl acetate, and hexanes. This mixture was filtered through a pad of celite, the organic phase was separated, and the aqueous phase was extracted three times with equal volumes of ethyl acetate and hexanes. The pooled organic phases were washed with brine, dried with anhydrous sodium sulfate, and stripped of the solvents. This crude product was passed through a plug of silica gel with a gradient of 10–30% ethyl acetate/hexanes and stripped to constant weight on a rotary evaporator to give 76 g (84%) of 2-fluoro-5-nitropyridine as an oil, which was used in the following procedure.

To 76 g of 2-fluoro-5-nitropyridine in 500 ml of ethyl acetate under nitrogen was added 100 g of Raney nickel which had been washed three times with ethanol and three times with ethyl acetate. The nitrogen was replaced with hydrogen and the reaction was allowed to proceed for 18 hours at 30 lb/in². After the hydrogen atmosphere had been replaced by nitrogen, the reaction was filtered through celite and stripped of solvent. The product was purified by passing through a plug of silica gel with chloroform and recrystallized from chloroform to give 42 g (70%) of 6-fluoro-pyridin-3-ylamine in two crops as white platelets: melting point 90–91° C.; mass spectrum (m/e): M+H 112.7.

EXAMPLE 51

(6-Fluoro-pyridin-3-yl)-carbamic Acid, Tert-Butyl Ester

To 40 g of 6-fluoro-pyridin-3-ylamine and 20 mL of t-butanol was added 200 g of warm di-t-butyl dicarbonate. After stirring for 4 hours at 40° C., the reaction was diluted with hexanes and chilled at −15° C. for 18 hours. The crystals was filtered, washed with hexanes, and dried in vacuo to give 72 g (96%) of (6-fluoro-pyridin-3-yl)-carbamic acid, tert-butyl ester: melting point=112–113° C.; mass spectrum (m/e): M+H 213.1.

EXAMPLE 52

5-tert-Butoxycarbonylamino-2-fluoro-isonicotinic Acid

To 30 g of (6-fluoro-pyridin-3-yl)-carbamic acid, tert-butyl ester in 60 mL of tetramethylethylenediamine and 750 mL of ether at −78° C. under an inert atmosphere was added slowly 180 mL of 2.5 M n-butyllithium/hexanes (3 eq). After the addition was complete, the reaction was allowed to warm to −15° C. for 5 minutes then recooled to −78° C. Dry ice was allowed to sublime in a separate flask and the vapor was passed over the rapidly stirred reaction mixture while the cooling bath was removed and the reaction allowed to warm to 0° C. Sufficient water was added to dissolve the precipitated product and the resultant aqueous phase was washed twice with ether before acidifying with concentrated HCl. The precipitate was filtered, washed with water, and dried in vacuo to give 21.2 g of 5-tert-butoxycarbonylamino-2-fluoro-isonicotinic acid, which was used as is for the next step: melting point 240–245° C. (decomposed); mass spectrum (negative mode, m/e): M−H 255.2.

EXAMPLE 53

5-tert-Butoxycarbonylamino-2-fluoro-isonicotinic Acid, Methyl Ester

To 44 g of 5-tert-butoxycarbonylamino-2-fluoro-isonicotinic acid in 100 mL of methanol and 300 mL of chloroform at 0° C. was added 200 mL of 2 M (trimethylsilyl)diazomethane in hexanes. After allowing the reaction to warm to ambient temperature and stirring for 2 hours, the solvents were removed and the crude product purified by passing through a plug of silica gel with chloroform The product was then recrystallized from hexanes to give 32.6 g (73%) of 5-tert-butoxycarbonylamino-2-fluoro-isonicotinic acid, methyl ester: melting point 104 105° C. (decomposed); mass spectrum (m/e): M+H 270.9.

EXAMPLE 54

[6-Fluoro-4-(3-nitrilo-propionyl)-pyridin-3-yl]-carbamic Acid, Tert-Butyl Ester

To 140 mL of 2.5 M n-butyllithium/hexanes in 300 mL of tetrahydrofuran at −78° C. was slowly added 14.4 g of anhydrous acetonitrile in 100 mL of tetrahydrofuran. After 30 minutes was added 32 g of 5-tert-butoxycarbonylamino-2-fluoro-isonicotinic acid, methyl ester in 100 mL of tetrahydrofuran. After a further 60 minutes, the reaction was quenched with 35 mL of glacial acetic acid. The reaction was diluted with equal volumes of ethyl acetate and saturated sodium bicarbonate and the aqueous phase was washed twice with ethyl acetate. The pooled organic phases were washed with saturated sodium bicarbonate, dried, and stripped of solvent. This material was further purified by passing through a plug of silica gel with a gradient of 0–5% methanol/chloroform to give a crude product that was used as is for the following step. This material can be further purified by recrystallization from chloroform/hexanes to give a white, crystalline solid: melting point 106–115° C.; mass spectrum (m/e): M+H 279.9.

EXAMPLE 55

6-Fluoro-4-hydroxy-[1,7]naphthyridine-3-carbonitrile

The crude product from the previous step was dissolved under an inert atmosphere in 50 mL each of dimethyl formamide and dimethyl formamide dimethyl acetal. After 1 hour, 50 mL of 10% water in methanol was added and the volatile solvents were stripped on a rotary evaporator. This material was purified by flash chromatography with a gradient of 0–30% methanol/chloroform to give 19 g (85%, two steps) of 6-fluoro-4-hydroxy-[1,7]naphthyridine-3-carbonitrile as a yellowish solid: melting point 214–215° C.; mass spectrum (negative mode, m/e): M−H 188.1.

EXAMPLE 56

4-Chloro-6-fluoro-[1,7]naphthyridine-3-carbonitrile

To 10 g of 6-fluoro-4-hydroxy-[1,7]naphthyridine-3-carbonitrile under an inert atmosphere in 150 mL of methylene chloride was added 24 mL of oxalyl chloride followed by 0.4 mL of N,N-dimethyl formamide. After two hours at reflux, an additional 5 mL of oxalyl chloride and 0.3 mL of N,N-dimethyl formamide was added. After an additional hour at reflux, the reaction was poured into ice-water and solid potassium carbonate was added carefully to a pH of about 8. The chloroform layer was washed with brine, dried with sodium sulfate, and stripped to give a crude product. This material was further purified by passing it through a plug of silica gel with chloroform and recrystallizing from a mixture of chloroform and hexanes to give 10 g (92%) of 4-chloro-6-fluoro-[1,7]naphthyridine-3-carbonitrile as a yellowish solid: melting point 150–155° C.; mass spectrum (m/e): M+H$_2$O—Cl 190.0.

EXAMPLE 57

4-(3-Bromo-phenylamino)-6-fluoro-[1,7]naphthyridine-3-carbonitrile

To 1.9 g of 4-chloro-6-fluoro-[1,7]naphthyridine-3-carbonitrile in 30 mL of absolute ethanol was added 1.6 mL of 3-bromoaniline. After refluxing the reaction under an inert atmosphere for 8 hours, the reaction mixture was cooled to 0° C. and the product was filtered and washed with cold ethanol. Drying in vacuo yielded 2.7 g (87%) of 4-(3-bromo-phenylamino)-6-fluoro-[1,7]naphthyridine-3-carbonitrile as an off-white solid: melting point 185–195° C.; mass spectrum (m/e): M+H 343.0, 345.1.

EXAMPLE 58

4-(3-Bromo-phenylamino)-6-(4-methoxy-benzylamino)-[1,7]naphthyridine-3-carbonitrile To 1 g of 4-(3-bromo-phenylamino)-6-fluoro-[1,7]naphthyridine-3-carbonitrile in 25 mL of absolute ethanol was added 2 ml of 4-methoxy-benzylamine. The reaction was refluxed for eight days, stripped of solvents, and passed through a plug of silica gel with 5% methanol/chloroform. Fractions containing product were pooled and further purified by flash chromatography on silica gel with a gradient of 1–2% methanol/chloroform to give 595 mg (45%) of 4-(3-bromo-phenylamino)-6-(4-methoxy-benzylamino)-[1,7]naphthyridine-3-carbonitrile, which was sufficiently pure for further transformations. The product was recrystallized by dissolving in a minimum amount of warm chloroform, diluting with ether, and then adding hexanes to give 195 mg: melting point 82–86° C. (decomposed); mass spectrum (m/e): M+H 460.2, 462.2.

EXAMPLE 59

6-Amino-4-(3-bromo-phenylamino)-[1,7]naphthyridine-3-carbonitrile

To 400 mg of 4-(3-bromo-phenylamino)-6-(4-methoxy-benzylamino)-[1,7]naphthyridine-3-carbonitrile in 10 mL of methylene chloride was added 10 mL of trifluoroacetic acid. After stirring under an inert atmosphere for 20 hours, 10 mL of toluene was added and the solvents were stripped on a rotary evaporator. The product was purified by flash chromatography with a gradient of 0–5% methanol/chloroform to give 250 mg of 6-amino-4-(3-bromo-phenylamino)-[1,7]naphthyridine-3-carbonitrile as an off-white solid: melting point 185–190° C. (decomposed); mass spectrum (m/e): M+H 340.0, 342.1.

EXAMPLE 60

6-Amino-4-(4-methoxy-benzylamino)-[1,7]naphthyridine-3-carbonitrile

To 1.3 g of 4-(3-bromo-phenylamino)-6-fluoro-[1,7]naphthyridine-3-carbonitrile in 20 mL of absolute ethanol was added 5 ml of 4-methoxy-benzylamine. The reaction was refluxed for six days, stripped of solvents, and passed through a plug of silica gel with 5% methanol/chloroform. This crude product was dissolved in 10 mL of chloroform containing 5% anisole and 10 mL of trifluoroacetic acid was added. After stirring under an inert atmosphere for 20 hours, 10 mL of toluene was added and the solvents stripped on a rotary evaporator. The product was purified by flash chromatography with a gradient of 0–10% methanol/chloroform. The solid was extracted with hot, 5% methanol/isopropyl

EXAMPLE 61

But-2-ynoic Acid, [4-(3-bromo-phenylamino)-3-cyano-[1,7]naphthyridin-6-yl]-amide To 100 mg of butynoic acid in 5 mL of anhydrous tetrahydrofuran under an inert atmosphere at 0° C. was added 0.23 mL on N-methyl morpholine and 0.15 mL of isobutyl chloroformate. This solution was then added to 150 mg of 6-amino-4-(3-bromo-phenylamino)-[1,7]naphthyridine-3-carbonitrile in 3 mL of pyridine at 0° C. After standing at 0° C. for three days, a second portion of butynoyl chloride was added. After an additional 8 hours the reaction was stripped of solvents on a rotary evaporator and the crude product was purified by flash chromatograph using a gradient of 0–20% methanol/chloroform to give 15 mg of but-2-ynoic acid, [4-(3-bromo-phenylamino)-3-cyano-[1,7]naphthyridin-6-yl]-amide: melting point 255° C. (decomposed); mass spectrum (m/e): M+H 406.1, 408.2.

EXAMPLE 62

4-Dimethylamino-but-2-enoic Acid, [4-(3-bromo-phenylamino)-3-cyano-[1,7]naphthyridin-6-yl]-amide 4-Bromobut-2-enoyl chloride was generated by the reaction of 4-bromobut-2-enoic acid, trimethylsilyl ester (0.63 mL) with oxalyl chloride (0.33 mL) in methylene chloride (6 mL) with one drop of N,N-dimethyl formamide for one hour. The reaction was stripped of solvent and redissolved in 8 mL of anhydrous tetrahydrofuran. An aliquot of 4 mL of this reagent was added to a solution of 500 mg of 6-amino-4-(3-bromo-phenylamino)-[1,7]naphthyridine-3-carbonitrile in 15 mL of tetrahydrofuran containing 315 uL of Hunig's base at 0° C. After 2 hours, an additional 2 mL of acid chloride/tetrahydrofuran was added. After an additional hour, saturated aqueous sodium bicarbonate and chloroform was added and the chloroform phase dried and stripped to give a crude product that was purified by flash chromatography with a gradient of ethyl acetate/chloroform, then methanol/chloroform to give 360 mg of a one-to-one mixture of 4-bromo-but-2-enoic acid, [4-(3-bromo-phenylamino)-3-cyano-[1,7]naphthyridin-6-yl]-amide, and 4-chloro-but-2-enoic acid, [4-(3-bromo-phenylamino)-3-cyano-[1,7]naphthyridin-6-yl]-amide. This material was dissolved in 10 mL of tetrahydrofuran containing 1 mL of N,N-dimethyl formamide and reacted with 200 mg of NaBr for three days. An aliquot of 2 mL of 1 M dimethyl amine in tetrahydrofuran was then added at 0° C. The reaction was diluted with saturated aqueous sodium bicarbonate, ice, and chloroform. The organic phase was dried with sodium sulfate, evaporated, and purified by flash chromatography with a gradient of 5–10% methanol/chloroform to give 190 mg of 4-dimethylamino-but-2-enoic acid, [4-(3-bromo-phenylamino)-3-cyano-[1,7]naphthyridin-6-yl]-amide as an amorphous yellow solid: melting point 180–185° C. (decomposed); mass spectrum (m/e): M+H 450.9, 452.9.

EXAMPLE 63

4-(3-Bromo-phenylamino)-6-(2-morpholino-4-yl-ethylamino)-[1,7]naphthyridine-3-carbonitrile To 500 mg of 4-(3-bromo-phenylamino)-6-fluoro-[1,7]naphthyridine-3-carbonitrile in 5 mL of pyridine was added 0.4 mL of N-aminoethyl morpholine. The reaction heated at 80° C. for three days, stripped of solvents, and passed through a plug of silica gel with 5% methanol/chloroform. Fractions containing product were pooled and further purified by flash chromatography on silica gel with a gradient of 0–5% methanol/chloroform Recrystallization from chloroform/hexanes yielded 200 mg of 4-(3-bromo-phenylamino)-6-(2-morpholino-4-yl-ethylamino)-[1,7]naphthyridine-3-carbonitrile: melting point 80–96° C. (decomposed); mass spectrum (m/e): M+H 453.0, 455.0.

EXAMPLE 64

4-(3-Bromo-phenylamino)-6-methylamino-[1,7]naphthyridine-3-carbonitrile

To 500 mg of 4-(3-bromo-phenylamino)-6-fluoro-[1,7]naphthyridine-3-carbonitrile in 15 mL of absolute ethanol was added 4 mL of 40% aqueous methyl amine. The sealed reaction was heated at 90° C. for 24 hours, stripped of solvents, and purified by flash chromatography on silica gel with a gradient of 0–1% methanol/chloroform followed by purification by preparative thin-layer chromatography with 5% methanol/chloroform to yield 86 mg of 4-(3-bromo-phenylamino)-6-methylamino-[1,7]naphthyridine-3-carbonitrile as an amorphous solid: melting point 250° C. (decomposed); mass spectrum (m/e): M+H 354.1, 356.1.

EXAMPLE 65

1-[4-(3-Bromo-phenylamino)-3-cyano-[1,7]naphthyridin-6-yl]-4-diethylamino-pyridinium Fluoride To 200 mg of 4-(3-bromo-phenylamino)-6-fluoro-[1,7]naphthyridine-3-carbonitrile in 5 mL of absolute ethanol was added 200 mg of 4-dimethylaminopyridine. The reaction was refluxed for three days before cooling to ambient temperature and filtering the product which was washed with cold ethanol then ether and dried to give 290 mg (100%) of 1-[4-(3-bromo-phenylamino)-3-cyano-[1,7]naphthyridin-6-yl]-4-dimethylamino-pyridinium fluoride as a white, crystalline solid; mass spectrum (m/e): M 445.0, 447.1.

EXAMPLE 66

6-Fluoro-4-(3-hydroxy-4-methyl-phenylamino)-[1,7]naphthyridine-3-carbonitrile

To 1.5 g of 4-chloro-6-fluoro-[1,7]naphthyridine-3-carbonitrile in 40 mL of absolute ethanol was added 1.1 g of 3-hydroxy-4-methylaniline. After stirring the reaction under an inert atmosphere for 16 hours, the reaction mixture was poured into a mixture of brine and saturated aqueous sodium bicarbonate and the resultant crystals were filtered and washed with water. The product was then recrystallized from chloroform/ether/hexanes. Drying in vacuo yielded 1.9 g (90%) of 6-fluoro-4-(3-hydroxy-4-methyl-phenylamino)-[1,7]naphthyridine-3-carbonitrile as a yellow powder: melting point 236–239° C. (decomposed); mass spectrum (m/e): M+H 294.9.

EXAMPLE 67

6-Fluoro-4-(4-phenoxy-phenylamino)-[1,7]naphthyridine-3-carbonitrile

To 2.0 g of 4-chloro-6-fluoro-[1,7]naphthyridine-3-carbonitrile in 50 mL of methanol was added 2.2 g of 4-phenoxyaniline. After stirring the reaction under an inert atmosphere for 18 hr, the reaction mixture was poured into a mixture of brine and saturated aqueous sodium bicarbonate and the resultant crystals filtered and washed with water. The product was then recrystallized from chloroform/hexanes. Drying in vacuo yielded 2.35 g (69%) of 6-fluoro-4-(4-phenoxy-phenylamino)-[1,7]naphthyridine-3-carbonitrile as yellow needles: melting point 211–213° C.; mass spectrum (m/e): M+H 356.9.

EXAMPLE 68

4-(2,4-Dichloro-phenylamino)-6-fluoro-[1,7]naphthyridine-3-carbonitrile

To 2.0 g of 4-chloro-6-fluoro-[1,7]naphthyridine-3-carbonitrile in 50 mL of methanol was added 1.9 g of 2,4-dichloroaniline. After refluxing the reaction under an inert atmosphere for 2 hours, the reaction mixture was poured into a mixture of brine and saturated aqueous sodium bicarbonate and the resultant crystals were filtered and washed with water. The product was then recrystallized from chloroform/hexanes. Drying in vacuo yielded 2.6 g (80%) of 4-(2,4dichloro-phenylamino)-6-fluoro-[1,7]naphthyridine-3-carbonitrile as yellow needles: melting point 206–208° C.; mass spectrum (m/e): M+H 332.8.

EXAMPLE 69

4-(3-Chloro-4-fluoro-phenylamino)-6-fluoro-[1,7]naphthyridine-3-carbonitrile

To 600 mg of 4-chloro-6-fluoro-[1,7]naphthyridine-3-carbonitrile in 15 mL of absolute ethanol was added 500 mg of 3-chloro-4-fluoroaniline. After refluxing the reaction under an inert atmosphere for 2 hours, the reaction mixture was poured into a mixture of brine and saturated aqueous sodium bicarbonate and the resultant crystals were filtered and washed with water. The product was then recrystallized from chloroform/hexanes. Drying in vacuo yielded 765 mg (83%) of 4-(3-chloro-4-fluoro-phenylamino)-6-fluoro-[1,7]naphthyridine-3-carbonitrile as yellow needles: melting point 108–111° C.; mass spectrum (m/e): M+H 316.8.

EXAMPLE 70

4-(4-Chloro-2-fluoro-phenylamino)-6-fluoro-[1.7]naphthyridine-3-carbonitrile

To 3.5 g of 4-chloro-6-fluoro-[1,7]naphthyridine-3-carbonitrile in 100 mL of absolute ethanol was added 2.3 mL of 4-chloro-2-fluoroaniline. After stirring the reaction under an inert atmosphere for 24 hours, the reaction mixture was poured into a mixture of brine and saturated aqueous sodium bicarbonate and the resultant crystals were filtered and washed with water. The product was then recrystallized from chloroform/ethyl acetate/hexanes. Drying in vacuo yielded 1.9 (40%) of 4-(4-chloro-2-fluoro-phenylamino)-6-fluoro-[1,7]naphthyridine-3-carbonitrile as yellow needles: melting point 249–252° C.; mass spectrum (m/e): M+H 316.9.

EXAMPLE 71

4-(4-Chloro-2-fluoro-phenoxy)-6-fluoro-[1,7]naphthyridine-3-carbonitrile

An aliquot of 2.8 mL of 4-chloro-2-fluorophenol and 400 mg of powdered KOH was melted under an inert atmosphere at 100° C. until clear. After cooling to 60° C., 850 mg of 4-chloro-6-fluoro-[1,7]naphthyridine-3-carbonitrile was added and the sides of the flask washed with absolute ethanol. The ethanol was driven off with a stream of nitrogen over 30 minutes, at which time the reaction was complete. The reaction was diluted with 0.1 M NaOH and chloroform and the organic layer was dried with sodium sulfate and evaporated of solvent.

The product was then recrystallized from chloroform/ether. Drying in vacuo yielded 0.9 g (69%) of 4-(4-chloro-2-fluoro-phenoxy)-6-fluoro-[1,7]naphthyridine-3-carbonitrile as a white solid: melting point 186–188° C.; mass spectrum (m/e): M+H 317.8.

EXAMPLE 72

1 M Sodium (2-dimethylamino-ethoxide) in Tetrahydrofuran

To 2.0 g of NaH in 50 mL of tetrahydrofuran at 0° C. under an inert atmosphere was slowly added 5.0 mL of 2-dimethylamino-ethanol. The solution was allowed to warm to ambient temperature before use.

EXAMPLE 73

6-(2-Dimethylamino-ethoxy)4(4-phenoxy-phenylamino)-[1,7]naphthyridine-3-carbonitrile To 250 mg of 6-fluoro-4-(4-phenoxy-phenylamino)-[1,7]naphthyridine-3-carbonitrile under an inert atmosphere was added 8 mL of 1 M sodium (2-dimethylamino-ethoxide) in tetrahydrofuran. After refluxing for 2 hours, the reaction was stripped of tetrahydrofuran and water was added. The product was filtered, washed with water, dried, and recrystallized from chloroform/ether/hexanes to give 266 mg (85%) of 6-(2-dimethylamino-ethoxy)-4-(4-phenoxy-phenylamino)-[1,7]naphthyridine-3-carbonitrile as a yellow solid: melting point 159–161° C.; mass spectrum (m/e): M+H 426.0.

EXAMPLE 74

4-(3-Chloro-4-fluoro-phenylamino)-6-(2-dimethylamino-ethoxy)-[1,7]naphthyridine-3-carbonitrile To 250 mg of 4-(3-chloro-4-fluoro-phenylamino)-6-fluoro-[1,7]naphthyridine-3-carbonitrile under an inert atmosphere was added 8 mL of 1 M sodium (2-dimethylamino-ethoxide) in tetrahydrofuran. After refluxing for 2 hours, the reaction was stripped of tetrahydrofuran and water was added. The product was filtered, washed with water, dried, and recrystallized from chloroform/ether/hexanes to give 210 mg (66%) of 4-(3-chloro-4-fluoro-phenylamino)-6-(2-dimethylamino-ethoxy)-[1,7]naphthyridine-3-carbonitrile as a yellow solid: melting point 131–132° C.; mass spectrum (m/e): M+H 386.0.

EXAMPLE 75

4-(2.4-Dichloro-phenylamino)-6-(2-dimethylamino-ethoxy)-[1,7]naphthyridine-3-carbonitrile To 250 mg of 4-(2,4-dichloro-phenylamino)-6-fluoro-[1,7]naphthyridine-3-carbonitrile under an inert atmosphere was added 8 mL of 1 M sodium (2-dimethylamino-ethoxide) in tetrahydrofuran. After refluxing for 2 hours, the reaction was stripped of tetrahydrofuran and water was added. The product was filtered, washed with water, dried, and recrystallized from chloroform/ether/hexanes to give 186 mg (59%) of 4-(2,4-dichloro-phenylamino)-6-(2- dimethylamino-ethoxy)-[1,7]naphthyridine-3-carbonitrile as a yellow solid: melting point 75–9° C.; mass spectrum (m/e): M+H 401.9.

EXAMPLE 76

4-(4-Chloro-2-fluoro-phenylamino)-6-(2-dimethylamino-ethoxy)-[1,7]naphthyridine-3-carbonitrile To 250 mg of 4-(4-chloro-2-fluoro-phenylamino)-6-fluoro-[1,7]naphthyridine-3-carbonitrile under an inert atmosphere was added 8 mL of 1 M sodium (2dimethylamino-ethoxide) in tetrahydrofuran. After refluxing for 2 hours, the reaction was stripped of tetrahydrofuran and water was added. The product was filtered, washed with water, dried, and recrystallized from chloroform/ether/hexanes to give 204 mg (64%) of 4-(4-chloro-2-fluoro-phenylamino)-6-(2-dimethylamino-ethoxy)-[1,7]naphthyridine-3-carbonitrile as a yellow solid: melting point 150–152° C.; mass spectrum (m/e): M+H 385.9.

EXAMPLE 77

4-(3-Bromo-phenylamino)-6-(2-dimethylamino-ethoxy)-[1,7]naphthyridine-3-carbonitrile To 100 mg of 4-(3-bromo-phenylamino)-6-fluoro-[1,7]naphthyridine-3-carbonitrile under an inert atmosphere was added 3 mL of 1 M sodium (2-dimethylamino-ethoxide) in tetrahydrofuran. After refluxing for 3 hours, the reaction was diluted with water and the product extracted five times with chloroform. The crude product was purified by flash chromatography with 1% triethyl amine and 10% methanol/chloroform followed by recrystallized from chloroform/ether to give 100 mg of 4-(3-bromo-phenylamino)-6-(2-dimethylamino-ethoxy)-[1,7]naphthyridine-3-carbonitrile as a yellow solid: melting point 138–139° C.; mass spectrum (m/e): M+H 411.9, 413.9.

EXAMPLE 78

6-(2-Dimethylamino-ethoxy)-4-(3-hydroxy-4-methyl-phenylamino)-[1,7]naphthyridine-3-carbonitrile To 160 mg of 6-fluoro-4-(3-hydroxy-4-methyl-phenylamino)-[1,7]naphthyridine-3-carbonitrile under an inert atmosphere was added 3 mL of 1 M sodium (2-dimethylamino-ethoxide) in tetrahydrofuran. After refluxing for 3 hours, the reaction was diluted with Water and the product extracted five times with chloroform. The crude product was purified by flash chromatography with 1% triethyl amine and 10% methanol/chloroform followed by recrystallized from chloroform/ether to give 106 mg of 6-(2-dimethylamino-ethoxy)-4-(3-hydroxy-4-methyl-phenylamino)-[1,7]naphthyridine-3-carbonitrile as a yellowish solid: melting point 100–180° C. (decomposed, effervescence); mass spectrum (m/e): M+H 419.9.

EXAMPLE 79

(6-Chloro-pyridin-3-yl)-carbamic Acid, Tert-Butyl Ester

To 50 g of 2-chloro-5-nitropyridine in 250 ml of ethyl acetate under nitrogen was added 30 g of Raney nickel which had been washed three times with ethanol and three times with ethyl acetate. The nitrogen was replaced with hydrogen and the reaction was allowed to proceed for 6 hours at 30 lb/in². After the hydrogen atmosphere had been replaced by nitrogen, the reaction was filtered through celite and evaporated. The product was purified by flash chromatography on silica gel with a gradient of ethyl acetate/chloroform followed by methanol/chloroform to give 16 g of 6-chloro-pyridin-3-ylamine as white platelets (Mp 81–2° C.). This material was further reacted as follows.

To 15 g of 6-chloro-pyridin-3-ylamine in 200 mL of methylene chloride was added 28 g of warm di-t-butyl dicarbonate and 15 mL of triethyl amine. After refluxing for 18 hours, the reaction was diluted with hexanes and chilled at −15° C. for 18 hours. The reaction was filtered and the organic layer was washed with water, dried, and concentrated. The product was then recrystallized from chloroform/hexanes and dried in vacuo to give 14 g of (6-chloro-pyridin-3-yl)-carbamic acid, tert-butyl ester: mp=126–127° C.; mass spectrum (m/e): M+H 229.0.

EXAMPLE 80

5-tert-Butoxycarbonylamino-2-chloro-isonicotinic Acid

To 13 g of (6-chloro-pyridin-3-yl)-carbamic acid, tert-butyl ester in 24 mL of tetramethylethylenediamine and 300 mL of ether at −78° C. under an inert atmosphere was added slowly 68 mL of 2.5 M n-butyllithium/hexanes (3 eq). After the addition was complete, the reaction was allowed to warm to −15° C. for two hours then recooled to −78° C. Dry ice was allowed to sublime in a separate flask and the vapor was passed over the rapidly stirred reaction mixture while the cooling bath was removed and the reaction allowed to warm to 0° C. Sufficient water was added to dissolve the precipitated product and the resultant aqueous phase was washed twice with ether before acidifying with concentrated HCl. The precipitate was filtered, washed with water, and dried in vacuo to give 10.9 g of 5-tert-butoxycarbonylamino-2-chloro-isonicotinic acid, which was used as is for the next step: melting point 250° C. and higher (slowly decomposed); mass spectrum (negative mode, m/e): M−H 271.1.

EXAMPLE 81

5-tert-Butoxycarbonylamino-2-chloro-isonicotinic Acid, Methyl Ester

To 5.4 g of 5-tert-butoxycarbonylamino-2-chloro-isonicotinic acid in 50 mL of methanol and 100 mL of chloroform was at 0° C. was added 15 mL of 2 M (trimethylsilyl)diazomethane in hexanes. After allowing the reaction to warm to ambient temperature and stirring for 2 hours, the solvents were removed and the crude product purified by passing through a plug of silica gel with chloroform. The product was then recrystallized from hexanes to give 5.8 g (100%) of 5-tert-butoxycarbonylamino-2-chloro-isonicotinic acid, methyl ester: mp=90–96° C. (decomposed); mass spectrum (m/e): M+H 287.1.

EXAMPLE 82

6-Chloro-4-hydroxy-[1,7]naphthyridine-3-carbonitrile

To 21 mL of 1.5 M lithium diisopropylamide/cyclohexanes in 70 mL of tetrahydrofuran at −78° C. was slowly added 1.64 mL of anhydrous acetonitrile in 3.4 mL of tetrahydrofuran. After 15 minutes was added 3 g of 5-tert-butoxycarbonylamino-2-chloro-isonicotinic acid, methyl ester in 7 mL of tetrahydrofuran. After a further 30 minutes, the reaction was quenched with 2 mL of glacial acetic acid. The reaction was diluted with equal volumes of ethyl acetate and saturated sodium bicarbonate and the aqueous phase was washed twice with ethyl acetate. The pooled organic phases were washed with saturated sodium bicarbonate, dried, and stripped of solvent. This material was further purified by passing through a plug of silica gel with a gradient of 0–5% methanol/chloroform to give a crude product that was used as is for the following step.

The crude product for the previous step was dissolved under an inert atmosphere in 10 mL each dimethyl formamide and dimethyl formamide dimethyl acetal. After 18 hours the volatile solvents were stripped on a rotary evaporator and the product was purified by flash chromatography with first 5% methanol/chloroform until the product started to elute, then 30% methanol/chloroform to finish elution. Recrystallization from hexanes containing a trace of chloroform gave 1.5 g (69%, two steps) of 6-chloro-4-hydroxy-[1,7]naphthyridine-3-carbonitrile as a yellowish solid: melting point 280° C. (decomposed); mass spectrum (negative mode, m/e): M−H 203.9.

EXAMPLE 83

4-(3-Bromo-phenylamino)-6-chloro-[1,7]naphthyridine-3-carbonitrile

To 650 mg of 6-chloro-4-hydroxy-[1,7]naphthyridine-3-carbonitrile under an inert atmosphere was added 20 mL of phosphorous oxychloride. After two hours at reflux, the excess phosphorous oxychloride was removed in vacuo and ice-water and chloroform were added. Solid potassium carbonate was then added carefully to a pH of about 8. The chloroform layer was washed with brine, dried with sodium sulfate, and stripped to give a crude product. This material was further purified by passing it through a plug of silica gel with 5% ethyl acetate/chloroform to give approximately 600 mg of 4,6-dichloro-[1,7]naphthyridine-3-carbonitrile as a yellowish solid, which was used in the following step.

To the above 600 mg of 4,6-dichloro-[1,7]naphthyridine-3-carbonitrile in 20 mL of absolute ethanol was added 1 mL of 3-bromoaniline. After refluxing the reaction under an inert atmosphere for 4 hours, the reaction mixture was cooled to ambient temperature, diluted with ether, and the product was filtered and washed with ether. Drying in vacuo yielded 790 mg of 4-(3-bromo-phenylamino)-6chloro-[1,7]naphthyridine-3-carbonitrile as an off-white solid: mp=220–223° C.; mass spectrum (m/e): M+H 359.0, 361.1.

EXAMPLE 84

4-Hydroxy-6-trimethylsilanylethynyl-[1,7]naphthyridine-3-carbonitrile

To 1 g of 6-chloro-4-hydroxy-[1,7]naphthyridine-3-carbonitrile in 5 mL each dimethyl formamide and triethyl amine was added 1 g triphenyl phosphine, 7 mL of trimethylsilanylethyne, and 225 mg of palladium (II) acetate. The reaction was heated at 120° C. for 18 hours, stripped of solvent, and purified by flash chromatography on silica gel with a methanol/chloroform gradient. Recrystallization from ethanol containing a small amount of water yielded 690 mg of 4-hydroxy-6-trimethylsilanylethynyl-[1,7]naphthyridine-3-carbonitrile: melting point 307° C. (decomposed); mass spectrum (m/e): M+H 268.0.

EXAMPLE 85

4-(3-Bromo-phenylamino)-6-trimethylsilanylethynyl-[1,7]naphthyridine-3-carbonitrile To 500 mg of 4-hydroxy-6-trimethylsilanylethynyl-[1,7]naphthyridine-3-carbonitrile under an inert atmosphere was added 10 mL of phosphorous oxychloride. After two hours at reflux, the excess phosphorous oxychloride was removed in vacuo and ice-water, chloroform, a tract of methanol, and aqueous saturated sodium bicarbonate were added. The chloroform layer was washed with brine, dried with sodium sulfate, and evaporated to give 626 mg of crude 4-chloro-6-trimethylsilanylethynyl-[1,7]naphthyridine-3-carbonitrile as a yellowish solid, which was used in the following step.

To 626 mg of 4-chloro-6-trimethylsilanylethynyl-[1,7]naphthyridine-3-carbonitrile in 20 mL of absolute ethanol was added 1 mL of 3-bromoaniline. After refluxing the reaction under an inert atmosphere for 18 hours, the reaction mixture was cooled to ambient temperature, concentrated to 5 mL, diluted with ether, and the product filtered and washed with ether. Drying in vacuo yielded 500 mg of 4(3-bromo-phenylamino)-6-trimethylsilanylethynyl-[1,7]naphthyridine-3-carbonitrile as an off-white solid: melting point 125° C. (sublimed); mass spectrum (m/e): M+H 421.1, 423.2.

EXAMPLE 86

4-(3-Bromo-phenylamino)-6-ethynyl-[1,7]naphthyridine-3-carbonitrile

To 800 mg of 4-(3-bromo-phenylamino)-6-trimethylsilanylethynyl-[1,7]naphthyridine-3-carbonitrile in 20 mL of tetrahydrofuran at 0° C. under an inert atmosphere was added 2.5 mL of 1 M tetrabutylammonium fluoride/tetrahydrofuran. After 1 hour at ambient temperature, the reaction was diluted with ethyl acetate and washed with brine. The organic layer was dried with sodium sulfate and evaporated. The product was purified by flash chromatography on silica gel to give 300 mg of 4-(3-bromo-phenylamino)-6-ethynyl-[1,7]naphthyridine-3-carbonitrile: melting point 224° C. (decomposed); mass spectrum (m/e): M+H 349.1, 351.1.

What is claimed is:

1. A compound of formula I having the structure

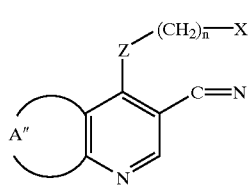

I wherein:

X is the radical

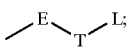

E is Ph;

T is substituted on E at carbon and is
—NH(CH$_2$)$_m$—, —NR(CH$_2$)$_m$—,
—(CH$_2$)$_m$NH—, or —(CH$_2$)$_m$NR—;

L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;

A" is a diavalent moiety selected from the group

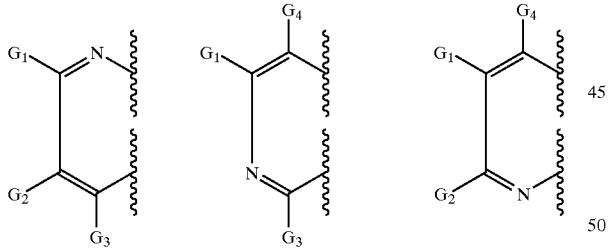

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_2NH$,

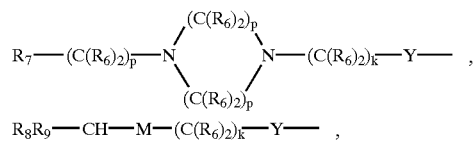

$R_8R_9$—CH—M—$(C(R_6)_2)_k$—Y—, $R_7$—$(C(R_6)_2)_g$"Y—, $R_7$—$(C(R_6)_2)_p$—M—$(C(R_6)_2)_k$—Y—, Het-$(C(R_6)_2)_q$—W—$(C(R_6)_2)_k$—Y—, with the proviso that $G_3$ and $G_4$ are not $R_2NH$;

Y is a divalent radical selected from the group consisting of

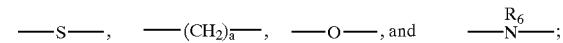

$R_7$ is —$NR_6R_6$, —$OR_6$, —J, —$N(R_6)_3^+$, or —$NR_6(OR_6)$;
M is >$NR_6$, —O—, >N—$(C(R_6)_2)_p NR_6R_6$, or >N—$(C(R_6)_2)_p$—$OR_6$;
W is >$NR_6$, —O— or is a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and

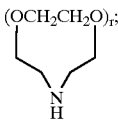

which may be optionally mono- or di-substituted on carbon with $R_6$, hydroxy, —$N(R_6)_2$, —$OR_6$—$(C(R_6)_2)_s OR_6$ or —$(C(R_6)_2)_s N(R_6)_2$; optionally mono-substituted on nitrogen with $R_6$; and optionally mono or di-substituted on a saturated carbon with divalent radicals —O— or —$O(C(R_6)_2)_s O$—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

[structures shown]

R₃ is hydrogen, alkyl of 1–6 carbon atoms, carboxy, carboalkoxy of 1–6 carbon atoms, phenyl, carboalkyl of 2–7 carbon atoms,

[structure: $R_7$—(C(R_6)_2)_p—N(piperazine-like)—(C(R_6)_2)_r—]

$R_7$—(C(R_6)_2)_s—, $R_7$—(C(R_6)_2)_p—M—(C(R_6)_2)_r—, $R_8R_9$—CH—M—(C(R_6)_2)_r—, or Het-(C(R_6)_2)_q—W—(C(R_6)_2)_r—;

$R_5$ is hydrogen, alkyl of 1–6 carbon atoms, carboxy, carboalkoxy of 1–6 carbon atoms, phenyl, carboalkyl of 2–7 carbon atoms,

[structure: $R_7$—(C(R_6)_2)_p—N(piperazine-like)—(C(R_6)_2)_r—]

$R_7$—(C(R_6)_2)_s—, $R_7$—(C(R_6)_2)_p—M—(C(R_6)_2)_r—, $R_8R_9$—CH—M—(C(R_6)_2)_r—, or Het-(C(R_8)_2)_q—W—(C(R_6)_2)_r—;

$R_8$, and $R_9$ are each, independently, —(C(R_6)_2)_rNR_6R_6, or —(C(R_6)_2)_rOR_6;

J is independently hydrogen, chlorine, fluorine, or bromine;

Q is alkyl of 1–6 carbon atoms or hydrogen;

a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and provided that
when $R_3$ is bound to sulfur, it cannot be hydrogen, carboxy, carboalkoxy, or carboalkyl;
and provided that
when Y is —$NR_6$— and $R_7$ is —$NR_6R_6$, —$N(R_6)_3^+$, or —$NR_6(OR_6)$, then g=2–6;
when M is —O— and $R_7$ is —$OR_6$ then p=1–4;
when Y is —$NR_6$— then k=2–4;
when Y is —O— and M or W is —O— then k=1–4
when W is not a bond with Het bonded through a nitrogen atom then q=2–4
and when W is a bond with Het bonded through a nitrogen atom and Y is —O— or —NR6— then k=2–4;
and finally provided that
when A" is the moiety

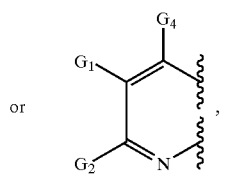

n=0,
Z is NH,
$G_1$ is hydrogen, halogen, alkyl, alkoxy, hydroxy, alkanoyloxy of 2–6 carbon atoms, or phenoxy, and
$G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino,
then X can not be a phenyl ring that is substituted with a hydroxy or alkoxy group.

2. The compound according to claim 1 wherein Z is —NH— and n=0 or a pharmaceutically acceptable salt thereof.

3. The compound according to claim 2 wherein $G_3$ and $G_4$ are hydrogen or a pharmaceutically acceptable salt thereof.

4. A method of inhibiting the biological effects of a deregulated protein tyrosine kinase in a mammal in need thereof which comprises administering to said mammal a compound of formula 1 having the structure

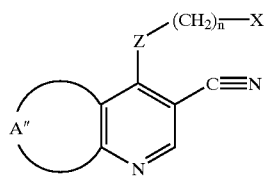

wherein:
X is the radical

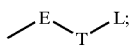

E is Ph;
—$NH(CH_2)_m$—, —$NR(CH_2)_m$—, —$(CH_2)_mNH$—, or —$(CH_2)_mNR$—;
L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;
A" is a diavalent moiety selected from the group

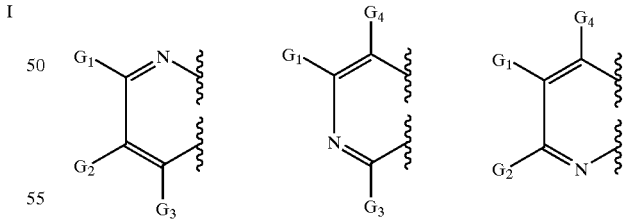

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_2NH$,

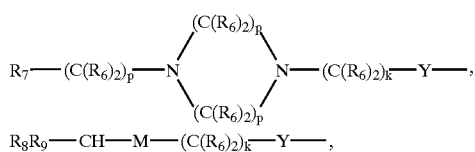

$R_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—,
with the proviso that $G_3$ and $G_4$ are not $R_2NH$;

Y is a divalent radical selected from the group consisting of

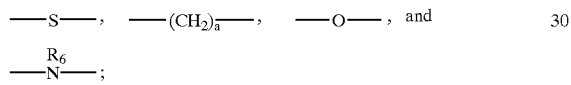

$R_7$ is —$NR_6R_6$, —$OR_6$, —J, —$N(R_6)_3^+$, or —$NR_6(OR_6)$;
M is >$NR_6$, —O—, >$N(C(R_6)_2)_pNR_6R_6$, or >N—$(C(R_6)_2)_p$—$OR_6$;
W is >$NR_6$, —O— or is a bond;
Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

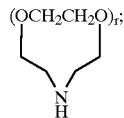

which may be optionally mono- or di-substituted on carbon with $R_6$, hydroxy, —$N(R_6)_2$, —$OR_6$—$(C(R_6)_2)_sOR_6$ or —$(C(R_6)_2)_sN(R_6)_2$; optionally mono-substituted on nitrogen with $R_6$; and optionally mono or di-substituted on a saturated carbon with divalent radicals —O— or —$O(C(R_6)_2)_sO$—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

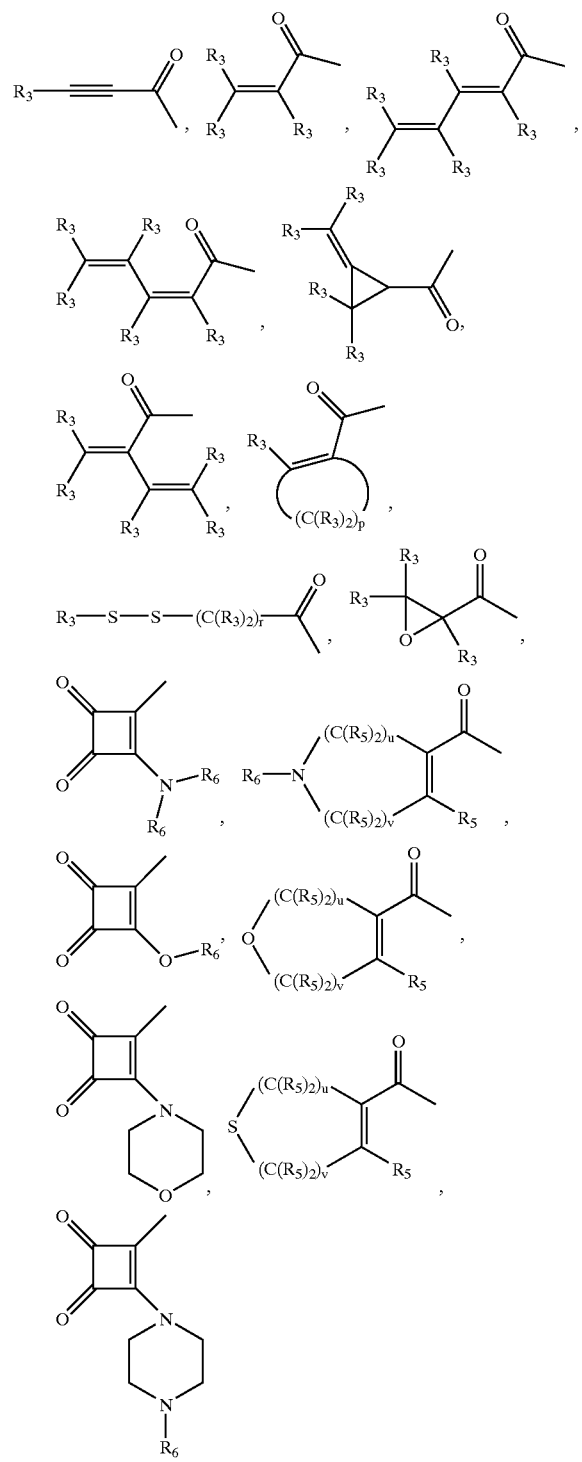

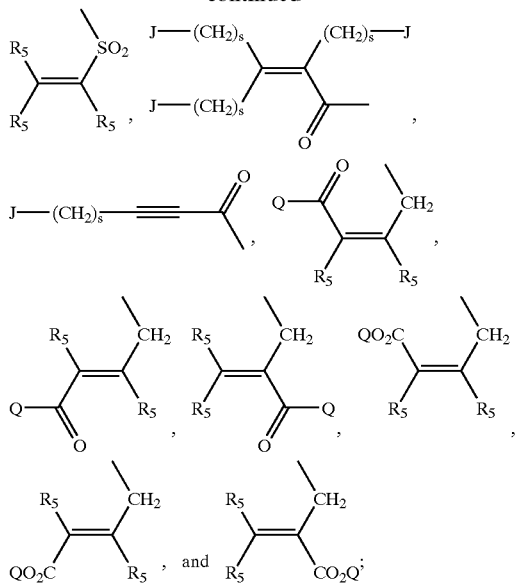

$R_3$ is hydrogen, alkyl of 1–6 carbon atoms, carboxy, carboalkoxy of 1–6 carbon atoms, phenyl, carboalkyl of 2–7 carbon atoms,

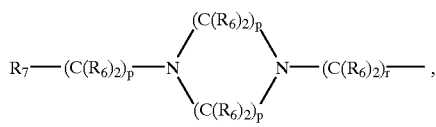

$R_7—(C(R_6)_2)_s—$, $R_7—(C(R_6)_2)_p—M—(C(R_6)_2)_r—$, $R_8R_9—CH—M—(C(R_6)_2)_r—$, or Het-$(C(R_6)_2)_q—W—(C(R_6)_2)_r—$;

$R_5$ is hydrogen, alkyl of 1–6 carbon atoms, carboxy, carboalkoxy of 1–6 carbon atoms, phenyl, carboalkyl of 2–7 carbon atoms,

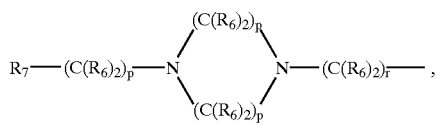

$R_7—(C(R_6)_2)_s—$, $R_7—(C(R_6)_2)_p—M—(C(R_6)_2)_r—$, $R_8R_9—CH—M—(C(R_6)_2)_r—$, or Het-$(C(R_6)_2)_q—W—(C(R_6)_2)_r—$;

$R_8$, and $R_9$ are each, independently, $—(C(R_6)_2)_rNR_6R_6$, or $—(C(R_6)_2)_rOR_6$;

J is independently hydrogen, chlorine, fluorine, or bromine;

Q is alkyl of 1–6 carbon atoms or hydrogen;

a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof,
provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and provided that when $R_3$ is bound to sulfur, it cannot be hydrogen, carboxy, carboalkoxy, or carboalkyl;

and provided that when Y is $—NR_6—$ and $R_7$ is $—NR_6R_6$, $—N(R_6)_3^+$, or $—NR_6(OR_6)$, then g=2–6;

when M is $—O—$ and $R_7$ is $—OR_6$ then p=1–4;

when Y is $—NR_6—$ then k=2–4;

when Y is $—O—$ and M or W is $—O—$ then k=1–4 when W is not a bond with Het bonded through a nitrogen atom then q=2–4 and when W is a bond with Het bonded through a nitrogen atom and Y is $—O—$ or $—NR6—$ then k=2–4;

and finally provided that when A" is the moiety

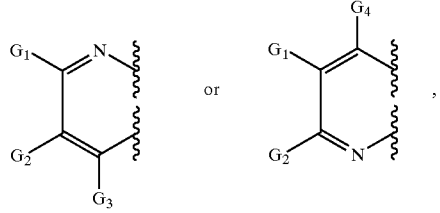

n=0,

Z is NH, $G_1$ is hydrogen, halogen, alkyl, alkoxy, hydroxy, alkanoyloxy of 2–6 carbon atoms, or phenoxy, and $G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino, then X can not be a phenyl ring that is substituted with a hydroxy or alkoxy group.

5. A method of treating, inhibiting the growth of, or eradicating neoplasms in a mammal in need thereof which comprises administering to said mammal a compound of formula 1 having the structure

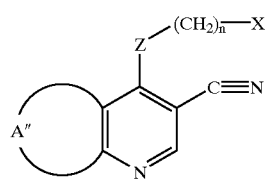

I wherein:

X is the radical

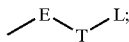

E is Ph;

T is substituted on E at carbon and is
—NH(CH$_2$)$_m$—, —NR(CH$_2$)$_m$—,
—(CH$_2$)$_m$NH—, or —(CH$_2$)$_m$NR—;

L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;

A" is a divalent moiety selected from the group

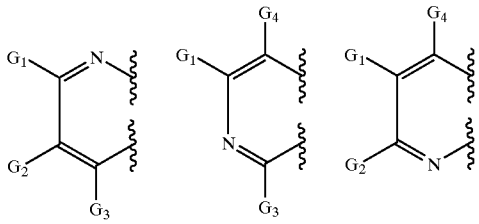

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, R$_2$NH,

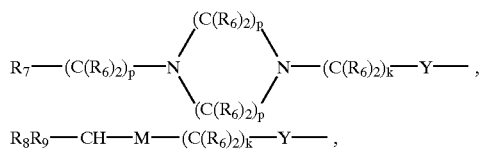

R$_7$—(C(R$_6$)$_2$)$_g$—Y—, R$_7$—(C(R$_6$)$_2$)$_p$—M—(C(R$_6$)$_2$)$_k$—Y—, Het-(C(R$_6$)$_{2q}$—W—(C(R$_6$)$_2$)$_k$—Y—, with the proviso that $G_3$ and $G_4$ are not R$_2$NH;

Y is a divalent radical selected from the group consisting of

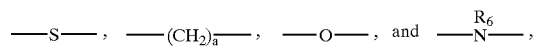

R$_7$ is —NR$_6$R$_6$, —OR$_6$, —J, —N(R$_6$)$_3^+$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene tetrahydrofuran, dioxane, 1,3-dioxolane tetrahydropyran, and

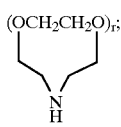

which may be optionally mono- or di-substituted on carbon with $R_6$, hydroxy, $-N(R_6)_2$, $-OR_6-(C(R_6)_2)_sOR_6$ or $-(C(R_6)_2)_sN(R_6)_2$;
optionally mono-substituted on nitrogen with $R_6$; and optionally mono or di-substituted on a saturated carbon with divalent radicals $-O-$ or $-O(C(R_6)_2)_sO-$;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon I atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

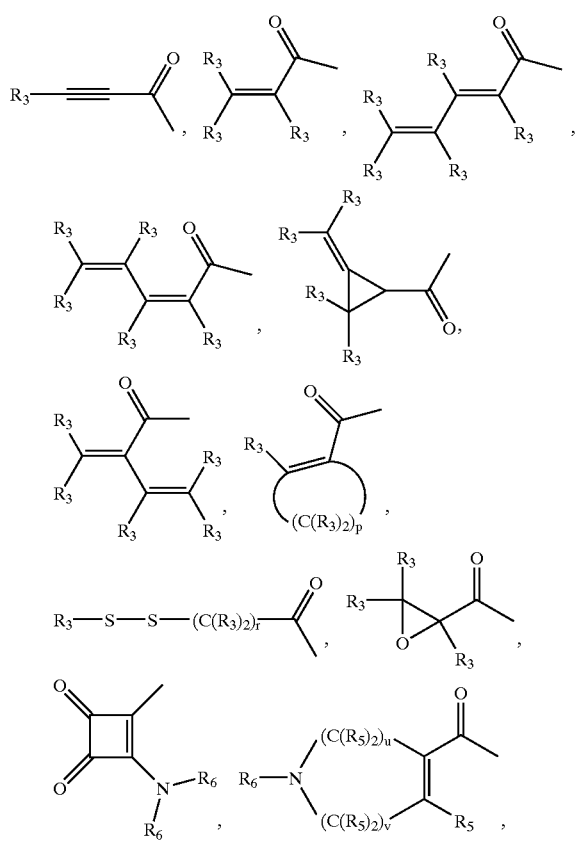

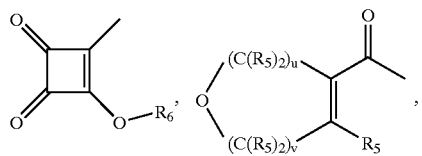

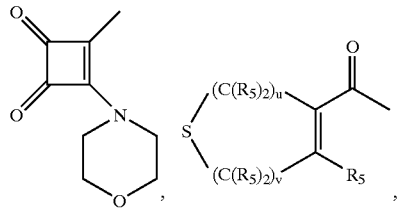

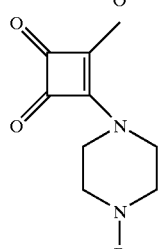

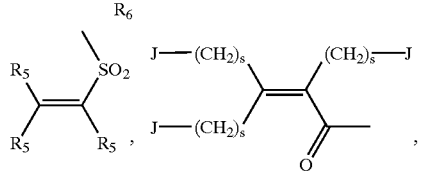

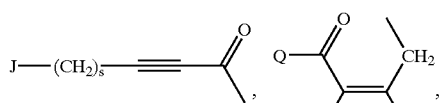

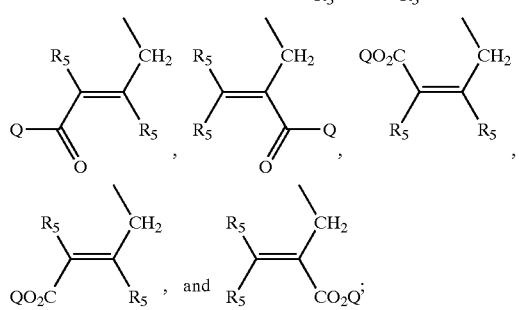

$R_3$ is hydrogen, alkyl of 1–6 carbon atoms, carboxy, carboalkoxy of 1–6 carbon atoms, phenyl, carboalkyl of 2–7 carbon atoms,

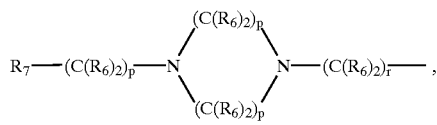

$R_7-(C(R_6)_2)_s-$, $R_7-(C(R_6)_{2p}-M-(C(R_6)_2)_r-$, $R_8R_9-CH-M-(C(R_6)_2)_r-$, or $Het-(C(R_6)_2)_q-W-(C(R_6)_2)_r-$;

$R_5$ is hydrogen, alkyl of 1–6 carbon atoms, carboxy, carboalkoxy of 1–6 carbon atoms, phenyl, carboalkyl of 2–7 carbon atoms,

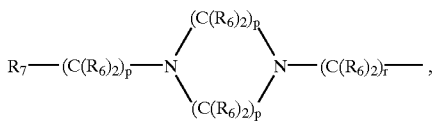

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r NR_6R_6$, or —$(C(R_6)_2)_r OR_6$;

J is independently hydrogen, chlorine, fluorine, or bromine;

Q is alkyl of 1–6 carbon atoms or hydrogen;

a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof,
provided that
when $R_6$ is alkenyl of 2–7 carbon atoms or alkynyl of 2–7 carbon atoms, such alkenyl or alkynyl moiety is bound to a nitrogen or oxygen atom through a saturated carbon atom;
and provided that
when $R_3$ is bound to sulfur, it cannot be hydrogen, carboxy, carboalkoxy, or carboalkyl;
and provided that
when Y is —$NR_6$— and $R_7$ is —$NR_6R_6$, —$N(R_6)_3^+$, or —$NR_6(OR_6)$, then g=2–6;
when M is —O— and $R_7$ is —$OR_6$ then p=1–4;
when Y is —$NR_6$— then k=2–4;
when Y is —O— and M or W is —O— then k=1–4
when W is not a bond with Het bonded through a nitrogen atom then q=2–4
and when W is a bond with Het bonded through a nitrogen atom and Y is —O— or —NR6— then k=2–4;
and finally provided that
when A" is the moiety

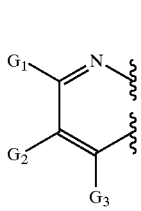 or 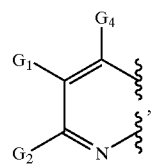, n=0,
Z is NH,
$G_1$ is hydrogen, halogen, alkyl, alkoxy, hydroxy, alkanoyloxy of 2–6 carbon atoms, or phenoxy, and
$G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino,
then X can not be a phenyl ring that is substituted with a hydroxy or alkoxy group.

6. The method according to claim 5 wherein the neoplasm expresses EGFR or erbB2 (Her2).

7. The method according to claim 5 wherein the neoplasm depends, at least in part, on the MAPK pathway.

8. The method according to claim 5 wherein the neoplasm depends, at least in part, on the ECK/LERK-1 pathway.

9. The method according to claim 5 wherein the neoplasm depends, at least in part, on the VEGF/KDR pathway.

10. The method according to claim 5 wherein the neoplasm is selected from the group consisting of breast, kidney, bladder, mouth, larynx, esophagus, stomach, colon, ovary, and lung.

11. A method of treating, inhibiting the progression of, or eradicating polycystic kidney disease in a mammal in need thereof which comprises administering to said mammal a compound of formula I having the structure

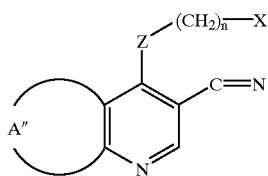

wherein:

X is the radical

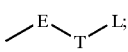

E is Ph;

T is substituted on E at carbon and is
—$NH(CH_2)_m$—, —$NR(CH_2)_m$—,
—$(CH_2)_m NH$—, or —$(CH_2)_m NR$—;

L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;

A" is a diavalent moiety selected from the group

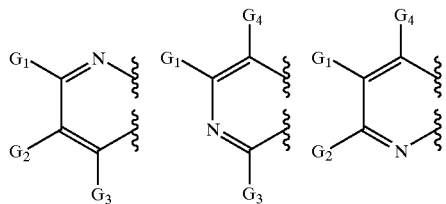

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, $R_2NH$,

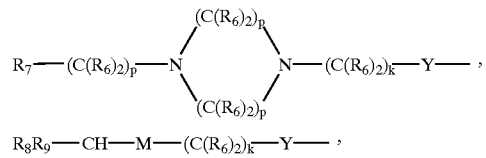

$R_7$—$(C(R_6)_2)_g$—Y—, $R_7$—$(C(R_6)_2)_p$—M—$(C(R_6)_2)_k$—Y—, Het-$(C(R_6)_2)_q$—W—$(C(R_6)_2)_k$—Y—, with the proviso that $G_3$ and $G_4$ are not $R_2NH$;

Y is a divalent radical selected from the group consisting of

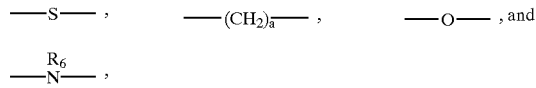

$R_7$ is —$NR_6R_6$, —$OR_6$, —J, —$N(R_6)_3^+$, or —$NR_6(OR_6)$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and

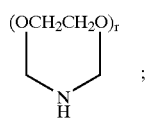

which may be optionally mono- or di-substituted on carbon with $R_6$, hydroxy, —$N(R_6)_2$, —$OR_6$—$(C(R_6)_2)_s OR_6$ or —$(C(R_6)_2)_s N(R_6)_2$; optionally mono-substituted on nitrogen with $R_6$; and optionally mono or di-substituted on a saturated carbon with divalent radicals —O— or —$O(C(R_6)_2)_s O$—;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

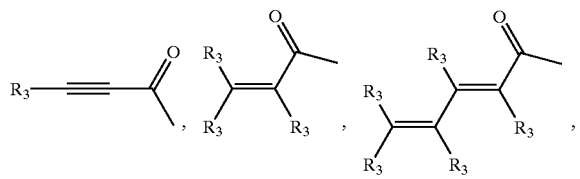

R₃ is hydrogen, alkyl of 1–6 carbon atoms, carboxy, carboalkoxy of 1–6 carbon atoms, phenyl, carboalkyl of 2–7 carbon atoms, $$R_7-(C(R_6)_2)_p-N\underset{(C(R_6)_2)_p}{\overset{(C(R_6)_2)_p}{\diagup\!\!\!\diagdown}}N-(C(R_6)_2)_r-,$$

$R_7-(C(R_6)_2)_s-$, $R_7-(C(R_6)_2)_p-M-(C(R_6)_2)_r-$, $R_8R_9-CH-M-(C(R_6)_2)_r-$, or Het-$(C(R_6)_2)_q-W-(C(R_6)_2)_r-$;

R₅ is hydrogen, alkyl of 1–6 carbon atoms, carboxy, carboalkoxy of 1–6 carbon atoms, phenyl, carboalkyl of 2–7 carbon atoms, $$R_7-(C(R_6)_2)_p-N\underset{(C(R_6)_2)_p}{\overset{(C(R_6)_2)_p}{\diagup\!\!\!\diagdown}}N-(C(R_6)_2)_r-,$$

$R_7-(C(R_6)_2)_s-$, $R_7-(C(R_6)_2)_{2p}-M-(C(R_6)_2)_r-$, $R_8R_9-CH-M-(C(R_6)_2)_r-$, or Het-$(C(R_6)_2)_q-W-(C(R_6)_2)_r-$;

R₈, and R₉ are each, independently, —(C(R₆)₂)ᵣNR₆R₆, or —(C(R₆)₂)ᵣOR₆;

j is independently hydrogen, chlorine, fluorine, or bromine;

Q is alkyl of 1–6 carbon atoms or hydrogen;

a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that
when R₆ is alkenyl of 2–7 carbon atoms or alkynyl of 2–7 carbon atoms, such alkenyl or alkynyl moiety is bound to a nitrogen or oxygen atom through a saturated carbon atom;

and provided that
when $R_3$ is bound to sulfur, it cannot be hydrogen, carboxy, carboalkoxy, or carboalkyl;
and provided that
when Y is —$NR_6$— and $R_7$ is —$NR_6R_6$, —$N(R_6)_3^+$, or —$NR_6(OR_6)$, then g=2–6;
when M is —O— and $R_7$ is —$OR_6$ then p=1–4;
when Y is —$NR_6$— then k=2–4;
when Y is —O— and M or W is —O—then k=1–4
when W is not a bond with Het bonded through a nitrogen atom then q=2–4
and when W is a bond with Het bonded through a nitrogen atom and Y is —O—or —$NR_6$— then k=2–4;
and finally provided that
when A" is the moiety

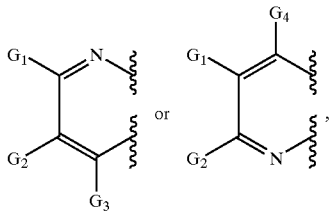

n=0,
Z is NH,
$G_1$ is hydrogen, halogen, alkyl, alkoxy, hydroxy, alkanoyloxy of 2–6 carbon atoms, or phenoxy, and
$G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino,
then X can not be a phenyl ring that is substituted with a hydroxy or alkoxy group.

12. A method of treating, inhibiting the progression of, or eradicating colonic polyps in a mammal in need thereof which comprises administering to said mammal a compound of formula I having the structure

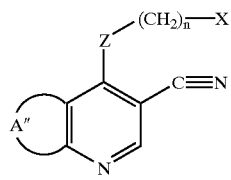

I wherein:
X is the radical

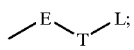

E is Ph;
T is substituted on E at carbon and is
—NH(CH$_2$)$_m$—, —NR(CH$_2$)$_m$—, —(CH$_2$)$_m$NH—, or —(CH$_2$)$_m$NR—;
L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;
A" is a diavalent moiety selected from the group

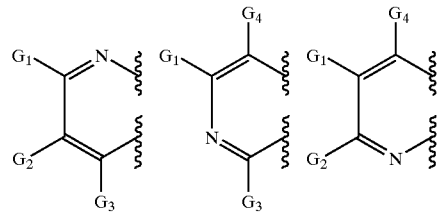

$G_1$, $G_2$, $G_3$, and $G_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, R$_2$NH,

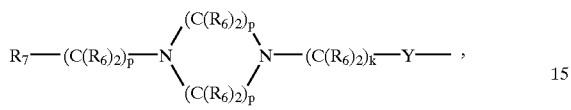

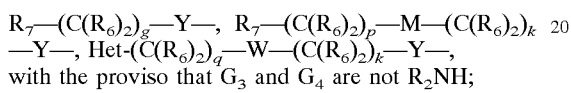

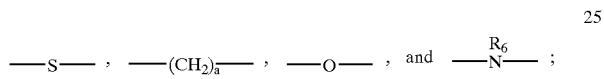

with the proviso that G$_3$ and G$_4$ are not R$_2$NH;

Y is a divalent radical selected from the group consisting of

—S—, —(CH$_2$)$_a$—, —O—, and —N(R$_6$)—;

R$_7$ is —NR$_6$R$_6$, —OR$_6$, —J, —N(R$_6$)$_3$$^+$, or —NR$_6$(OR$_6$);
M is >NR$_6$, —O—, >N—(C(R$_6$)$_2$)$_p$NR$_6$R$_6$, or >N—(C(R$_6$)$_2$)$_p$—OR$_6$;
W is >NR$_6$, —O— or is a bond;
Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane tetrahydropyran, and

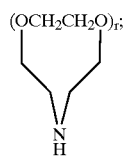

which may be optionally mono- or di-substituted on carbon with R$_6$, hydroxy, —N(R$_6$)$_2$, —OR$_6$—(C(R$_6$)$_2$)$_s$OR$_6$ or —(C(R$_6$)$_2$)$_s$N(R$_6$)$_2$;
optionally mono-substituted on nitrogen with R$_6$; and optionally mono or di-substituted on a saturated carbon with divalent radicals —O— or —O(C(R$_6$)$_2$)$_s$O—;
R$_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

R$_2$, is selected from the group consisting of

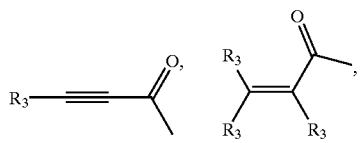

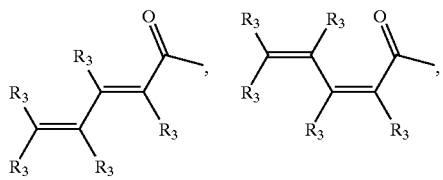

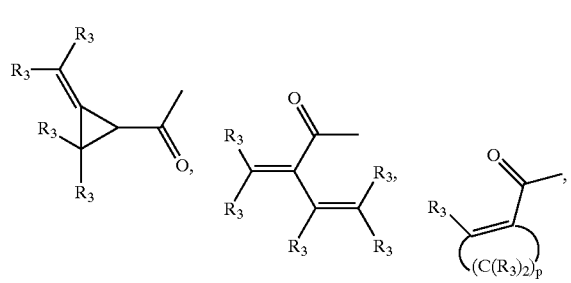

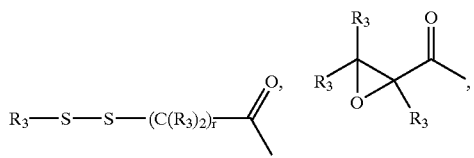

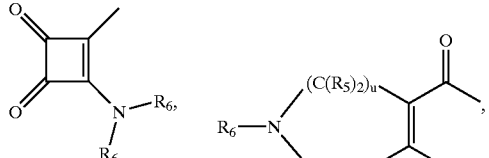

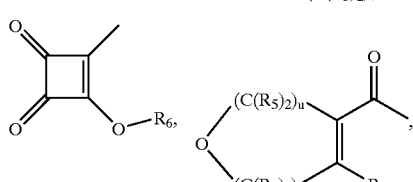

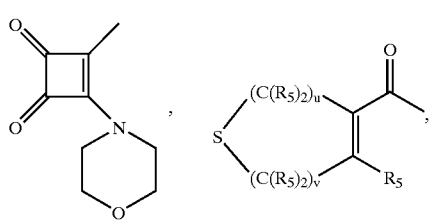

-continued

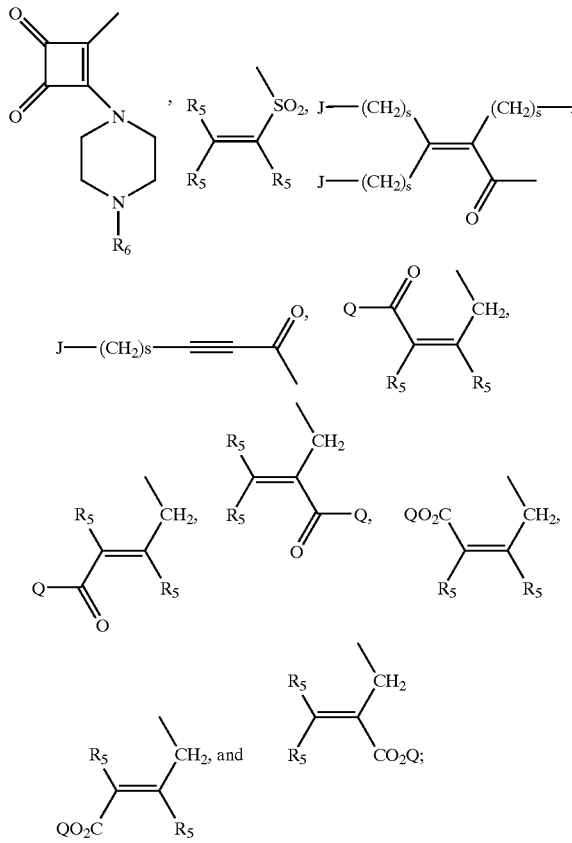

$R_3$ is hydrogen, alkyl of 1–6 carbon atoms, carboxy, carboalkoxy of 1–6 carbon atoms, phenyl, carboalkyl of 2–7 carbon atoms,

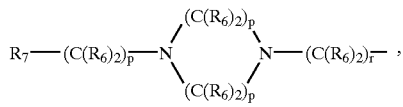

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$W—$(C(R_6)_2)_r$—;

$R_5$ is hydrogen, alkyl of 1–6 carbon atoms, carboxy, carboalkoxy of 1–6 carbon atoms, phenyl, carboalkyl of 2–7 carbon atoms,

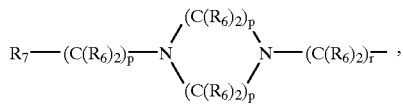

$R_7$—$(C(R_6)_2)_s$—, $R_7$—$(C(R_6)_2)_p$—M—$(C(R_6)_2)_r$—, $R_8R_9$—CH—M—$(C(R_6)_2)_r$—, or Het-$(C(R_6)_2)_q$—W—$(C(R_6)_2)_r$—;

$R_8$, and $R_9$ are each, independently, —$(C(R_6)_2)_r$NR$_6$R$_6$, or —$(C(R_6)_2)_r$OR$_6$;

J is independently hydrogen, chlorine, fluorine, or bromine;

Q is alkyl of 1–6 carbon atoms or hydrogen;

a=0–1;

g=1–6;

k=0–4;

n is 0–1;

m is 0–3;

p=2–4;

q=0–4;

r=1–4;

s=1–6;

u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and provided that when $R_3$ is bound to sulfur, it cannot be hydrogen, carboxy, carboalkoxy, or carboalkyl;

and provided that when Y is —NR$_6$— and $R_7$ is —NR$_6$R$_6$, —N(R$_6$)$_3^+$, or —NR$_6$(OR$_6$), then g=2–8;

when M is —O— and $R_7$ is —OR$_6$ then p=1–4;

when Y is —NR$_6$— then k=2–4;

when Y is —O— and M or W is —O— then k=1–4 when W is not a bond with Het bonded through a nitrogen atom then q=2–4 and when W is a bond with Het bonded through a nitrogen atom and Y is —O— or —NR$_6$— then k=2–4;

and finally provided that when A" is the moiety

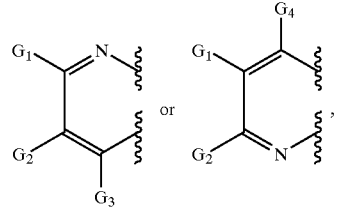

n=0,

Z is NH, $G_1$ is hydrogen, halogen, alkyl, alkoxy, hydroxy, alkanoyloxy of 2–6 carbon atoms, or phenoxy, and $G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino, then X can not be a phenyl ring that is substituted with a hydroxy or alkoxy group.

13. A pharmaceutical composition which comprises a compound of formula I having the structure

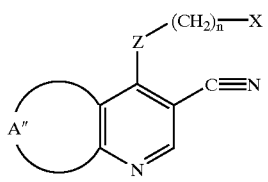

wherein:

X is the radical

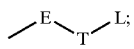

E is Ph;

T is substituted on E at carbon and is
—NH(CH$_2$)$_m$—, —NR(CH$_2$)$_m$—,
—(CH$_2$)$_m$NH—, or —(CH$_2$)$_m$NR—;

L is a 5- or 6-membered heteroaryl ring where the heteroaryl ring contains 1 to 3 heteroatoms selected from N, O, and S; wherein the heteroaryl ring may be optionally mono- or di-substituted with a substituent selected from the group consisting of halogen, oxo, thio, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Ph is phenyl, which may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, carboxyalkyl of 2–7 carbon atoms, carboalkoxyalkyl of 3–8 carbon atoms, aminoalkyl of 1–5 carbon atoms, N-alkylaminoalkyl of 2–9 carbon atoms, N,N-dialkylaminoalkyl of 3–10 carbon atoms, N-alkylaminoalkoxy of 2–9 carbon atoms, N,N-dialkylaminoalkoxy of 3–10 carbon atoms, mercapto, methylmercapto, and benzoylamino;

Z is —NH—;

A″ is a diavalent moiety selected from the group

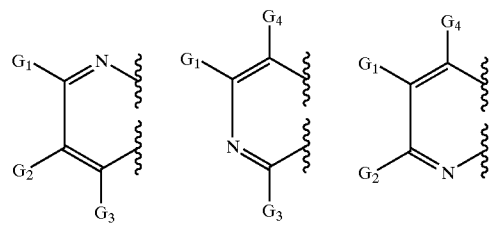

G$_1$, G$_2$, G$_3$, and G$_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 2–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, trifluoromethoxy, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6–12 carbon atoms, phenylamino, benzylamino, R$_2$NH,

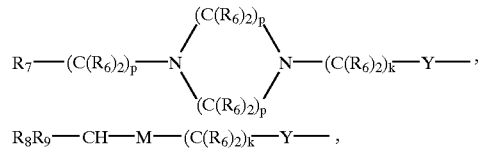

R$_7$—(C(R$_6$)$_2$)$_g$—Y—, R$_7$—(C(R$_6$)$_2$)$_p$—M—(C(R$_6$)$_2$)$_k$—Y—, Het-(C(R$_6$)$_2$)$_q$—W—(C(R$_6$)$_2$)$_k$—Y—, with the proviso that G$_3$ and G$_4$ are not R$_2$NH;

Y is a divalent radical selected from the group consisting of

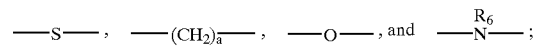

R$_7$ is —NR$_6$R$_6$, —OR$_6$, —J, —N(R$_6$)$_3$$^+$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine tetrazole, piperazine, furan, thiophene, tetrahydrothiophene, tetrahydrofuran, dioxane, 1,3-dioxolane tetrahydropyran, and

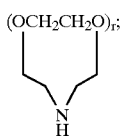

which may be optionally mono- or di-substituted on carbon with $R_6$, hydroxy, $-N(R_6)_2$, $-OR_6-(C(R_6)_2)_sOR_6$ or $-(C(R_6)_2)_sN(R_6)_2$; optionally mono-substituted on nitrogen with $R_6$; and optionally mono or di-substituted on a saturated carbon with divalent radicals $-O-$ or $-O(C(R_6)_2)_sO-$;

$R_6$ is hydrogen, alkyl of 1–6 carbon atoms, alkenyl of 2–6 carbon atoms, alkynyl of 2–6 carbon atoms, cycloalkyl of 1–6 carbon atoms, carboalkyl of 2–7 carbon atoms, carboxyalkyl 2–7 carbon atoms, phenyl, or phenyl optionally substituted with one or more halogen, alkoxy of 1–6 carbon atoms, trifluoromethyl, amino, alkylamino of 1–3 carbon atoms, dialkylamino of 2–6 carbon atoms, nitro, cyano, azido, halomethyl, alkoxymethyl of 2–7 carbon atoms, alkanoyloxymethyl of 2–7 carbon atoms, alkylthio of 1–6 carbon atoms, hydroxy, carboxyl, carboalkoxy of 2–7 carbon atoms, phenoxy, phenyl, thiophenoxy, benzoyl, benzyl, phenylamino, benzylamino, alkanoylamino of 1–6 carbon atoms, or alkyl of 1–6 carbon atoms; with the proviso that the alkenyl or alkynyl moiety is bound to a nitrogen or oxygen atom through a saturated carbon atom;

$R_2$, is selected from the group consisting of

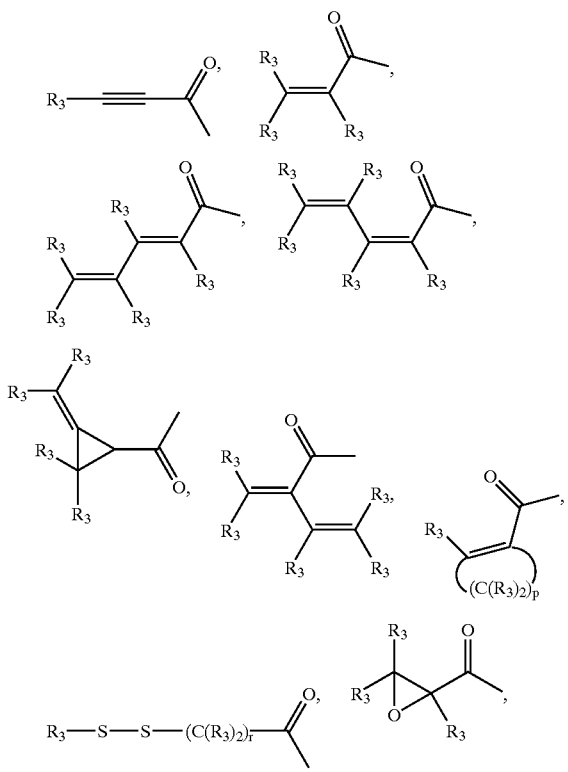

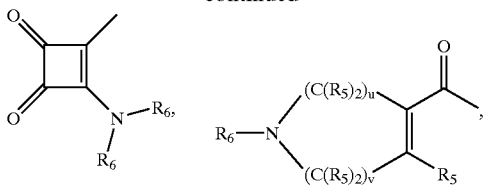

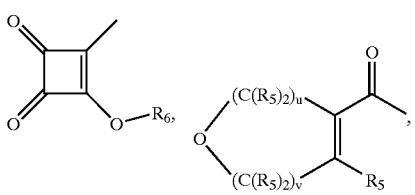

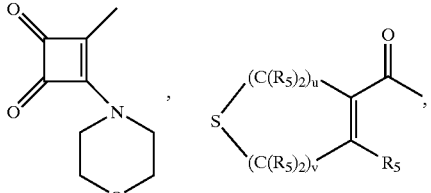

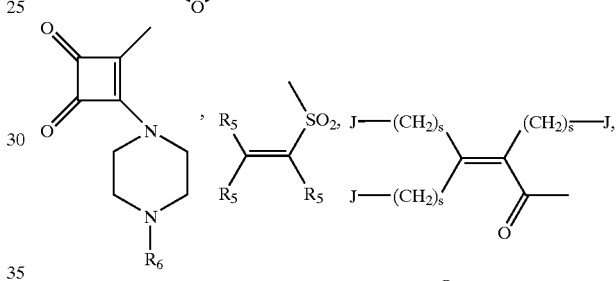

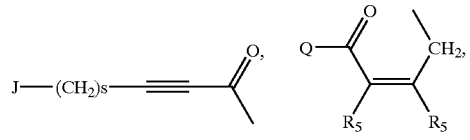

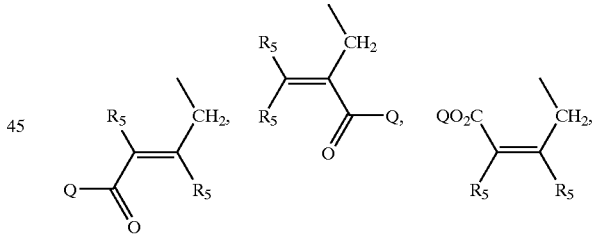

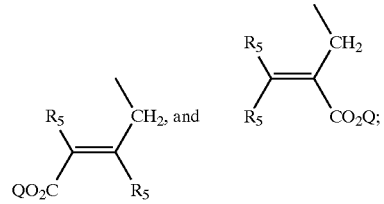

$R_3$ is hydrogen, alkyl of 1–6 carbon atoms, carboxy, carboalkoxy of 1–6 carbon atoms, phenyl, carboalkyl of 2–7 carbon atoms,

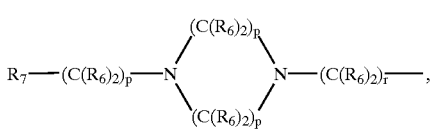

$R_7-(C(R_6)_2)_s-$, $R_7-(C(R_6)_2)_p-M-(C(R_6)_2)_r-$, $R_8R_9-CH-M-(C(R_6)_2)_r-$, $Het-(C(R_6)_2)_q-W-(C(R_6)_2)_r-$;

$R_5$ is hydrogen, alkyl of 1–6 carbon atoms, carboxy, carboalkoxy of 1–6 carbon atoms, phenyl, carboalkyl of 2–7 carbon atoms,

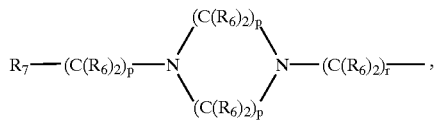

$R_7-(C(R_6)_2)_s-$, $R_7-(C(R_6)_2)_p-M-(C(R_6)_2)_r-$, $R_8R_9-CH-M-(C(R_6)_2)_r-$, $Het-(C(R_6)_2)_q-W-(C(R_6)_2)_r-$;

$R_8$, and $R_9$ are each, independently, $-(C(R_6)_2)_rNR_6R_6$, or $-(C(R_6)_2)_rOR_6$;

J is independently hydrogen, chlorine, fluorine, or bromine;

Q is alkyl of 1–6 carbon atoms or hydrogen;

a=0–1;
g=1–6;
k=0–4;
n is 0–1;
m is 0–3;
p=2–4;
q=0–4;
r=1–4;
s=1–6;
u=0–4 and v=0–4, wherein the sum of u+v is 2–4;

or a pharmaceutically acceptable salt thereof, provided that when $R_6$ is alkenyl of 2–7 carbon atoms or alkynyl of 2–7 carbon atoms, such alkenyl or alkynyl moiety is bound to a nitrogen or oxygen atom through a saturated carbon atom;

and provided that when $R_3$ is bound to sulfur, it cannot be hydrogen, carboxy, carboalkoxy, or carboalkyl;

and provided that when Y is $-NR_6-$ and $R_7$ is $-NR_6R_6$, $-N(R_6)_3^+$, or $-NR_6(OR_6)$, then g=2–6;

when M is $-O-$ and $R_7$ is $-OR_6$ then p=1–4;

when Y is $-NR_6-$ then k=2–4;

when Y is $-O-$ and M or W is $-O-$ then k=1–4 when W is not a bond with Het bonded through a nitrogen atom then q=2–4 and when W is a bond with Het bonded through a nitrogen atom and Y is $-O-$ or $-NR6-$ then k=2–4;

and finally provided that when A" is the moiety

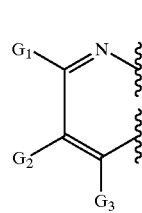 or 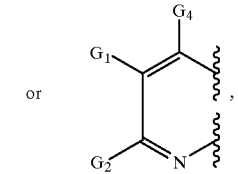, n=0,

Z is NH, $G_1$ is hydrogen, halogen, alkyl, alkoxy, hydroxy, alkanoyloxy of 2–6 carbon atoms, or phenoxy, and $G_2$ is hydrogen, halogen, alkyl, hydroxy, carboxyalkyl, carboalkoxyalkyl, hydroxyalkyl, alkoxy, halomethyl, carboxyl, carboalkoxy, alkanoylamino, or alkenoylamino, then X can not be a phenyl ring that is substituted with a hydroxy or alkoxy group;

and a pharmaceutically acceptable carrier.

* * * * *